United States Patent
Lu et al.

(10) Patent No.: US 9,910,031 B2
(45) Date of Patent: Mar. 6, 2018

(54) COMPOSITIONS AND METHODS FOR MODULATING C-REL-DEPENDENT CYTOKINE PRODUCTION

(71) Applicant: Synta Pharmaceuticals Corporation, Lexington, MA (US)

(72) Inventors: Rongzhen Lu, Lincoln, MA (US); James Barsoum, Lexington, MA (US); Yumiko Wada, Billerica, MA (US)

(73) Assignee: Madrigal Pharmaceuticals, Inc., West Conshohocken, PA (US)

( * ) Notice: Subject to any disclaimer, the term of this patent is extended or adjusted under 35 U.S.C. 154(b) by 225 days.

(21) Appl. No.: 14/542,453

(22) Filed: Nov. 14, 2014

(65) Prior Publication Data
US 2016/0003804 A1 Jan. 7, 2016

Related U.S. Application Data

(60) Continuation of application No. 13/367,825, filed on Feb. 7, 2012, now abandoned, which is a continuation of application No. 11/972,592, filed on Jan. 10, 2008, now abandoned, which is a division of application No. 10/986,553, filed on Nov. 10, 2004, now abandoned.

(60) Provisional application No. 60/519,048, filed on Nov. 10, 2003, provisional application No. 60/519,040, filed on Nov. 11, 2003.

(51) Int. Cl.
*G01N 33/50* (2006.01)
*G01N 33/68* (2006.01)

(52) U.S. Cl.
CPC ..... *G01N 33/5035* (2013.01); *G01N 33/6872* (2013.01); *G01N 2333/4703* (2013.01); *G01N 2333/54* (2013.01); *G01N 2500/10* (2013.01)

(58) Field of Classification Search
None
See application file for complete search history.

(56) References Cited

U.S. PATENT DOCUMENTS

| | | |
|---|---|---|
| 5,597,898 A | 1/1997 | Ghosh |
| 6,001,652 A | 12/1999 | Monia et al. |
| 6,660,733 B2 | 12/2003 | Sun et al. |
| 6,858,606 B2 | 2/2005 | Sun et al. |
| 6,958,332 B2 | 10/2005 | Sun et al. |
| 7,470,681 B2 | 12/2008 | Sun et al. |
| 7,745,436 B2 | 6/2010 | Kostik et al. |
| 7,851,466 B2 | 12/2010 | Wada et al. |
| 7,919,487 B2 | 4/2011 | Sun et al. |
| 2002/0045235 A1 | 4/2002 | Karin et al. |
| 2012/0208203 A1 | 8/2012 | Lu et al. |

FOREIGN PATENT DOCUMENTS

| | | | |
|---|---|---|---|
| WO | WO 03/047516 | * | 6/2003 |
| WO | WO-2003/047516 | | 6/2003 |
| WO | WO-2005/000404 | | 1/2005 |
| WO | WO-2005/046604 | | 5/2005 |
| WO | WO-2005/112938 | | 12/2005 |
| WO | WO-2006/053109 | | 5/2006 |
| WO | WO-2006/053112 | | 5/2006 |
| WO | WO-2006/060194 | | 6/2006 |
| WO | WO-2006/128172 | | 11/2006 |
| WO | WO-2012/093127 | | 12/2012 |

OTHER PUBLICATIONS

Singh et al (J Psychiat Res 31:657-660, 1997).*
Bhakar et al. (Oct. 1, 2002) "Constitutive nuclear factor—kB activity is required for central neuron survival". The Journal of Neuroscience 22(19):8466-8475.
Chen et al. (May 2004) "Shaping the nuclear action of NF-kappaB". Nature Reviews Molecular Cell Biology 5:392-401.
Fairbrother (Dec. 1998) "Novel peptides selected to bind vascular endothelial growth factor target the receptor-binding site". Biochemistry 37:17754-64.
Jeon et al. (Jul. 1998) "Inhibition of NF-kappaB/Rel nuclear translocation by dexamethasone: Mechanism for the inhibition of iNOS gene expression". Biochemistry and molecular biology International. 45(3):435-441.
Jeon et al. "Dexamethasone inhibits IL-1 B gene expression in LPS-stimulated RAW 264.7 cells by blocking NF- B/Rel and AP-1 activation," Immunopharamacology, vol. 48, pp. 173-183 (2000).
Hamilton et al. (Nov. 1998) "Oxidized LDL modulates activation of NFkappB in mononuclear phagocytes by altering the degradation if IkappaBs". Journal of Leukocyte Biology 64:667-674.
Hansen et al. (Jan. 1992) "A novel complex between thep65 subunit of NF-kappaB and c-Rel binds to a DNA element involved in the phorbol ester induction of the human urokinase gene". The EMBO Journal. 11(1): pp. 205-213.
Hillard et al. (Sep. 2002)"Critical roles of c-Rel in autoimmune inflammation and helper T cell differentiation". The Journal of Clinical Investigation. 110(6):843-850.
Singh et al. (1997) "Circulating cytokines in Alzheimer's disease", J. Psychiat. Res., vol. 31 No. 6 pp. 657-660.
International Search Report and Written Opinion for PCT/US04/38241 dated Nov. 10, 2005.

* cited by examiner

*Primary Examiner* — Craig Ricci
(74) *Attorney, Agent, or Firm* — Mintz Levin Cohn Ferris Glovsky and Popeo, P.C.; Muriel Liberto, Esq.

(57) ABSTRACT

The present invention is directed to compositions and methods for modulating c-Rel-dependent cytokine production without materially altering the level of expression of NFκB and/or the amount of IκB. The present invention is also directed to screening for modulators of c-Rel activity as determined by assaying for altered subcellular localization of c-Rel but where the level of expression of NFκB and/or the amount of IκB is materially unaltered.

18 Claims, 9 Drawing Sheets

```
       cggaaggtgt gagccgcaaa cccagcggag ggcgggaaga aggaggaggc ctctagggtg
   61  ntcgggggac tggggggcccc gccggcagag gtccctcggc ctcctgactg actgactgcg
  121  gccgcctccg gccaggacgc tgggagctgc ctgcgggaag gtgcgggggag cggagccatg
  181  gcctccggtg cgtataaccc gtatatagag ataattgaac aacccaggca gaggggaatg
  241  cgtttagat acaaatgtga agggcgatca gcaggcagca ttccagggga gcacagcaca
  301  gacaacaacc gaacataccc ttctatccag attatgaact attatggaaa aggaaaagtg
  361  agaattacat tagtaacaaa gaatgaccca tataaacctc atcctcatga tttagttgga
  421  aaagactgca gagacggcta ctatgaagca gaatttggac aagaacgcag acctttgttt
  481  ttccaaaatt tggggtattcg atgtgtgaag aaaaaagaag taaaagaagc tattattaca
  541  agaataaagg caggaatcaa tccattcaat gtccctgaaa acagctgaa tgatattgaa
  601  gattgtgacc tcaatgtggt gagactgtgt tttcaagtt ttctccctga tgaacatggt
  661  aatttgacga ctgctcttcc tcctgttgtc tcgaacccaa tttatgacaa ccgtgctcca
  721  aatactgcag aattaaggat ttgtcgtgta aacaagaatt gtggaagtgt cagaggagga
  781  gatgaaatat ttctactttg tgacaaagtt cagaaagatg acatagaagt tcgtttgtg
  841  ttgaacgatt gggaagcaaa aggcatcttt tcacaagctg atgtacaccg tcaagtagcc
  901  attgttttca aaactccacc atattgcaaa gctatcacag aacccgtaac agtaaaaatg
  961  cagttgcgga gaccttctga ccaggaagtt agtgaatcta tggatttag atatctgcca
 1021  gatgaaaaag atactacgg caataaagca aagaaacaaa agacaactct gcttttccag
 1081  aaactgtgcc aggatcacgt agaaacaggg tttcgccatg ttgaccagga tggtcttgaa
 1141  ctcctgacat caggtgatcc acccaccttg gcctcccaaa gtgctgggat tacagttaat
 1201  tttcctgaga gaccaagacc tggtctcctc ggttcaattg gagaaggaag atacttcaaa
 1261  aaagaaccaa acttgttttc tcatgatgca gttgtgagag aaatgcctac aggggtttca
 1321  agtcaagcag aatcctacta tccctcacct gggcccatct caagtggatt gtcacatcat
 1381  gcctcaatgg cacctctgcc ttcttcaagc tggtcatcag tggcccaccc caccccacgc
 1441  tcaggcaata caaacccact gagtagtttt tcaacaagga cacttccttc taattcgcaa
 1501  ggtatcccac cattcctgag aatacctgtt gggaatgatt taaatgcttc taatgcttgc
 1561  atttacaaca atgccgatga catagtcgga atggaagcgt catcatgcc atcagcagat
 1621  ttatatggta tttctgatcc caacatgctg tctaattgtt ctgtgaatat gatgacaacc
 1681  agcagtgaca gcatgggaga gactgataat ccaagacttc tgagcatgaa tcttgaaaac
 1741  ccctcatgta attcagtgtt agacccaaga gacttgagac agctccatca gatgtcctct
 1801  tccagtatgt cagcaggcgc caattccaat actactgttt ttgtttcaca atcagatgca
 1861  tttgagggat ctgacttcag ttgtgcagat aacagcatga taaatgagtc gggaccatca
 1921  aacagtacta atccaaacag tcatggtttt gttcaagata gtcagtattc aggtattggc
 1981  agtatgcaaa atgagcaatt gagtgactcc tttccatatg aattttttca agtataactt
 2041  gcaagattta aatcctttta aatcttgata ccacctatat agatgcagca ttttgtattt
 2101  gtctaactgg ggatataata ctatatttat actgtatata taatactgac tgagaatata
 2161  atactgtatt tgagaatata aaaaactttt tcagggaag aagcatacaa ctttggacat
 2221  agcgaataca aaattggaag ctgtcataaa aagacaactc agaggccagg cgcaggngct
 2281  cacacctgta atcctagcac tttgggaggc caaggcgggt ggatcacttg agaccag
```

FIG. 1A

```
  1 masgaynpyi eiieqprqrg mrfrykcegr sagsipgehs tdnnrtypsi qinnyygkgk
 61 vritlvtkng pykphphdlv gkdcrdgyye aefgqerrpl ffqnlgircv kkkevkeaii
121 trikaginpf nvpekqlndi edcdlnvvrl cfqvflpdeh gnlttalppv vsnpiydnra
181 pntaelricr vnkncgsvrg gdeiflicdk vqkddievrf vlndweakgi fsqadvhrqv
241 aivfktppyc kaitepvtvk mqlrrpsdge vsesmdfryl pdekdtygnk akkqkttllf
301 qklcqdhvet gfrhvdgdgl elltsgdppt lasqsagitv nfperprpgl lgsigegryf
361 kkepnlfshd avvremptgv ssqaesyyps pgpissglsh hasmaplpss swssvahptp
421 rsgntnplss fstrtlpsns qgippflrip vgndlnasna ciynnaddiv gmeassmpsa
481 dlygisdpnm lsncsvnmmt tssdsmgetd nprllsmnle npscnsvldp rdlrqlhqms
541 sssmsagans nttvfvsqsd afegsdfsca dnsminesgp snstnpnshg fvqdsqysgi
601 gsmqneqlsd sfpyeffqv
```

FIG. 1B

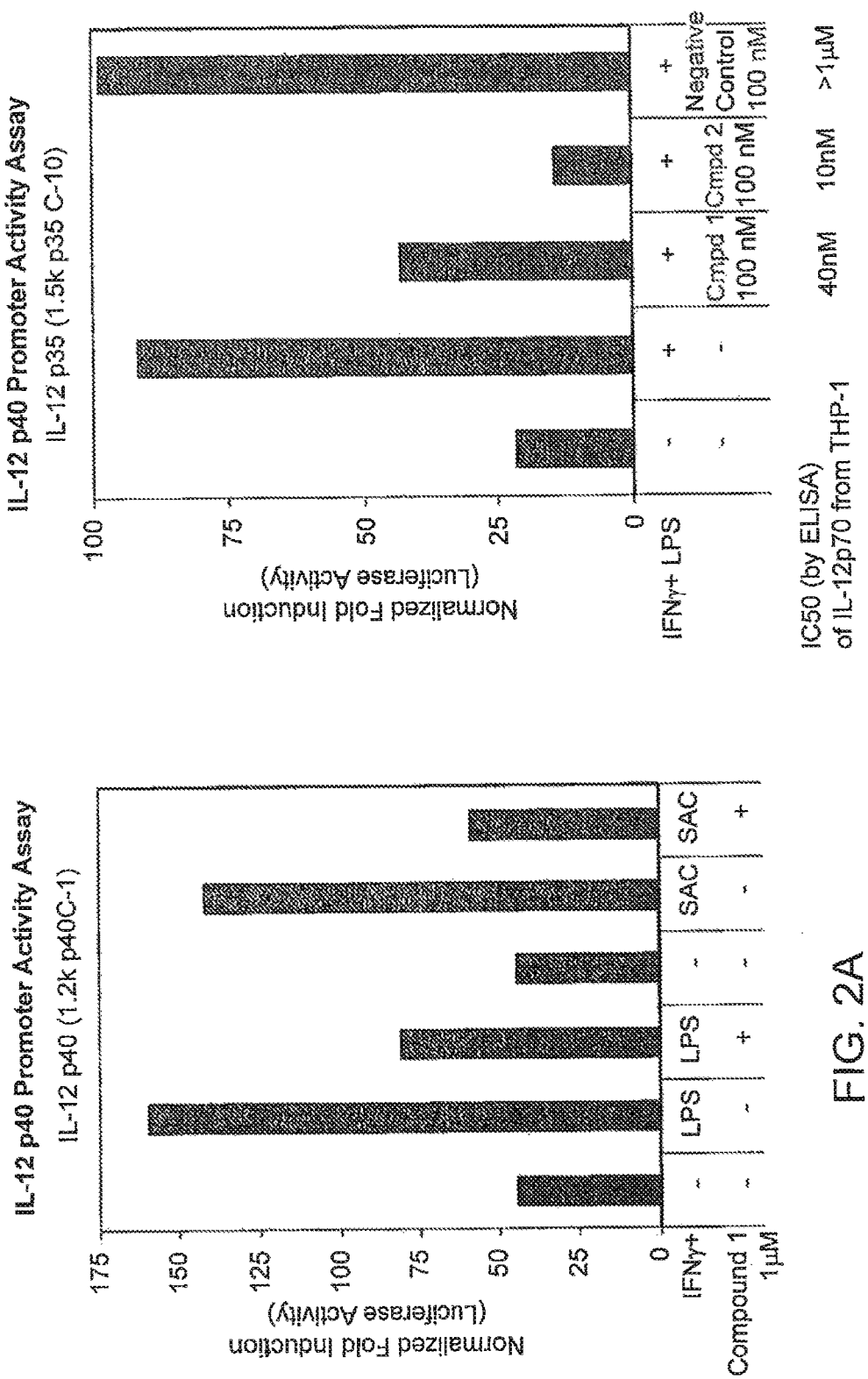

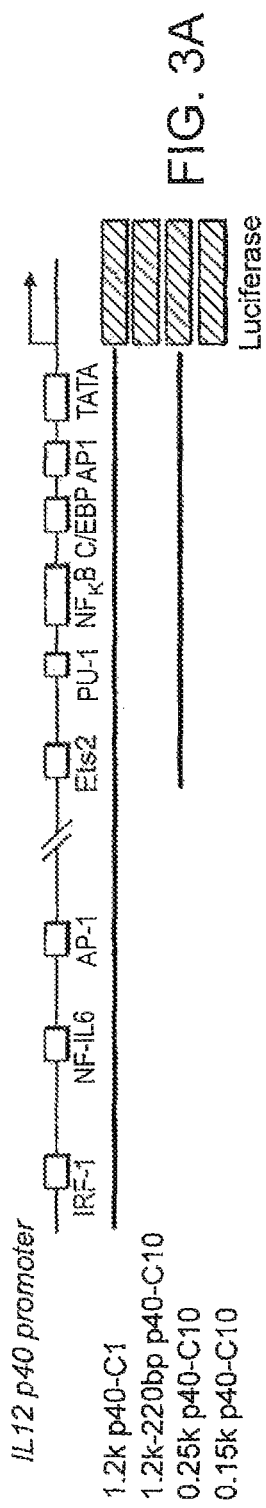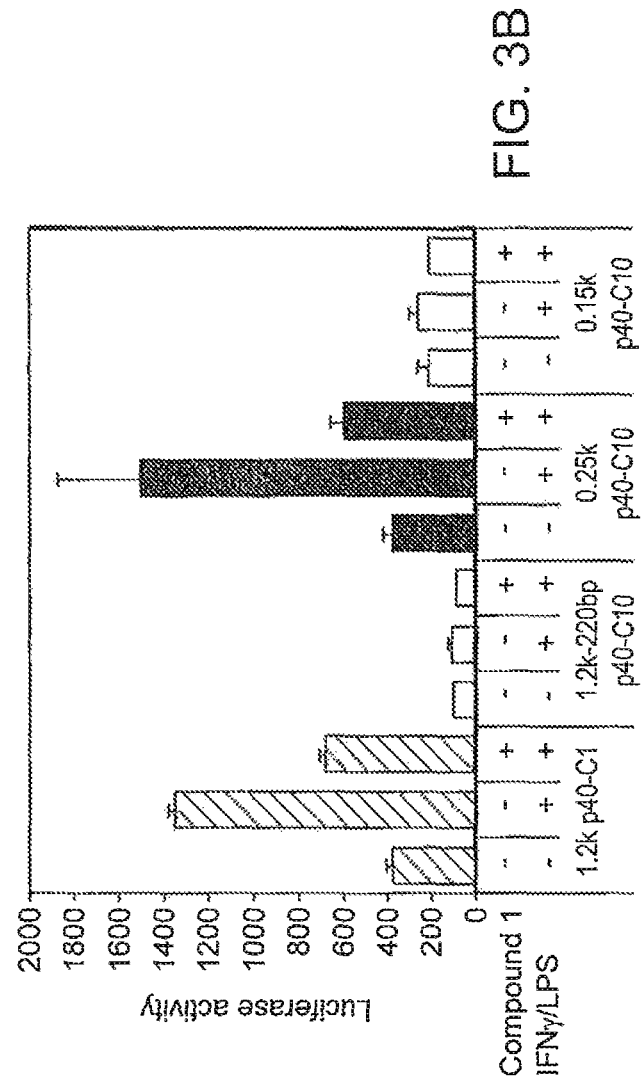
FIG. 3A
FIG. 3B

Western Blot Analysis of THP1 Cell
Nuclear Extracts with Anti-PU-1 Ab materials from Ets2 DNA binding assay

| Bound | | un-bound | | |
|---|---|---|---|---|
| + | + | + | + | IFNg/LPS |
| − | + | − | + | Compound 1 |

PU-1-

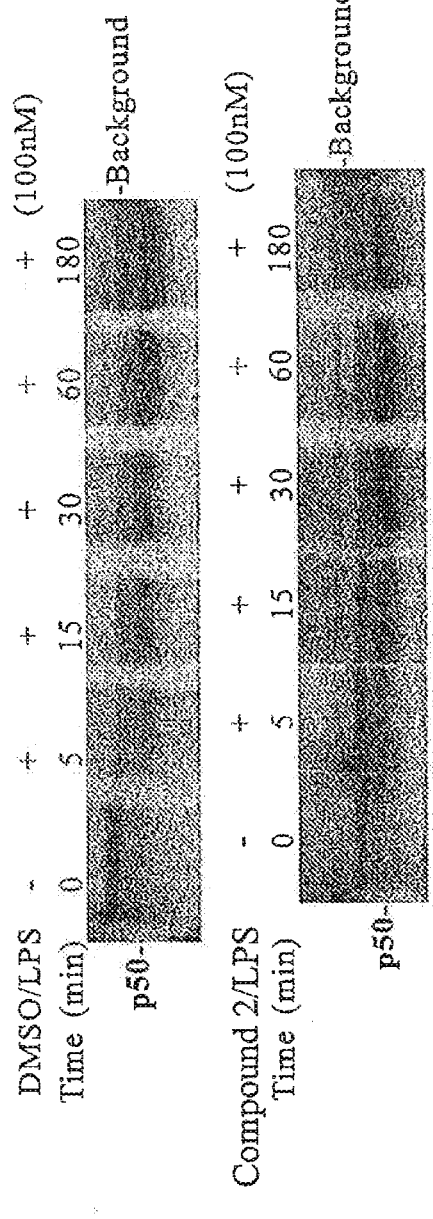
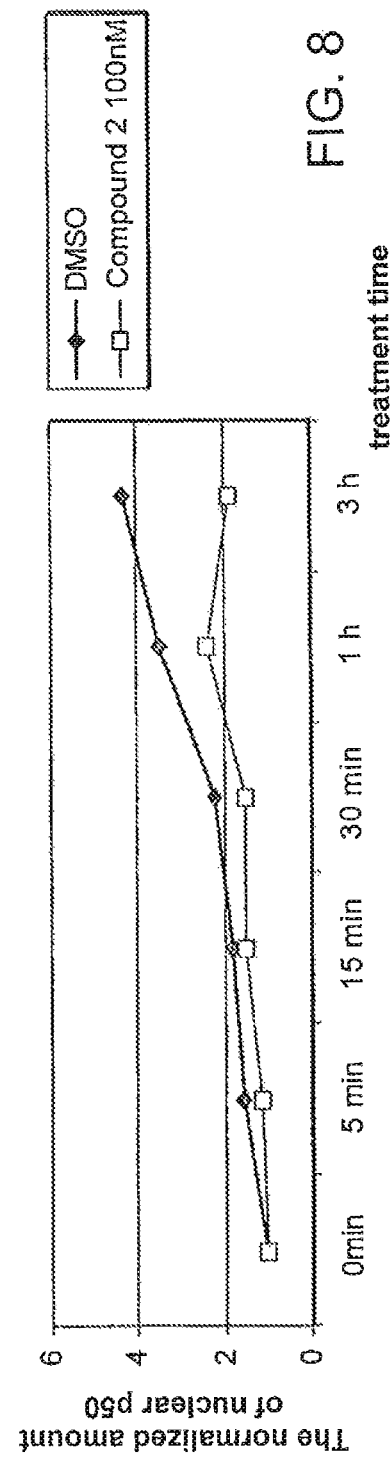

COMPOSITIONS AND METHODS FOR MODULATING C-REL-DEPENDENT CYTOKINE PRODUCTION

This application is a continuation of U.S. application Ser. No. 13/367,825, filed Feb. 27, 2012, which is a continuation of divisional U.S. patent application Ser. No. 11/972,592, filed Jan. 10, 2008, which is a divisional application of U.S. patent application Ser. No. 10/986,553, filed Nov. 10, 2004, abandoned, which claims benefit of U.S. Provisional Patent Application Nos. 60/519,048 and 60/519,040 filed Nov. 10, 2003 and Nov. 11, 2003, respectively. All of the foregoing applications are incorporated by reference herein in their entirety.

FIELD OF THE INVENTION

The present invention is directed to compositions and methods for modulating c-Rel-dependent cytokine production without materially altering the level of expression of NFκB and/or amount of IκB. The present invention is also directed to screening for modulators of c-Rel activity as determined by assaying for altered subcellular localization of c-Rel but where the level of expression of NFκB and/or amount of IκB is materially unaltered.

BACKGROUND OF THE INVENTION

The role of cytokines in the development of autoimmune diseases and inflammatory disorders is well known. Cytokines such as interleukin-12 (IL-12) mediate the acute phase response to inflammatory stimuli, enhance the microbicidal functions of macrophages and other cells, and promote specific lymphocyte responses. IL-12 plays a role in multiple-Th1 dominant autoimmune diseases including, but not limited to, multiple sclerosis, myasthenia gravis, autoimmune neuropathies, Guillain-Barré syndrome, autoimmune uveitis, autoimmune hemolytic anemia, pernicious anemia, autoimmune thrombocytopenia, temporal arteritis, antiphospholipid syndrome, vasculitides, Wegener's granulomatosis, Behcet's disease, psoriasis, dermatitis herpetiformis, pemphigus vulgaris, vitiligo, Crohn's disease, ulcerative colitis, primary biliary cirrhosis, autoimmune hepatitis, Type 1 or immune-mediated diabetes mellitus, Grave's disease, Hashimoto's thyroiditis, autoimmune oophoritis and orchitis, autoimmune disease of the adrenal gland; rheumatoid arthritis, systemic lupus erythematosus, scleroderma, polymyositis, dermatomyositis, spondyloarthropathies, ankylosing spondylitis, Sjogren's syndrome and graft-versus-host disease.

Interleukin-12 (IL-12) is a di-sulfide linked heterodimeric cytokine (p70) composed of two independently regulated subunits, p35 and p40. IL-12 is produced by phagocytic cells and antigen presenting cells, in particular, macrophages and dendritic cells, upon stimulation with bacteria, bacterial products such as lipopolysaccharide (LPS), and intracellular parasites. The well-documented biological functions of IL-12 are induction of interferon-γ expression from T and NK cells and differentiation toward the Th1 T lymphocyte type. IFN-γ, expression of which is induced by IL-12, is a strong and selective enhancer of IL-12 production from monocytes and macrophages. The effect is evident after extended treatment with IFN-γ for at least 8 hours prior to stimulation with LPS or *Staphylococcus aureus* Cowan I (SAC), suggesting that, particularly in chronic diseases in which there is ongoing production of IFN-γ, IL-12 production is augmented by IFN-γ. It is presumed that after an infective or inflammatory stimulus that provokes IL-12 production, the powerful feedback loop promotes IL-12-induced IFN-γ to further augment IL-12 production, leading to consequent excessive production of pro-inflammatory cytokines. The cytokine IL-23 is a heterodimer composed of a p19 subunit and the same p40 subunit of IL-12.

LPS stimulates the translocation of p50/c-Rel and p50/p65 heterodimers in macrophages from the cytoplasm to the nucleus. Both of these heterodimers bind to the NFκB site in the promoter of p40. However, only c-Rel has been shown to be important for the LPS-induced signaling through Toll-like receptor-4 (TLR4) that leads to the production of p40 in response to numerous pro-inflammatory stimuli in vitro and in vivo.

Citation or identification of any reference in Section 2 or in any other section of this application shall not be construed as an admission that such reference is available as prior art to the present invention.

SUMMARY OF THE INVENTION

The present invention provides methods of identifying a molecule that selectively alters c-Rel-dependent transcription by detecting alterations in the level of c-Rel molecules localized to the nucleus of a cell (e.g., an immune cell) contacted with one or more candidate molecules, without detecting any alterations in the expression of NFκB and/or amount of IκB, relative to a cell not contacted with a candidate molecule or contacted with a negative control such as phosphate buffered saline (PBS), (e.g., assessing but detecting no material altering of the expression levels of NFkB and or IkB). In one embodiment, the invention provides a method of identifying a molecule that selectively alters c-Rel-dependent transcription, comprising the following steps in the order stated: (a) contacting a cell (e.g., an immune cell such as an natural killer cell, a T cell, a macrophage, a dendritic cell, or a monocyte) with one or more candidate molecules; and (b) detecting localization of c-Rel molecules in the cell, wherein an increase or decrease in the amount of c-Rel in the nucleus without materially altering the level of expression of NFκB and/or amount of IκB relative to said amount in a cell not so contacted with the one or more candidate molecules or contacted with a negative control such as PBS indicates that the candidate molecules alter c-Rel-dependent transcription. In accordance with this embodiment, the cell may be contacted with the candidate molecule(s) while concurrently being stimulated with IFN-γ and/or lipopolysaccharide (LPS). Preferably, in accordance with this embodiment, the cell is contacted with the candidate molecule(s) following stimulation with IFN-γ and/or lipopolysaccharide (LPS). In a specific embodiment, the cell contacted with the candidate molecule is a macrophage, monocyte or dendritic cell.

In another embodiment, the invention provides a method of identifying a molecule that selectively alters c-Rel-dependent transcription, comprising the following steps in the order stated: (a) contacting a cell (e.g., an immune cell such as an natural killer cell, a T cell, a macrophage, a dendritic cell, or a monocyte) recombinantly expressing one or more candidate molecules; and (b) detecting localization of c-Rel molecules in the cell, wherein an increase or decrease in the amount of c-Rel in the nucleus without materially altering the level of expression of NFκB and/or amount of IκB relative to said amount in a cell not expressing one or more candidate molecules indicates that the candidate molecules alter c-Rel-dependent transcription. In accordance with this embodiment, the cell may be stimulated with IFN-γ and/or lipopolysaccharide (LPS) prior to, concurrently with or subsequent to the induction of the expression of the candidate molecule(s). In a specific embodiment, the cell expressing the candidate molecule(s) is a macrophage, monocyte or dendritic cell.

Any method known in the art may be used to measure the level of c-Rel localized to the nucleus of a cell. For example, the localization of c-Rel in a cell may be detected by contacting the cell with an antibody to c-Rel or a binding region of said antibody, and a fluorescently labeled binding partner of said antibody under conditions conducive to immunospecific binding. Alternatively, the localization of c-Rel in a cell may be detected by contacting the cell with a fluorescently labeled antibody to c-Rel or a binding region of said antibody under conditions conducive to immunospecific binding. The localization of c-Rel in a cell may be detected also be detected by sequencing by mass spectroscopy nuclear proteins isolated from the cell. Further, The localization of c-Rel in a cell may be detected by measuring the amount of c-Rel-dependent transcription, e.g., measuring p40 transcription, or total cellular p40 protein levels, or total nuclear p40 protein levels.

Any method known in the art may be used to measure the level of NFκB expression, including, but not limited to, measuring the protein levels of NFκB family members p50, p65 and c-Rel by immunospecific binding or measuring the levels of the encoding mRNA. In a particular embodiment, expression of NFκB refers to the expression of NFκB family members p50, p65 and c-Rel, as measured, e.g., in a western blot using a whole cell protein extract. Any method known in the art may be used to measure the amount of IκB, including, but not limited to, measuring the total amount of IκB protein or encoding mRNA in the cell, as measured, e.g., in a western blot using either a whole cell or cytoplasmic protein extract, or measuring the level of IκB degradation by, e.g., measuring IκB protein levels in the treated cells as compared to levels in the untreated cells.

In the context of NFκB and/or IκB (including IκBα and IκBβ) expression and/or amount, the term "materially altering" as used herein means a greater than 10%, preferably greater than 20%, 30%, 40%, 50%, 60%, 70%, 75%, 80%, 90% or 95% change in the level of expression of NFκB and/or amount of IκB.

Any protein whose expression is dependent on c-Rel transcription may be altered as result of altering c-Rel-dependent transcription. Examples of such proteins include, but are not limited to, IL-6, IL-10, IL-12, IL-15, IL-23, IFN-γ, Bcl-xL, Mcl-1, Jagged-1, IRF-4 and c-myc. Accordingly, the expression of one or more of such proteins may be altered by a molecule identified in accordance with the methods of the invention as selectively altering c-Rel-dependent transcription. In a preferred embodiment, the level of expression of IL-12 and/or IL-23 are altered by a molecule identified in accordance with the methods of the invention as selectively altering c-Rel-dependent transcription.

The present invention provides methods of identifying a molecule that selectively alters c-Rel-dependent cytokine production by detecting alterations in the level of c-Rel molecules localized to the nucleus of a cell (e.g., an immune cell) of contacted with one or more candidate molecules, without detecting any alterations in the expression of NFκB and/or amount of IκB, relative to a cell not contacted with a candidate molecule or contacted with a negative control such phosphate buffered saline (PBS) (e.g., assessing but detecting no material altering the expression levels of NFκB and or IκB). Examples of cytokines dependent on c-Rel for production proteins include, but are not limited to, IL-6, IL-10, IL-12, IL-15, IL-23, and IFN-γ. Accordingly, the expression of one or more of such cytokines may be altered by a molecule identified in accordance with the methods of the invention as selectively altering c-Rel-dependent cytokine production. In a preferred embodiment, the level of expression of IL-12 and/or IL-23 are altered by a molecule identified in accordance with the methods of the invention as selectively altering c-Rel-dependent cytokine production.

In one embodiment, the present invention provides a method of identifying a molecule that selectively alters c-Rel-dependent cytokine production in a cell comprising the following steps in the order stated: (a) contacting the cell (preferably, after or concurrently with IFN-γ and/or LPS stimulation) with one or more candidate molecules; and (b) detecting localization of c-Rel molecules in the cell, wherein an increase or decrease in the amount of c-Rel in the nucleus without materially altering the level of expression of NFκB and/or amount of IκB relative to said amount in a cell not so contacted with the one or more candidate molecules or contacted with a negative control such as PBS indicates that the candidate molecules alter c-Rel-dependent cytokine production. In accordance with this embodiment, the cell contacted with the candidate molecule(s) is preferably a macrophage, monocyte or dendritic cell.

In another embodiment, the present invention provides a method of identifying a molecule that selectively alters c-Rel-dependent cytokine production in a cell comprising the following steps in the order stated: (a) recombinantly expressing within the cell one or more candidate molecules; and (b) detecting localization of c-Rel molecules in the cell, wherein an increase or decrease in the amount of c-Rel in the nucleus without materially altering the level of expression of NFκB and/or amount of IκB relative to said amount in a cell not expressing one or more candidate molecules indicates that the candidate molecules alter c-Rel-dependent cytokine production. In accordance with this embodiment, the cell may be stimulated with IFN-γ and/or lipopolysaccharide (LPS) prior to, concurrently with or subsequent to the induction of the expression of the candidate molecule(s). In a specific embodiment, the cell expressing the candidate molecule(s) is a macrophage, monocyte or dendritic cell.

In another embodiment, the present invention provides a method of identifying a molecule that selectively alters c-Rel-dependent cytokine production in a cell (after or concurrently with IFN-γ and/or LPS stimulation) comprising the following steps in the order stated: (a) microinjecting into the cell one or more candidate molecules; and (b) detecting localization of c-Rel molecules in the cell, wherein an increase or decrease in the amount of c-Rel in the nucleus without materially altering the level of expression of NFκB and/or amount of IκB relative to said amount in a cell not so microinjected with the one or more candidate molecules or microinjected with a negative control indicates that the candidate molecules alter c-Rel-dependent cytokine production. In accordance with this embodiment, the cell contacted with the candidate molecule(s) is preferably a macrophage, monocyte or dendritic cell.

In one embodiment, a molecule identified in accordance with the methods of the invention as selectively altering c-Rel-dependent transcription and/or c-Rel-dependent cytokine production in a cell does not alter the level of expression and/or activity of one or more of the following proteins: PU-1, Jak1, Jak2, STAT1, ERK, PKA, IκB and p38 kinases. In another embodiment, a molecule identified in accordance with the methods of the invention as selectively altering c-Rel-dependent transcription and/or c-Rel-dependent cytokine production in a cell reduces the level of ICSBP in the nucleus. In a particular embodiment, a molecule identified in accordance with the methods of the invention as selectively altering c-Rel-dependent transcription and/or c-Rel-dependent cytokine production in a cell decreases in the level of interferon consensus sequence binding protein (ICSBP) in the nucleus of a cell by at least 10%, preferably, at least 15%, at least 18%, at least 20%<at least 25%, at least 30%, at least 35%, at least 40% or at least 45%.

In another embodiment, a molecule identified in accordance with the methods of the invention as selectively altering c-Rel-dependent transcription and/or c-Rel-dependent cytokine production in a cell reduces the level of p50 in the nucleus. In another embodiment, a molecule identified in accordance with the methods of the invention as selectively altering c-Rel-dependent transcription and/or c-Rel-dependent cytokine production in a cell increases the level of p65 in the nucleus. In a particular embodiment, a molecule identified in accordance with the methods of the invention as selectively altering c-Rel-dependent transcription and/or dependent cytokine production in a cell increases the level of p65 in the nucleus by at least 35%, preferably at least 40%, at least 45%, at least 50%, at least 55%, at least 59%, at least 60%, at least 65%, at least 70%, at least 75% or at least 85%. In another embodiment, a molecule identified in accordance with the methods of the invention as selectively altering c-Rel-dependent transcription and/or c-Rel-dependent cytokine production in a cell decreases p35 transcription. In yet another embodiment, a molecule identified in accordance with the methods of the invention as selectively altering c-Rel-dependent transcription and/or c-Rel-dependent cytokine production in a cell results in two or more of the following effects: a decrease in the level of ICSBP in the nucleus, a decrease in the level of p50 in the nucleus, an increase in the level of p65 in the nucleus, and a decrease in p35 transcription.

The present invention also provides a method for identifying a drug target for mediating selective inhibition of c-Rel-dependent transcription in a cell comprising the following steps in the order stated: (a) labeling one or more agents that reduce the amount of c-Rel in the nucleus of the cell without materially altering the level of expression of NFκB or the amount of IκB; (b) contacting the cell with the one or more labeled agents under conditions that form a complex between the one or more labeled agents and the drug target; (c) isolating the complex; and (d) identifying the drug target from the complex. In another embodiment, the present invention provides a method for identifying a drug target that selectively inhibits c-Rel-dependent cytokine production in a cell comprising the following steps in the order stated: (a) labeling one or more agents that reduce the amount of c-Rel in the nucleus of a cell without materially altering the level of expression of NFκB or amount of IκB; (b) contacting the cell with the one or more labeled agents under conditions that form a complex between the one or more labeled agents and the drug target; (c) isolating the complex; and (d) identifying the drug target from the complex. The identified drug target can then be used to identify compounds for altering cytokine expression levels, in particular c-Rel-dependent cytokine levels.

The present invention also is directed to a method for identifying molecules whose expression or activity is altered due to alteration of c-Rel subcellular localization, i.e., an increase or decrease of c-Rel in the nucleus comprising altering the subcellular localization of c-Rel by contacting a cell with a molecule that alters c-Rel subcellular localization but does not alter the level of expression of NFκB or amount of IκB, and identifying molecules whose expression or activity is altered in cells contacted with the molecule as compared to cells not contacted with the molecule or contacted with a negative control such as PBS.

In one embodiment of the present invention, methods are provided for modulating the activity of c-Rel comprising contacting a cell expressing c-Rel with a molecule that alters the subcellular localization of c-Rel, particularly a decrease in the nucleus of c-Rel, but does not materially alter the level of expression of NFκB or amount of IκB in a cell. In an aspect of this embodiment, the total level of c-Rel protein in the cell is unchanged. In alternative aspect, the total level of c-Rel protein in the cell is altered. In another embodiment the invention, methods are provided for modulating c-Rel-dependent cytokine production in a cell without materially altering the level of NFκB expression or amount of IκB in the cell comprising contacting the cell expressing c-Rel with a molecule that alters the subcellular localization of c-Rel but does not materially alter the level of NFκB expression or amount of IκB. In an aspect of the above-embodiment, the molecule is identified by one or more of the screening assays described above. In a particular embodiment, the molecule is identified by a screening method comprising contacting a cell with one or more candidate molecules; and detecting localization of c-Rel molecules in the cell, such that those molecules that cause a decrease in the amount of c-Rel in the nucleus without materially altering the level of expression of NFκB and/or amount of IκB relative to said amount in a cell not so contacted or contacted with a negative control such as PBS are identified.

In a specific embodiment, the present invention provides a method for inhibiting c-Rel-dependent cytokine production in a cell without materially altering the level of expression of NFκB and/or amount of IκB comprising contacting a cell with a molecule that reduces the amount of c-Rel in the nucleus but does not materially alter the level of expression of NFκB and/or amount of IκB, e.g., a molecule identified in a screening assay described above. In one aspect of the embodiment, the method comprises contacting a cell with a molecule that reduces the amount of c-Rel in the nucleus but does not materially alter the level of NFκB expression in the cell as measured by, e.g., the amount of p50, p65 and c-Rel in a cell extract. In another aspect, the method comprises contacting a cell with a molecule that reduces the amount of c-Rel in the nucleus but does not materially alter the amount of IκB in the cell as measured by, e.g., amount of IκB in the cell.

The present invention also provides methods for diagnosing or screening for the presence of or a predisposition for developing a disease or disorder characterized by aberrant c-Rel subcellular localization but with normal levels of expression of NFκB and/or amount of IκB in a subject by measuring the level of c-Rel localization to the nucleus in a sample derived from the subject, in which a decrease or increase in the level of nuclear localization of c-Rel relative to the level of localization in an analogous sample not having the disease or disorder or a predisposition for developing the disease or disorder indicates the presence of the disease or disorder or the predisposition for developing the disease or disorder.

The present invention also provides methods of treating a disease or disorder associated with c-Rel-dependent cytokine production in a subject in need thereof comprising administering to the subject a molecule in an amount effective to reduce the amount of c-Rel in the nucleus of a cell expressing a c-Rel dependent cytokine but that does not materially alter the level of expression of NFκB and/or amount of IκB in the cell. Non-limiting examples of such molecules include those identified utilizing the assays described herein. Preferably, the subject is human. In one aspect of this embodiment, the disease or disorder is an IL-12 production-related disease. In another embodiment, the disease or disorder is an autoimmune disease.

The present invention also provides a method of enhancing the activity of a first agent that inhibits production of a first cytokine in a subject in need thereof comprising administering to the patient the first agent together with a second agent that inhibits production of a second cytokine without materially altering the level of expression of NFκB and/or amount of IκB in a cell expressing the first and/or second cytokine, in which said second cytokine is a c-Rel-dependent cytokine. In one aspect of this embodiment, the first and second cytokine are the same or are different. Preferably, the subject is human. In certain aspects, the first agent is for treatment of autoimmune/inflammatory diseases that does not alter c-Rel activity or subcellular localization.

The present invention also provides a method for evaluating the biological effect of an agent that reduces the amount of c-Rel in the nucleus of a cell without materially altering the level of expression of NFκB and/or amount of IκB in the cell comprising contacting the cell with the agent and observing any phenotypic effects in the cell. In another embodiment, the invention is directed to a method for evaluating the biological effect of an agent in a subject, which agent reduces the amount of c-Rel in the nucleus of a cell without materially altering the level of expression of NFκB and/or amount of IκB, said method comprising administering the agent to the subject and observing any phenotypic effects in the subject. The subject is a mammal, e.g., mouse, rat, monkey, dog, pig, human, etc.

The present invention provides compositions comprising a molecule that reduces the amount of c-Rel in the nucleus of a cell without materially altering the level of expression of NFκB and/or amount of 1 KB. The present invention further provides methods of treating or preventing diseases or disorders associated with aberrant c-Rel-dependent cytokine production, such as, e.g., autoimmune disorders, comprising administering to a subject in need thereof such a composition. In certain embodiments the molecule does not have a compound as described in U.S. Pat. No. 6,384,032; U.S. patent application Ser. No. 09/594,362 filed May 7, 2002; U.S. patent application Ser. No. 10/006,624 filed Nov. 30, 2001 (Publication No. 20020082259); U.S. patent application Ser. No. 10/000,742 filed Nov. 30, 2001 (Publication No. 20030139403); U.S. patent application Ser. No. 10/192,347 filed Jul. 10, 2002 (Publication No. 20030114446); U.S. patent application Ser. No. 10/305,039 filed Nov. 26, 2002; International Patent Publication No. WO 00/78757; International Patent Publication No. WO 03/04516; International Patent Application PCT/US03/32546 filed Oct. 14, 2003; U.S. Provisional Patent Application Ser. No. 60/518,791 filed Nov. 10, 2003; U.S. Provisional Patent Application Ser. No. 60/518,787 filed Nov. 10, 2003; U.S. Provisional Patent Application Ser. No. 60/518,788 filed Nov. 10, 2003U.S. patent application Ser. No. 10/985,627, entitled, "Fused Heterocyclic Compounds," Mitsunori Ono et al, filed Nov. 10, 2004; U.S. patent application Ser. No. 10/985,716, entitled, "Heteroaryl Hydrazone Compounds," Mitsunori Ono et al, filed Nov. 10, 2004; U.S. patent application Ser. No. 10/985,696, entitled, "Pyridine Compounds," Mitsunori Ono, et al, filed Nov. 10, 2004, each of which is incorporated by reference herein in its entirety.

In certain embodiments the molecule does not have a compound as described in U.S. Pat. No. 6,384,032; U.S. patent application Ser. No. 09/594,362 filed May 7, 2002; U.S. patent application Ser. No. 10/006,624 filed Nov. 30, 2001 (Publication No. 20020082259); U.S. patent application Ser. No. 10/000,742 filed Nov. 30, 2001 (Publication No. 20030139403); U.S. patent application Ser. No. 10/192,347 filed Jul. 10, 2002 (Publication No. 20030114446); International Patent Publication No. WO 00/78757; International Patent Publication No. WO 03/04516, each of which is incorporated by reference herein in its entirety.

In certain embodiments the molecule does not have a compound as described in U.S. Pat. No. 6,680,315; U.S. Pat. No. 6,693,097; U.S. Pat. No. 6,660,733; U.S. patent application Ser. No. 10/655,672; U.S. patent application Ser. No. 10/656,671; U.S. patent application Ser. No. 10/305,039 filed Nov. 26, 2002; U.S. patent application Ser. No. 10/656,360 filed Sep. 5, 2003; International Patent Application PCT/US03/32546 filed Oct. 14, 2003; U.S. Provisional Patent Application Ser. No. 60/518,791 filed Nov. 10, 2003; U.S. Provisional Patent Application Ser. No. 60/518,787 filed Nov. 10, 2003; U.S. Provisional Patent Application Ser. No. 60/518,788 filed Nov. 10, 2003; U.S. patent application Ser. No. 10/985,627, entitled, "Fused Heterocyclic Compounds," Mitsunori Ono et al, filed Nov. 10, 2004; U.S. patent application Ser. No. 10/985,716, entitled, "Heteroaryl Hydrazone Compounds," Mitsunori Ono et al, filed Nov. 10, 2004; U.S. patent application Ser. No. 10/985,696, entitled, "Pyridine Compounds," Mitsunori Ono, et al, filed Nov. 10, 2004, each of which is incorporated by reference herein in its entirety.

In certain embodiments the molecule does not have a compound as described in U.S. Pat. No. 6,680,315; U.S. Pat. No. 6,384,032; U.S. patent application Ser. No. 10/656,360 filed Sep. 5, 2003; U.S. patent application Ser. No. 09/594,362 filed May 7, 2002; U.S. patent application Ser. No. 10/655,672; U.S. patent application Ser. No. 10/656,671; U.S. patent application Ser. No. 10/006,624 filed Nov. 30, 2001 (Publication No. 20020082259); U.S. patent application Ser. No. 10/000,742 filed Nov. 30, 2001 (Publication No. 20030139403); U.S. patent application Ser. No. 10/192,347 filed Jul. 10, 2002 (Publication No. 20030114446); International Patent Publication No. WO 00/78757; International Patent Publication No. WO 03/04516; International Patent Application PCT/US03/32546 filed Oct. 14, 2003, each of which is incorporated by reference herein in its entirety.

In certain embodiments the molecule does not have a compound as described in U.S. Provisional Patent Application Ser. No. 60/518,791 filed Nov. 10, 2003; U.S. Provisional Patent Application Ser. No. 60/518,787 filed Nov. 10, 2003; U.S. Provisional Patent Application Ser. No. 60/518,788 filed Nov. 10, 2003; U.S. patent application Ser. No. 10/985,627, entitled, "Fused Heterocyclic Compounds," Mitsunori Ono et al, filed Nov. 10, 2004; U.S. application Ser. No. 10/985,716, entitled, "Heteroaryl Hydrazone Compounds," Mitsunori Ono et al, filed Nov. 10, 2004; U.S. patent application Ser. No. 10/985,696, entitled, "Pyridine Compounds," Mitsunori Ono, et al, filed Nov. 10, 2004, each of which is incorporated by reference herein in its entirety.

In other embodiments, the molecule does have a structure as described in U.S. Pat. No. 6,384,032; U.S. patent application Ser. No. 09/594,362 filed May 7, 2002; U.S. patent application Ser. No. 10/006,624 filed Nov. 30, 2001 (Publication No. 20020082259); U.S. patent application Ser. No. 10/000,742 filed Nov. 30, 2001 (Publication No. 20030139403); U.S. patent application Ser. No. 10/192,347 filed Jul. 10, 2002 (Publication No. 20030114446); U.S. patent application Ser. No. 10/305,039 filed Nov. 26, 2002; International Patent Publication No. WO 00/78757; International Patent Publication No. WO 03/04516; International Patent Application PCT/US03/32546 filed Oct. 14, 2003; U.S. Provisional Patent Application Ser. No. 60/518,791 filed Nov. 10, 2003; U.S. Provisional Patent Application Ser. No. 60/518,787 filed Nov. 10, 2003; U.S. Provisional Patent Application Ser. No. 60/518,788 filed Nov. 10, 2003; U.S. patent application Ser. No. 10/985,627, entitled, "Fused Heterocyclic Compounds," Mitsunori Ono et al, filed Nov. 10, 2004; U.S. patent application Ser. No. 10/985,716, entitled, "Heteroaryl Hydrazone Compounds," Mitsunori Ono et al, filed Nov. 10, 2004; U.S. patent application Ser. No. 10/985,696, entitled, "Pyridine Compounds," Mitsunori Ono, et al, filed Nov. 10, 2004, each of which is incorporated by reference herein in its entirety. In one aspect, the molecule is identified by any of the screening methods disclosed herein. In another aspect, the molecule is purified by techniques known in the art.

In other embodiments, the molecule does have a structure as described in U.S. Pat. No. 6,384,032; U.S. patent application Ser. No. 09/594,362 filed May 7, 2002; U.S. patent application Ser. No. 10/006,624 filed Nov. 30, 2001 (Publication No. 20020082259); U.S. patent application Ser. No. 10/000,742 filed Nov. 30, 2001 (Publication No. 20030139403); U.S. patent application Ser. No. 10/192,347 filed Jul. 10, 2002 (Publication No. 20030114446); International Patent Publication No. WO 00/78757; International Patent Publication No. WO 03/04516, each of which is incorporated by reference herein in its entirety. In one aspect, the molecule is identified by any of the screening methods disclosed herein. In another aspect, the molecule is purified by techniques known in the art.

In other embodiments, the molecule does have a structure as described in U.S. Pat. No. 6,680,315; U.S. Pat. No. 6,693,097; U.S. Pat. No. 6,660,733; U.S. patent application Ser. No. 10/655,672; U.S. patent application Ser. No. 10/656,671; U.S. patent application Ser. No. 10/305,039 filed Nov. 26, 2002; U.S. patent application Ser. No. 10/656,360 filed Sep. 5, 2003; International Patent Application PCT/US03/32546 filed Oct. 14, 2003; U.S. Provisional Patent Application Ser. No. 60/518,791 filed Nov. 10, 2003; U.S. Provisional Patent Application Ser. No. 60/518,787 filed Nov. 10, 2003; U.S. Provisional Patent Application Ser. No. 60/518,788 filed Nov. 10, 2003; U.S. patent application Ser. No. 10/985,627, entitled, "Fused Heterocyclic Compounds," Mitsunori Ono et al, filed Nov. 10, 2004; U.S. patent application Ser. No. 10/985,716, entitled, "Heteroaryl Hydrazone Compounds," Mitsunori Ono et al, filed Nov. 10, 2004; U.S. patent application Ser. No. 10/985,696, entitled, "Pyridine Compounds," Mitsunori Ono, et al, filed Nov. 10, 2004, each of which is incorporated by reference herein in its entirety. In one aspect, the molecule is identified by any of the screening methods disclosed herein. In another aspect, the molecule is purified by techniques known in the art.

In other embodiments, the molecule does have a structure as described in U.S. Pat. No. 6,680,315; U.S. Pat. No. 6,384,032; U.S. patent application Ser. No. 10/656,360 filed Sep. 5, 2003; U.S. patent application Ser. No. 09/594,362 filed May 7, 2002; U.S. patent application Ser. No. 10/655,672; U.S. patent application Ser. No. 10/656,671; U.S. patent application Ser. No. 10/006,624 filed Nov. 30, 2001 (Publication No. 20020082259); U.S. patent application Ser. No. 10/000,742 filed Nov. 30, 2001 (Publication No. 20030139403); U.S. patent application Ser. No. 10/192,347 filed Jul. 10, 2002 (Publication No. 20030114446); International Patent Publication No. WO 00/78757; International Patent Publication No. WO 03/04516; International Patent Application PCT/US03/32546 filed Oct. 14, 2003, each of which is incorporated by reference herein in its entirety. In one aspect, the molecule is identified by any of the screening methods disclosed herein. In another aspect, the molecule is purified by techniques known in the art.

In other embodiments, the molecule does have a structure as described in U.S. Provisional Patent Application Ser. No. 60/518,791 filed Nov. 10, 2003; U.S. Provisional Patent Application Ser. No. 60/518,787 filed Nov. 10, 2003; U.S. Provisional Patent Application Ser. No. 60/518,788 filed Nov. 10, 2003; U.S. patent application Ser. No. 10/985,627, entitled, "Fused Heterocyclic Compounds," Mitsunori Ono et al, filed Nov. 10, 2004; U.S. patent application Ser. No. 10/985,716, entitled, "Heteroaryl Hydrazone Compounds," Mitsunori Ono et al, filed Nov. 10, 2004; U.S. patent application Ser. No. 10/985,696, entitled, "Pyridine Compounds," Mitsunori Ono, et al, filed Nov. 10, 2004, each of which is incorporated by reference herein in its entirety. In one aspect, the molecule is identified by any of the screening methods disclosed herein. In another aspect, the molecule is purified by techniques known in the art.

Other Embodiments

In other embodiments, the present invention is directed to a method for inhibiting c-Rel-dependent cytokine production in a cell without materially altering the level of NFκB transcription factor expression and without materially altering the level of IκB degradation comprising contacting a molecule to a cell, which molecule reduces the amount of c-Rel in the nucleus of the cell without materially altering the level of NFκB transcription factor expression and without materially altering the level of IκB degradation. In a particular embodiment, the c-Rel-dependent cytokine is IL-12. In certain aspects of this embodiment, IL-12 transcription is inhibited, or the amount of p65 in the nucleus is increased or c-Rel translocation to the nucleus is inhibited, or c-Rel expression is not materially altered. In other aspects, IL-12/IL-23 p40 expression is inhibited, or the NFκB element of the IL-12/23 subunit p40 promoter is inhibited, or activation of the Ets-2 element of the IL-12/IL-23 subunit p40 promoter is inhibited. In yet other aspects, IL-12 subunit p35 expression is inhibited, and/or the NFκB element of IL-12 subunit p35 promoter is inhibited. In yet other aspects, the amount of ICSBP in the nucleus is also reduced, or ICSBP expression is inhibited. In certain aspects, the cell is selected from the group consisting of macrophages, monocytes and dendritic cells.

In yet another particular embodiment, the c-Rel-dependent cytokine is IL-23. In certain aspects of this embodiment, the amount of p65 in the nucleus is increased, or c-Rel translocation to the nucleus is inhibited, or c-Rel expression is not materially altered. In yet other aspects, IL-12/IL-23 subunit p40 expression is inhibited, or the NFκB element of IL-12/23 subunit p40 promoter is inhibited, or activation of the Ets-2 element of the IL-12/23 subunit p40 promoter is inhibited, or the amount of ICSBP in the nucleus is also reduced. In yet other aspects, ICSBP expression is inhibited. In certain aspects, the cell is selected from the group consisting of macrophages, monocytes and dendritic cells.

In other embodiments, the present invention is directed to a method for identifying an agent (otherwise referred to as a candidate molecule or compound) that selectively inhibits c-Rel dependent cytokine production comprising contacting the cell with a test agent; measuring the amount of c-Rel in the nucleus of the cell; and selecting those agents that reduce the amount of c-Rel in the nucleus of the cell without materially altering the level of NFκB transcription factor expression and without materially altering the level of IκB degradation. In certain aspects of this embodiment, the amount of c-Rel in the nucleus is measured in step using a luciferase assay. The c-Rel dependent cytokine can be IL-12 or IL-23.

In yet another embodiment, the invention provides methods for target discovery. In one aspect, a method for identifying an agent that selectively inhibits c-Rel dependent cytokine production is provided, which method comprises labeling an agent that reduces the amount of c-Rel in the nucleus of a cell without materially altering the level of NFκB transcription factor expression and without materially altering the level of IκB degradation; contacting the cell with the labeled agent under conditions that form a complex between the labeled agent and the drug target; isolating the complex; and identifying the drug target from the complex. In this embodiment, the c-Rel dependent cytokine is IL-12 or IL-23.

The present invention is also directed to a method for treating a disorder associated with c-Rel-dependent cytokine production in a patient in need thereof comprising administering to the patient an effective amount of an agent that reduces the amount of c-Rel in the nucleus of a cell that produces the cytokine without materially altering the level of NFκB transcription factor expression and without materially altering the level of IκB degradation. In one aspect, the disorder is an autoimmune disease selected from the group consisting of: multiple sclerosis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, dermatitis herpetiformis, pemphigus vulgaris, vitiligo, Crohn's disease, ulcerative colitis, primary biliary cirrhosis, autoimmune hepatitis, Type 1 or immune-mediated diabetes mellitus, Grave's disease, Hashimoto's thyroiditis, autoimmune oophoritis and orchitis, autoimmune disease of the adrenal gland; rheumatoid arthritis, systemic lupus erythematosus, scleroderma, polymyositis, dermatomyositis, spondyloarthropathies, ankylosing spondylitis, Sjogren's syndrome and graft-versus-host disease.

In another embodiment, the present invention is also directed to a method for treating a disorder associated with c-Rel-dependent cytokine production in a subject identified as being in need thereof. The subject may be identified as being in need thereof by a health care professional or may be self-diagnosed. The method comprises administering to the patient an effective amount of an agent that reduces the amount of c-Rel in the nucleus of a cell that produces the cytokine without materially altering the level of NFκB transcription factor expression and without materially altering the level of IκB degradation. In one aspect, the disorder is an autoimmune disease selected from the group consisting of; multiple sclerosis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, dermatitis herpetiformis, pemphigus vulgaris, vitiligo, Crohn's disease, ulcerative colitis, primary biliary cirrhosis, autoimmune hepatitis, Type 1 or immune-mediated diabetes mellitus, Grave's disease, Hashimoto's thyroiditis, autoimmune oophoritis and orchitis, autoimmune disease of the adrenal gland; rheumatoid arthritis, systemic lupus erythematosus, scleroderma, polymyositis, dermatomyositis, spondyloarthropathies, ankylosing spondylitis, Sjogren's syndrome and graft-versus-host disease.

In another embodiment, a compound identified by a screening method according to the invention is labeled with instructions for use. The instructions may include directions for administration to a subject identified to be in need thereof, dosages, dosage forms, and duration of use. A subject may be a mammal, such as a human, primate, dog, horse, pig, cow or cat.

In yet another embodiment, the invention is directed to a method of enhancing the activity of a first agent that inhibits production of a first cytokine in a patient in need thereof, said method comprising administering to the patient the first agent together with a second agent that inhibits production of a second cytokine without materially altering the level of NFκB transcription factor expression and without materially altering the level of IκB degradation, wherein production of the second cytokine is c-Rel-dependent. In certain aspects, the first cytokine and the second cytokine are the same or the first cytokine and the second cytokine are different. In other aspects, the second cytokine is IL-12 or IL-23.

In yet another embodiment, the invention is directed to a method for evaluating the biological effect of an agent that reduces the amount of c-Rel in the nucleus of a cell without materially altering the level of NFκB transcription factor expression and without materially altering the level of IκB degradation comprising contacting the cell with the agent and observing any phenotypic effects in the cell. In yet another embodiment, the invention is directed to a method for evaluating the biological effect in a subject of an agent that reduces the amount of c-Rel in the nucleus of a cell without materially altering the level of NFκB transcription factor expression and without materially altering the level of IκB degradation comprising contacting the cell with the agent and observing any phenotypic effects in the subject.

In yet another embodiment, the present invention is directed to a compound that reduces the amount of c-Rel in the nucleus of a cell without materially altering the level of NFκB transcription factor expression and without materially altering the level of IκB degradation, provided that the compound does not have the structures described in U.S. Pat. No. 6,384,032; PCT publication WO 00/78757.

BRIEF DESCRIPTION OF THE FIGURES

FIGS. 1A-1B recite the nucleotide and amino acid sequences of human c-Rel (SEQ ID NOS:1 and 2, respectively).

FIGS. 2A and 2B are graphs showing the ability of test molecules to inhibit IFN-γ and IFN-γ/LPS induced p40 (FIG. 2A) and p35 (FIG. 2B) expression.

FIG. 3A is a schematic of the different test promoters used and FIG. 3B is a graph demonstrating the ability of the various test promoters to respond to IFN-γ/LPS stimulation.

FIG. 7 is an immunoblot that shows the effect of a test molecule on NF-kB p50 nuclear translocation.

FIG. 8 graphically presents the results of a densitometry showing the effect of a test molecule on p50 nuclear translocation.

DETAILED DESCRIPTION OF THE INVENTION

Figure 4:
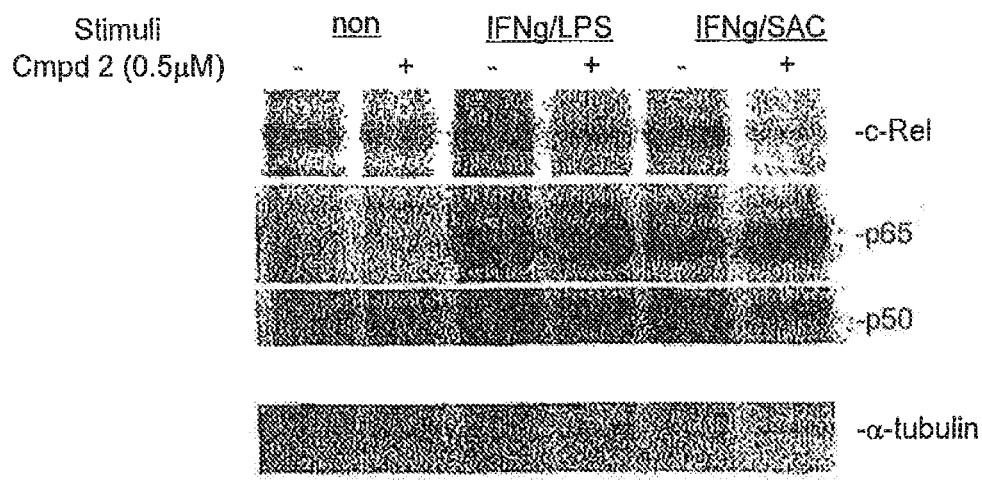
FIG. 4 is a western blot analysis of THP-1 nuclear extracts in stimulated and non-stimulated cells with regard to the presence of NFκB family members c-Rel, p65 or p50; α-tubulin is an internal control.

The present invention is based, in part, on the inventors' discovery that the activity of c-Rel, particularly levels of c-Rel present in the nucleus, can be increased or decreased without materially altering the expression of NFκB or the amount of IκB.

The present invention is directed to a method of identifying a molecule that selectively alters c-Rel-dependent transcription in a cell comprising the following steps in the order stated: (a) contacting the cell with one or more candidate molecules; and (b) detecting localization of c-Rel molecules in the cell, wherein an increase or decrease in the amount of c-Rel in the nucleus without materially altering the level of expression of NFκB and/or amount of IκB relative to said amount in a cell not so contacted with the one or more candidate molecules indicates that the candidate molecules alter c-Rel-dependent transcription. In another embodiment, the present invention is directed to a method of identifying a molecule that selectively alters c-Rel-dependent cytokine production in a cell comprising the following steps in the order stated: (a) contacting the cell with one or more candidate molecules; and (b) detecting localization of c-Rel molecules in the cell, wherein an increase or decrease in the amount of c-Rel in the nucleus without materially altering the level of expression of NFκB and/or amount of IκB relative to said amount in a cell not so contacted with the one or more candidate molecules indicates that the candidate molecules alter c-Rel-dependent cytokine production. In another embodiment, the present invention is directed to a method of identifying a molecule that selectively alters c-Rel-dependent cytokine production in a cell comprising the following steps in the order stated: (a) recombinantly expressing within the cell one or more candidate molecules; and (b) detecting localization of c-Rel molecules in the cell, wherein an increase or decrease in the amount of c-Rel in the nucleus without materially altering the level of expression of NFκB and/or amount of IκB relative to said amount in a cell not so contacted with the one or more candidate molecules indicates that the candidate molecules alter c-Rel-dependent cytokine production. In specific embodiments, the c-Rel-dependent cytokine is IL-12 or IL-23.

The present invention is also directed to a method of enhancing the activity of a first agent that inhibits production of a first cytokine in a subject in need thereof comprising administering to the patient the first agent together with a second agent that inhibits production of a second cytokine without materially altering the level of expression of NFκB and/or amount of IκB in a cell expressing the first and/or second cytokine, in which said second cytokine is a c-Rel-dependent cytokine. In aspect of this embodiment, the first and second cytokine are the same or are different. Preferably, the subject is human.

Detection of c-Rel/KB Subcellular Localization

Any method known in the art for detecting the subcellular localization of c-Rel, i.e., to the nucleus or cytoplasm, can be used in the present invention. For example, and not by way of limitation, one such method of detection is contacting a cell with an antibody specific for c-Rel and then detecting whether the antibody localizes to the nucleus. A particular method of detecting c-Rel subcellular localization is to contact a labeled anti-c-Rel antibody, e.g., labeled with a fluorescent dye, and a labeled anti-DNA antibody, e.g., with a fluorescent dye different from the anti-c-Rel antibody, to whole cells and then to detect cells having both labels co-localized in the cell by, e.g., laser scanning microscopy.

Thus, detection methods encompassed by the present invention include immunofluorescence or immunoelectron microscopy, for in situ detection of the c-Rel molecule. In situ detection may be accomplished by contacting a cell endogenously or recombinantly expressing a c-Rel molecule with a labeled molecule that binds to c-Rel and detecting any binding that occurs and that is localized to the nucleus. Alternatively, an unlabeled molecule may be used, in combination with a labeled binding partner of the molecule. Using such an assay, it is possible to determine not only the presence of the c-Rel molecule, but also its subcellular distribution, i.e., in the nucleus. Alternatively, c-Rel can be expressed with a detectable moiety, such as a flag tag. An antibody specific for the tag then allows for detection of the recombinant c-Rel molecule.

Immunoassays for c-Rel will typically comprise incubating a sample, such as a cell in vivo or in in vitro culture, in the presence of a detectably labeled molecule specific for c-Rel, e.g., an antibody to c-Rel, and detecting the bound molecule by any of a number of techniques known in the art.

In a specific embodiment, a biological sample, e.g., freshly obtained cells, may be brought in contact with and immobilized onto a solid phase support or carrier such as nitrocellulose, glass, polystyrene, or other solid support, which is capable of immobilizing cells. The support may then be washed with suitable buffers followed by treatment with the detectably labeled molecule. The solid phase support may then be washed with the buffer a second time to remove unbound molecule. The amount of bound label on solid support may then be detected by conventional means.

The binding activity of a given antibody to a c-Rel molecule may be determined according to well-known methods. Those skilled in the art will be able to determine operative and optimal assay conditions for each determination by employing routine experimentation.

One of the ways in which an antibody to c-Rel can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1-7, Microbiological Associates Quarterly Publication, Walkersville, Md.); Voller et al., 1978, J. Clin. Pathol. 31:507-520; Butler, 1981, Meth. Enzymol. 73:482-523; Maggio, E. (ed.), 1980, Enzyme Immunoassay, CRC Press, Boca Raton, Fla.; Ishikawa et al., (eds.), 1981, Enzyme Immunoassay, Kgaku Shoin, Tokyo)). The enzyme which is bound to the antibody bound to a c-Rel molecule will react with an appropriate substrate, preferably a chromogenic substrate, in such a manner as to produce a chemical moiety which can be detected, for example, by spectrophotometric, fluorimetric or by visual means.

It is also possible to label the antibody with a fluorescent or chemiluminescent or bioluminescent compound or with a radioactive moiety or other label known in the art.

Another method of detecting and/or measuring c-Rel nuclear localization is to isolate nuclear proteins by any method known in the art and detect whether c-Rel is present in the pool of nuclear proteins, preferably by mass spectroscopy analysis to identify the proteins in the pool of nuclear proteins. Isolation of nuclear proteins can be accomplished by any method know in the art. After nuclear protein isolation, detection of c-Rel can be accomplished, e.g., by immunoprecipitating c-Rel with an anti-c-Rel antibody or binding to anti-c-Rel antibody on an immunoaffinity column or immobilized on a plate or in a well, or visualizing the protein by Western blotting. In another embodiment of the invention, c-Rel localization to the nucleus can be detected and/or measured by isolating and separating nuclear proteins on a SDS-PAGE gel, eluting separated protein from the gel, and subjecting the eluted protein to mass spectroscopy analysis to determine amino acid sequence. Such mass spectroscopy analysis can be carried out by any suitable method of mass spectroscopy known in the art, e.g., as described in Neubauer et al., 1998, Nature Genetics 20:46-50; Neubauer et al., 1997, Proc. Natl. Acad. Sci. USA 94:385-390; and Wilm et al., 1996, Nature 379:466-469. By way of example but not limitation, the eluted peptides are dissolved in a 5% methanol/5% formic acid solution and desalted using a capillary column as described in Wilm and Mann, 1996, Anal. Chem. 68:1-8. The peptides are then diluted in one step in a 50% methanol/5% formic acid solution (0.5-2 µl) directly into the spraying needle of the nanoelectrospray ion source. A mass spectrum of the peptides is acquired. The peptides are then selected in turn in the first quadrupole. This first part of the mass spectrometer is used as a mass filter, allowing the transmission of a peptide ion species of one m/z value at a time. Each peptide is then fragmented individually by collision-induced dissociation with argon in the collision cell. The resulting peptide fragment ions are separated in the third quadrupole and detected. For tryptic peptides this usually results in a 'nested set' of peptide fragments containing the carboxy-terminus. As the mass difference between two adjacent fragments corresponds with the residue masses of the corresponding amino acid, partial sequence of the peptide from its carboxy to amino terminus can be determined.

The cell in which the localization of c-Rel is detected and/or measured can be in vitro (e.g., isolated in cell culture) or in vivo. The cell in which c-Rel subcellular localization is detected can be any cell, e.g., one that endogenously or recombinantly expresses c-Rel or a fragment or homolog thereof. The cell can be vertebrate, insect (e.g., *Drosophila*), *C. elegans*, mammalian, bovine, murine, rat, avian, fish, primate, human, etc. The c-Rel which is expressed can be vertebrate, insect, *C. elegans*, mammalian, bovine, murine, rat, avian, fish, primate, human, etc. The cell can be a cell of primary tissue, a cell line, or of an animal containing and expressing a c-Rel transgene. For example, the transgenic animal can be a *Drosophila* (e.g., *melanogaster*) or a *C. elegans*. In a preferred embodiment, the transgene encodes a human c-Rel. Transgenic animals can be made by standard methods well known in the art.

In specific embodiments of the invention, antibodies and fragments containing the binding domain thereof, directed against c-Rel are used to detect c-Rel in a specific embodiment of the above methods. Accordingly, c-Rel proteins, fragments or analogs or derivatives thereof, in particular, human c-Rel protein or fragments thereof, may be used as immunogens to generate anti-c-Rel protein antibodies. Such antibodies can be polyclonal, monoclonal, chimeric, single chain, Fab fragments, or from an Fab expression library. Methods for the production of such antibodies are well known in the art, and some of which are described, infra.

The antibodies specific for c-Rel can be used in methods known in the art, and those methods discussed above, relating to the localization and/or quantification of c-Rel proteins of the invention, e.g., for imaging these proteins, measuring levels thereof in appropriate physiological samples, in diagnostic methods, etc. This hold true also for a derivative, homolog, or analog of a c-Rel protein.

The level of expression of NFκB or amount of IκB can also be determined by using any method known in the art, including the use of antibodies specific to NFκB family members or any subunit thereof, e.g., p50, p65 or c-Rel or to IκB. For example, using an antibody specific for IκB, the amount of IκB can be determined, for example, by the illustrative method taught in the Examples Section, infra. The levels of expression of NFκB can be determined by measuring the amount of p50, p65 or c-Rel.

Other methods for detection of whether c-Rel is located in the nucleus can include measuring for the presence of proteins, or their encoding mRNA molecules, that are dependent on c-Rel for transcriptional activation and whether there is an increase (increased c-Rel in nucleus) or a decrease in expression (decreased c-Rel in the nucleus).

Antibody Production

Various procedures known in the art may be used for the production of antibodies to c-Rel, NFκB family members or any subunit thereof, or IκB, or a fragment, derivative, homolog or analog of the protein. Antibodies of the invention include, but are not limited to, synthetic antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv) (including bi-specific scFvs), single chain antibodies Fab fragments, F(ab') fragments, disulfide-linked Fvs (sdFv), and anti-idiotypic (anti-Id) antibodies, and epitope-binding fragments of any of the above. In particular, antibodies of the present invention include immunoglobulin molecules and immunologically active portions of immunoglobulin molecules, i.e., molecules that contain an antigen binding site that immunospecifically binds to an antigen (e.g., one or more complementarily determining regions (CDRs) of an antibody).

For production of the antibody, various host animals can be immunized by injection with, e.g., a native c-Rel protein or a synthetic version, or a derivative of the foregoing. Such host animals include, but are not limited to, rabbits, mice, rats, etc. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacille Calmette-Guerin (BCG) and *Corynebacterium parvum*. Although the following refers specifically to c-Rel, any of the methods described herein apply equally to c-Rel, NFκB family members or subunits thereof, or IκB.

For preparation of monoclonal antibodies directed towards c-Rel or a derivative, fragment, homolog or analog thereof, any technique that provides for the production of antibody molecules by continuous cell lines in culture may be used. Such techniques include, but are not restricted to, the hybridoma technique originally developed by Kohler and Milstein (1975, Nature 256:495-497), the trioma technique (Gustafsson et al., 1991, Hum. Antibodies Hybridomas 2:26-32), the human B-cell hybridoma technique (Kozbor et al., 1983, Immunology Today 4:72), and the EBV hybridoma technique to produce human monoclonal antibodies (Cole et al., 1985, In: Monoclonal Antibodies and Cancer Therapy, Alan R. Liss, Inc., pp. 77-96). In an additional embodiment of the invention, monoclonal antibodies can be produced in germ-free animals utilizing recent technology described in International Patent Application PCT/US90/02545.

According to the present invention, human antibodies may be used and can be obtained by using human hybridomas (Cote et al., 1983, Proc. Natl. Acad. Sci. USA 80:2026-2030) or by transforming human B cells with EBV virus in vitro (Cole et al., 1985, In: Monoclonal Antibodies and Cancer Therapy, Alan R. Liss, Inc., pp. 77-96). In fact, according to the invention, techniques developed for the production of "chimeric antibodies" (Morrison et al., 1984, Proc. Natl. Acad. Sci. USA 81:6851-6855; Neuberger et al., 1984, Nature 312:604-608; Takeda et al., 1985, Nature 314:452-454) by splicing the genes from a mouse antibody molecule specific for c-Rel together with genes from a human antibody molecule of appropriate biological activity can be used; such antibodies are within the scope of this invention.

According to the present invention, techniques described for the production of single chain antibodies (U.S. Pat. No. 4,946,778) can be adapted to produce c-Rel-specific antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for c-Rel proteins, derivatives, or analogs thereof. Non-human antibodies can be "humanized" by known methods (e.g., U.S. Pat. No. 5,225,539).

Antibody fragments that contain the idiotypes of c-Rel can be generated by techniques known in the art. For example, such fragments include, but are not limited to, the F(ab')2 fragment which can be produced by pepsin digestion of the antibody molecule; the Fab' fragment that can be generated by reducing the disulfide bridges of the F(ab')2 fragment; the Fab fragment that can be generated by treating the antibody molecular with papain and a reducing agent; and Fv fragments. Synthetic antibodies, e.g., antibodies produced by chemical synthesis, are useful in the present invention.

In the production of antibodies, screening for the desired antibody can be accomplished by techniques known in the art, e.g., ELISA (enzyme-linked immunosorbent assay). To select antibodies specific to a particular domain of c-Rel, or a derivative, homolog, or analog thereof, one may assay generated hybridomas for a product that binds to the fragment of the c-Rel protein, or a derivative, homolog, or analog thereof, that contains such a domain.

Recombinant Expression

Methods for recombinant production of c-Rel and derivatives or fragments or homologs thereof for use in the screening methods of the present invention are well known to those skilled in the art. Nucleic acids encoding c-Rel, derivatives, fragments, and homologs thereof are known in the art. The nucleotide sequence encoding an illustrative human c-Rel molecule is known and is provided in FIG. 1 (SEQ ID NO:1). Nucleic acids encoding c-Rel can be obtained by any method known in the art, e.g., by PCR amplification using synthetic primers hybridizable to the 3' and 5' ends of each sequence, and/or by cloning from a cDNA or genomic library using an oligonucleotide specific for each nucleotide sequence.

Homologs (e.g., nucleic acids encoding c-Rel of species other than human) or other related sequences (e.g., paralogs) can be obtained by low, moderate or high stringency hybridization with all or a portion of the particular human sequence as a probe, using methods well known in the art for nucleic acid hybridization and cloning.

The encoded c-Rel protein, which is depicted in FIG. 1 (SEQ ID NO:2) can be obtained by methods well known in the art fir protein purification and recombinant protein expression. For recombinant expression of one or more of the proteins, the nucleic acid containing all or a portion of the nucleotide sequence encoding the protein can be inserted into an appropriate expression vector, i.e., a vector that contains the necessary elements for the transcription and translation of the inserted protein coding sequence. The necessary transcriptional and translational signals can also be supplied by the native promoter of the c-Rel gene, and/or their flanking regions.

A variety of host-vector systems may be utilized to express the protein coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

In a preferred embodiment, human c-Rel is obtained by expressing the human c-Rel coding sequence. In yet another embodiment, a derivative, fragment or homolog of c-Rel is recombinantly expressed. In one embodiment, the c-Rel protein is expressed as chimeric or fusion protein in which an amino acid sequence different from the c-Rel sequence is linked via a peptide bond to the c-Rel sequence. The different amino acid sequence can be a tag, such as a flag tag, for detection and isolation of the expressed chimeric or fusion protein.

Any method available in the art can be used for the insertion of DNA fragments into a vector to construct expression vectors containing a chimeric gene consisting of appropriate transcriptional/translational control signals and protein coding sequences. These methods may include in vitro recombinant DNA and synthetic techniques and in vivo recombinant techniques (genetic recombination). Expression of nucleic acid sequences encoding c-Rel, or a derivative, fragment or homolog thereof, may be regulated by a second nucleic acid sequence so that the gene or fragment thereof is expressed in a host transformed with the recombinant DNA molecule(s). For example, expression of the proteins may be controlled by any promoter/enhancer known in the art. In a specific embodiment, the promoter is not native to the gene for c-Rel. In another specific embodiment, the promoter is active in immune cells, e.g., peripheral blood mononuclear cells, dendritic cells or monocytes or splenocytes. Promoters that may be used include but are not limited to the SV40 early promoter (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. USA 78:1441-1445), the regulatory sequences of the metallothionein gene (Brinster et al., 1982, Nature 296:39-42); prokaryotic expression vectors such as the β-lactamase promoter (Villa-Kamaroff et al., 1978, Proc. Natl. Acad. Sci. USA 75:3727-3731) or the tac promoter (DeBoer et al., 1983, Proc. Natl. Acad. Sci. USA 80:21-25; Gilbert et al., 1980, Scientific American 242:79-94); plant expression vectors comprising the nopaline synthetase promoter (Herrar-Estrella et al., 1984, Nature 303:209-213) or the cauliflower mosaic virus 35S RNA promoter (Garder et al., 1981, Nucleic Acids Res. 9:2871), and the promoter of the photosynthetic enzyme ribulose bisphosphate carboxylase (Herrera-Estrella et al., 1984, Nature 310:115-120); promoter elements from yeast and other fungi such as the Gal4 promoter (Johnston et al., 1987, Microbiol. Rev. 51:458-476), the alcohol dehydrogenase promoter (Schibler et al., 1987, Annual Review Genetics 21:237-257), the phosphoglycerol kinase promoter (Struhl et al., 1995, Annual Review Genetics 29:651-674-257; Guarente 1987, Annual Review Genetics 21:425-452), the alkaline phosphatase promoter (Struhl et al., 1995, Annual Review Genetics 29:651-674-257; Guarente 1987, Annual Review Genetics 21:425-452), and the following animal transcriptional control regions that exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald 1987, Hepatology 7:425-515); insulin gene control region which is active in pancreatic beta cells (Hanahan et al., 1985, Nature 315:115-122), immunoglobulin gene control region which is active in lymphoid cells (Grosschedl et al., 1984, Cell 38:647-658; Adams et al., 1985, Nature 318:533-538; Alexander et al., 1987, Mol. Cell Biol. 7:1436-1444), mouse mammary tumor virus control region which is active in testicular, breast, lymphoid and mast cells (Leder et al., 1986, Cell 45:485-495), albumin gene control region which is active in liver (Pinckert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58), alpha-1 antitrypsin gene control region which is active in liver (Kelsey et al., 1987, Genes and Devel. 1:161-171), beta globin gene control region which is active in myeloid cells (Mogram et al., 1985, Nature 315:338-340; Kollias et al., 1986, Cell 46:89-94), myelin basic protein gene control region which is active in oligodendrocyte cells of the brain (Readhead et al., 1987, Cell 48:703-712), myosin light chain-2 gene control region which is active in skeletal muscle (Sani 1985, Nature 314:283-286), and gonadotrophic releasing hormone gene control region which is active in gonadotrophs of the hypothalamus (Mason et al., 1986, Science 234:1372-1378).

In a specific embodiment, a vector is used that comprises a promoter operably linked to the nucleic acid sequence encoding c-Rel, or a fragment, derivative or homo log thereof, one or more origins of replication, and optionally, one or more selectable markers (e.g., an antibiotic resistance gene).

In another specific embodiment, an expression vector containing the coding sequence, or a portion thereof, of c-Rel is made by subcloning the gene sequence into the EcoRI restriction site of each of the three pGEX vectors (glutathione S-transferase expression vectors; Smith and Johnson, 1988, Gene 7:31-40). This allows for the expression of products in the correct reading frame.

Expression vectors containing the sequences of interest can be identified by three general approaches: (a) nucleic acid hybridization, (b) presence or absence of "marker" gene function, and (c) expression of the inserted sequences. In the first approach, c-Rel sequences can be detected by nucleic acid hybridization to probes comprising sequences homologous and complementary to the inserted sequences. In the second approach, the recombinant vector/host system can be identified and selected based upon the presence or absence of certain "marker" functions (e.g., resistance to antibiotics, occlusion body formation in baculovirus, etc.) caused by insertion of the sequences of interest in the vector. For example, if a c-Rel gene, or portion thereof, is inserted within the marker gene sequence of the vector, recombinants containing the c-Rel fragment will be identified by the absence of the marker gene function (e.g., loss of beta-galactosidase activity). In the third approach, recombinant expression vectors can be identified by assaying for the c-Rel expressed by the recombinant vector.

Once recombinant c-Rel molecules are identified and isolated, several methods known in the art can be used to propagate them. Using a suitable host system and growth conditions, recombinant expression vectors can be propagated and amplified in quantity. As previously described, the expression vectors or derivatives which can be used include, but are not limited to, human or animal viruses such as vaccinia virus or adenovirus; insect viruses such as baculovirus, yeast vectors; bacteriophage vectors such as lambda phage; and plasmid and cosmid vectors.

In addition, a host cell strain may be chosen that modulates the expression of the inserted sequences, or modifies or processes the expressed proteins in the specific fashion desired. Expression from certain promoters can be elevated in the presence of certain inducers; thus expression of the genetically-engineered c-Rel may be controlled. Furthermore, different host cells have characteristic and specific mechanisms for the translational and post-translational processing and modification (e.g., glycosylation, phosphorylation, etc.) of proteins. Appropriate cell lines or host systems can be chosen to ensure that the desired modification and processing of the foreign protein is achieved. For example, expression in a bacterial system can be used to produce an unglycosylated core protein, while expression in mammalian cells ensures "native" glycosylation of a heterologous protein. Furthermore, different vector/host expression systems may effect processing reactions to different extents.

In other specific embodiments, the c-Rel protein or a fragment, homolog or derivative thereof, may be expressed as fusion or chimeric protein products comprising the protein, fragment, homolog, or derivative joined via a peptide bond to a heterologous protein sequence of a different protein. Such chimeric products can be made by ligating the appropriate nucleic acid sequences encoding the desired amino acids to each other by methods known in the art, in the proper coding frame, and expressing the chimeric products in a suitable host by methods commonly known in the art.

Screening Methods for Identifying Modulators

In one embodiment of the invention, methods are provided for the identification of modulators, e.g., inhibitors, antagonists, or agonists, of c-Rel activity by detecting the ability of candidate molecules to effect an alteration of c-Rel subcellular localization (qualitatively and/or quantitatively), without materially altering the level of expression of NFkB and/or amount of IκB, and, thus, perhaps its activity in activating transcription of a gene where c-Rel plays a role in creating the transcriptional initiation complex by forming a sequence-specific DNA binding complex at a NFκB binding site in the promoter and/or enhancer of the gene. An illustrative example of such genes are c-Rel-dependent cytokines, e.g., IL-12 and IL-23 whose subunits p40 and p35 each contain an NFκB site in its promoter. In one aspect of this embodiment of the invention, the method for identifying a modulator of c-Rel activity comprises providing a cell with a candidate modulator molecule and detecting or measuring the amount of c-Rel that co-purifies or co-localizes with the nucleus without materially altering the levels of expression NFκB or amount of IκB, wherein a difference in the presence or amount of c-Rel co-purifying or co-localizing to the nucleus compared to a cell not contacted with the candidate molecule indicates that the candidate molecule modulates c-Rel activity. Exemplary cells and cell lines useful in the screening methods of the present invention include, but are not limited to, macrophages, dendritic cells, monocytes, peripheral blood mononuclear cells, which preferably are stimulated with IFN-γ and/or LPS prior to contacting with the candidate molecule.

A particular aspect of the present invention relates to identifying molecules that inhibit or promote c-Rel localization to the nucleus. In another particular aspect related to identifying molecules that inhibit or promote c-Rel localization to the nucleus without affecting the overall amount of c-Rel expressed in the cell, either on the transcriptional or translational level. In a preferred aspect, molecules are identified that reduce the amount of c-Rel in the nucleus by, e.g., inhibiting translocation of c-Rel into the nucleus or increasing the rate of degradation of c-Rel in the nucleus. In other aspects, the amount of c-Rel in the nucleus or c-Rel translocation to the nucleus is inhibited but the amount of NFκB family member p65 increases in the nucleus. In yet another aspect, c-Rel translocation to the nucleus is inhibited and the amount of ICSBP is also reduced, with or without affecting the levels of ICSBP mRNA or protein. In yet another aspect, c-Rel translocation to the nucleus is reduced and the Ets-2 binding domain in the promoter of p40 no longer has the ability to activate transcription as compared to a cell Where the amount of c-Rel in the nucleus is not reduced.

Methods that can be used to carry out the foregoing are commonly known in the art and/or those methods disclosed in Section 5.1, supra. The cells used in the methods of this embodiment of the invention can either endogenously or recombinantly express c-Rel, or a fragment, derivative or analog thereof. Recombinant expression of c-Rel is carried out by introducing c-Rel encoding nucleic acids into expression vectors and subsequently introducing the vectors into a cell to express c-Rel or simply introducing c-Rel encoding nucleic acids into a cell for expression, as described in Section 5.1.1 or using procedures well known in the art. In a specific embodiment, c-Rel is expressed with a tag for ease of detection but where the tag has no effect on c-Rel activity or subcellular localization. Nucleic acids encoding c-Rel from a number of species have been cloned and sequenced and their expression is well known in the art. An illustrative example of a human c-Rel nucleotide and amino acid sequence is set forth in FIG. 1 (SEQ ID NOS:1 and 2). Expression can be from expression vectors or intrachromosomal. In a specific embodiment, standard human cell lines, such as human dendritic cell lines or the human monocyte cell line THP-1, or human peripheral blood mononuclear cells, are employed in the screening assays. In specific aspects, when immune cells are employed, the immune cells are contacted with immunoactivating compounds such as lipopolysaccharide (LPS) or interferon-γ (IFN-γ), before, concurrently or after contacting with the one or more candidate molecules.

Any method known to those of skill in the art for the insertion of c-Rel-encoding DNA into a vector may be used to construct expression vectors for expressing c-Rel, including those methods described in Section 5.1, supra. In addition, a host cell strain may be chosen which modulates the expression of c-Rel, or modifies and processes the gene product in the specific fashion desired. Expression from certain promoters can be elevated in the presence of certain inducers; thus, expression of c-Rel protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the c-Rel protein expressed. Illustrative cell lines are those described in the Examples section, infra.

In another embodiment of the invention, methods are provided for identifying a drug target for mediating selective inhibition of c-Rel activity. One such illustrative method comprises the following steps in the order stated: (a) labeling one or more agents that reduce the amount of c-Rel in the nucleus of the cell without materially altering the level of expression of NFκB or amount of IκB; (b) contacting the cell with the one or more labeled agents under conditions that form a complex between the one or more labeled agents and the drug target; (c) isolating the complex; and (d) identifying the drug target from the complex.

Candidate Molecules

Any molecule known in the art can be tested for its ability to modulate (increase or decrease) c-Rel activity as detected by a change in the subcellular localization of c-Rel (or amount thereof). By way of example, a change in the localization can be detected by detecting a change in the amount of c-Rel that purifies with or localizes to the nucleus before and alter exposure to the candidate molecules. For identifying a molecule that modulates c-Rel activity, candidate molecules can be directly provided to a cell expressing c-Rel, or, in the case of candidate proteins, can be provided by providing their encoding nucleic acids under conditions in which the nucleic acids are recombinantly expressed to produce the candidate proteins within the c-Rel expressing cell.

Preferred compounds that inhibit translocation of c-Rel to the nucleus but do not materially alter expression of NFκB and/or the amount of IκB include the following compounds:

Compound 1: N-(1H-indol-3-ylmethylene)-N'-[4-morpholin-4-yl-6-(2-pyridin-2-yl-ethoxy)-[1,3,5]triazin-2-yl]-hydrazine;

Compound 2: N-(3-methyl-benzylidene)-N'-[6-morpholin-4-yl-2-(2-pyridin-2-yl-ethoxy)-pyrimidin-4-yl]-hydrazine;

Compound 3: N-(1H-indol-3-ylmethylene)-N'-[4-morpholin-4-yl-6-(2-morpholin-4-yl-ethoxy)-pyridin-2-yl]-hydrazine Compound 4: N-[3,5-Difluoro-2-morpholin-4-yl-6-(2-morpholin-4-yl-ethoxy)-pyridin-4-yl]-N'-(3-methyl-benzylidene)-hydrazine;

Compound 5: N-(3-methyl-benzylidene)-N'-[4-morpholin-4-yl-6-(2-morpholin-4-yl-ethoxy)-pyridin-2-yl]-hydrazine;

Compound 6: N-methyl-N'-(3-methyl-benzylidene)-N-[4-morpholin-4-yl-6-(2-morpholin-4-yl-ethoxy)-pyridin-2-yl]-hydrazine;

Compound 7: 4-methyl-2-{[4-morpholin-4-yl-6-(2-morpholin-4-yl-ethoxy)-pyridin-2-yl]-hydrazononomethyl}-phenylamine;

Compound 8: N-(6,7-dimethoxy-2-morpholin-4-yl-quinolin-4-yl)-N'-(3-methyl-benzylidene)-hydrazine;

Compound 9: N-7-Chloro-2-morpholin-4-yl-quninazolin-4-yl)-N'-(3-methyl-benzylidene)-hydrazine;

Compound 10: N-[7-methoxy-2-morpholin-4-yl-6-(2-phenoxy-ethoxy)-quinazolin-4-yl]-N'-(3-methyl-benzylidene)-hydrazine;

Compound 11: N-[6-Morpholin-4-yl-2-(2-pyridin-2-yl-ethoxy)-pyrimidin-4-ylmethylene]-N'-m-tolyl-hydrazine;

Compound 12: N-(3-Chloro-phenyl)-N'-[6-morpholin-4-yl-2-(2-pyridin-2-yl-ethoxy)-pyrimidin-4-ylmethylene]-hydrazine;

Compound 13: N-(3-Methoxy-phenyl)-N'-[6-morpholin-4-yl-2-(2-pyridin-2-yl-ethoxy)-pyrimidin-4-ylmethylene]-hydrazine; and Compound 14: N-(2,5-Dimethyl-phenyl)-N'-[6-morpholin-4-yl-2-(2-pyridin-2-yl-ethoxy)-pyrimidin-4-ylmethylene]-hydrazine.

This embodiment of the invention is well suited to screen chemical libraries for molecules which modulate, e.g., inhibit, antagonize, or agonize, c-Rel activity by altering the amount of c-Rel that purifies with or localizes to the nucleus. The chemical libraries can be peptide libraries, peptidomimetic libraries, chemically synthesized libraries, recombinant, e.g., phage display libraries, and in vitro translation-based libraries, other non-peptide synthetic organic libraries, etc.

Libraries screened using the methods of the present invention can comprise a variety of types of compounds. Examples of libraries that can be screened in accordance with the methods of the invention include, but are not limited to, peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small molecule libraries (preferably, small organic molecule libraries). In some embodiments, the compounds in the libraries screened are nucleic acid or peptide molecules. In a non-limiting example, peptide molecules can exist in a phage display library. In other embodiments, the types of compounds include, but are not limited to, peptide analogs including peptides comprising non-naturally occurring amino acids, e.g., D-amino acids, phosphorous analogs of amino acids, such as γ-amino phosphoric acids and γ-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used in the assays of the invention.

In a preferred embodiment, the combinatorial libraries are small organic molecule libraries including, but not limited to, benzodiazepines, isoprenoids, thiazolidinones, metathiazanones, pyrrolidines, morpholino compounds, and benzodiazepines. In another embodiment, the combinatorial libraries comprise peptoids; random bio-oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available (see, e.g., ComGenex, Princeton, N.J.; Asinex, Moscow, Ru, Tripos, Inc., St. Louis, Mo.; ChemStar, Ltd, Moscow, Russia; 3D Pharmaceuticals, Exton, Pa.; Martek Biosciences, Columbia, Md.; etc.).

In a preferred embodiment, the library is preselected so that the compounds of the library are more amenable for cellular uptake. For example, compounds are selected based on specific parameters such as, but not limited to, size, lipophilicity, hydrophilicity, and hydrogen bonding, which enhance the likelihood of compounds getting into the cells. In another embodiment, the compounds are analyzed by three-dimensional or four-dimensional computer computation programs.

The combinatorial compound library for use in accordance with the methods of the present invention may be synthesized. There is a great interest in synthetic methods directed toward the creation of large collections of small organic compounds, or libraries, which could be screened for pharmacological, biological or other activity. The synthetic methods applied to create vast combinatorial libraries are performed in solution or in the solid phase, i.e., on a solid support. Solid-phase synthesis makes it easier to conduct multi-step reactions and to drive reactions to completion with high yields because excess reagents can be easily added and washed away after each reaction step. Solid-phase combinatorial synthesis also tends to improve isolation, purification and screening. However, the more traditional solution phase chemistry supports a wider variety of organic reactions than solid-phase chemistry.

Combinatorial compound libraries of the present invention may be synthesized using the apparatus described in U.S. Pat. No. 6,190,619 to Kilcoin et al., which is hereby incorporated by reference in its entirety. U.S. Pat. No. 6,190,619 discloses a synthesis apparatus capable of holding a plurality of reaction vessels for parallel synthesis of multiple discrete compounds or for combinatorial libraries of compounds.

In one embodiment, the combinatorial compound library can be synthesized in solution. The method disclosed in U.S. Pat. No. 6,194,612 to Boger et al., which is hereby incorporated by reference in its entirety, features compounds useful as templates for solution phase synthesis of combinatorial libraries. The template is designed to permit reaction products to be easily purified from unreacted reactants using liquid/liquid or solid/liquid extractions. The compounds produced by combinatorial synthesis using the template will preferably be small organic molecules. Some compounds in the library may mimic the effects of non-peptides or peptides. In contrast to solid phase synthesize of combinatorial compound libraries, liquid phase synthesis does not require the use of specialized protocols for monitoring the individual steps of a multistep solid phase synthesis (Egner et al., 1995, J. Org. Chem, 60:2652; Anderson et al., 1995, J. Org. Chem. 60:2650; Fitch et al., 1994, J. Org. Chem. 59:7955; Look et al., 1994, J. Org. Chem. 49:7588; Metzger et al., 1993, Angew. Chem., Int. Ed. Engl. 32:894; Youngquist et al., 1994, Rapid Commun. Mass Spect. 8:77; Chu et al., 1995, J. Am. Chem. Soc. 117:5419; Brummel et al., 1994, Science 264:399; and Stevanovic et al., 1993, Bioorg. Med. Chem. Lett. 3:431).

Combinatorial compound libraries useful for the methods of the present invention can be synthesized on solid supports. In one embodiment, a split synthesis method, a protocol of separating and mixing solid supports during the synthesis, is used to synthesize a library of compounds on solid supports (see e.g., Lam et al., 1997, Chem. Rev. 97:41-448; Ohlmeyer et al., 1993, Proc. Natl. Acad. Sci.

USA 90:10922-10926 and references cited therein). Each solid support in the final library has substantially one type of compound attached to its surface. Other methods for synthesizing combinatorial libraries on solid supports, wherein one product is attached to each support, will be known to those of skill in the art (see, e.g., Nefzi et al., 1997, Chem. Rev. 97:449-472).

As used herein, the term "solid support" is not limited to a specific type of solid support. Rather a large number of supports are available and are known to one skilled in the art. Solid supports include silica gels, resins, derivatized plastic films, glass beads, cotton, plastic beads, polystyrene beads, alumina gels, and polysaccharides. A suitable solid support may be selected on the basis of desired end use and suitability for various synthetic protocols. For example, for peptide synthesis, a solid support can be a resin such as p-methylbenzhydrylamine (pMBHA) resin (Peptides International, Louisville, Ky.), polystyrenes (e.g., PAM-resin obtained from Bachem Inc., Peninsula Laboratories, etc.), including chloromethylpolystyrene, hydroxymethylpolystyrene and aminomethylpolystyrene, poly (dimethylacrylamide)-grafted styrene co-divinyl-benzene (e.g., POLYHIPE resin, obtained from Aminotech, Canada), polyamide resin (obtained from Peninsula Laboratories, etc.), polystyrene resin grafted with polyethylene glycol (e.g., TENTAGEL or ARGOGEL, Bayer, Tubingen, Germany) polydimethylacrylamide resin (obtained from Milligen/Biosearch, California), or Sepharose (Pharmacia, Sweden).

In some embodiments of the present invention, compounds can be attached to solid supports via linkers. Linkers can be integral and part of the solid support, or they may be nonintegral that are either synthesized on the solid support or attached thereto after synthesis. Linkers are useful not only for providing points of compound attachment to the solid support, but also for allowing different groups of molecules to be cleaved from the solid support under different conditions, depending on the nature of the linker. For example, linkers can be, inter alia, electrophilically cleaved, nucleophilically cleaved, photocleavable, enzymatically cleaved, cleaved by metals, cleaved under reductive conditions or cleaved under oxidative conditions. In a preferred embodiment, the compounds are cleaved from the solid support prior to high throughput screening of the compounds.

In certain embodiments of the invention, the compound is a small molecule.

Exemplary libraries are commercially available from several sources (ArQule, Tripos/PanLabs, ChemDesign, Pharmacopoeia). In some cases, these chemical libraries are generated using combinatorial strategies that encode the identity of each member of the library on a substrate to which the member compound is attached, thus allowing direct and immediate identification of a molecule that is an effective modulator. Thus, in many combinatorial approaches, the position on a plate of a compound specifies that compound's composition. Also, in one example, a single plate position may have from 1-20 chemicals that can be screened by administration to a well containing the interactions of interest. Thus, if modulation is detected, smaller and smaller pools of interacting pairs can be assayed for the modulation activity. By such methods, many candidate molecules can be screened.

Many diversity libraries suitable for use are known in the art and can be used to provide compounds to be tested according to the present invention. Alternatively, libraries can be constructed using standard methods. Chemical (synthetic) libraries, recombinant expression libraries, or polysome-based libraries are exemplary types of libraries that can be used.

The libraries can be constrained or semirigid (having some degree of structural rigidity), or linear or nonconstrained. The library can be a cDNA or genomic expression library, random peptide expression library or a chemically synthesized random peptide library, or non-peptide library. Expression libraries are introduced into the cells in which the assay occurs, where the nucleic acids of the library are expressed to produce their encoded proteins.

In one embodiment, peptide libraries that can be used in the present invention may be libraries that are chemically synthesized in vitro. Examples of such libraries are given in Houghten et al., 1991, Nature 354:84-86, which describes mixtures of free hexapeptides in which the first and second residues in each peptide were individually and specifically defined; Lam et al., 1991, Nature 354:82-84, which describes a "one bead, one peptide" approach in which a solid phase split synthesis scheme produced a library of peptides in which each bead in the collection had immobilized thereon a single, random sequence of amino acid residues; Medynski, 1994, Bio/Technology 12:709-710, which describes split synthesis and T-bag synthesis methods; and Gallop et al., 1994, J. Medicinal Chemistry 37(9): 1233-1251. Simply by way of other examples, a combinatorial library may be prepared for use, according to the methods of Ohlmeyer et al., 1993, Proc. Natl. Acad. Sci. USA 90:10922-10926; Erb et al., 1994, Proc. Natl. Acad. Sci. USA 91:11422-11426; Houghten et al., 1992, Biotechniques 13:412; Jayawickreme et al., 1994, Proc. Natl. Acad. Sci. USA 91:1614-1618; or Salmon et al., 1993, Proc. Natl. Acad. Sci. USA 90:11708-11712. PCT Publication No. WO 93/20242 and Brenner and Lerner, 1992, Proc. Natl. Acad. Sci. USA 89:5381-5383 describe "encoded combinatorial chemical libraries," that contain oligonucleotide identifiers for each chemical polymer library member.

In a preferred embodiment, the library screened is a biological expression library that is a random peptide phage display library; where the random peptides are constrained (e.g., by virtue of having disulfide bonding).

Further, more general, structurally constrained, organic diversity (e.g., nonpeptide) libraries, can also be used. By way of example, a benzodiazepine library (see e.g., Bunin et al., 1994, Proc. Natl. Acad. Sci. USA 91:4708-4712) may be used.

Conformationally constrained libraries that can be used include but are not limited to those containing invariant cysteine residues which, in an oxidizing environment, cross-link by disulfide bonds to form cystines, modified peptides (e.g., incorporating fluorine, metals, isotopic labels, are phosphorylated, etc.), peptides containing one or more non-naturally occurring amino acids, non-peptide structures, and peptides containing a significant fraction of γ-carboxyglutamic acid.

Libraries of non-peptides, e.g., peptide derivatives (for example, that contain one or more non-naturally occurring amino acids) can also be used. One example of these is peptide libraries (Simon et al., 1992, Proc. Natl. Acad. Sci. USA 89:9367-9371). Peptoids are polymers of non-natural amino acids that have naturally occurring side chains attached not to the alpha carbon but to the backbone amino nitrogen. Since peptoids are not easily degraded by human digestive enzymes, they are advantageously more easily adaptable to drug use. Another example of a library that can be used, in which the amide functionalities in peptides have been premethylated to generate a chemically transformed combinatorial library, is described by Ostresh et al., 1994, Proc. Natl. Acad. Sci. USA 91:11138-11142).

The members of the peptide libraries that can be screened according to the invention are not limited to containing the 20 naturally occurring amino acids. In particular, chemically synthesized libraries and polysome based libraries allow the use of amino acids in addition to the 20 naturally occurring amino acids (by their inclusion in the precursor pool of amino acids used in library production). In specific embodiments, the library members contain one or more non-natural or non-classical amino acids or cyclic peptides. Non-classical amino acids include but are not limited to the D-isomers of the common amino acids, α-amino isobutyric acid, 4-aminobutyric acid, Abu, 2-amino butyric acid; γ-Abu, ε-Ahx, 6-amino hexanoic acid; Aib, 2-amino isobutyric acid; 3-amino propionic acid; ornithine; norleucine; norvaline, hydroxyproline, sarcosine, citrulline, cysteic acid, t-butylglycine, t-butylalanine, phenylglycine, cyclohexylalanine, β-alanine, designer amino acids such as β-methyl amino acids, Ca-methyl amino acids, Nα-methyl amino acids, fluoro-amino acids and amino acid analogs in general. Furthermore, the amino acid can be D (dextrorotary) or L (levorotary).

In a specific embodiment, fragments and/or analogs of c-Rel, especially peptidomimetics, are screened for activity as competitive or non-competitive inhibitors of c-Rel nuclear localization or transport.

En another embodiment of the present invention, combinatorial chemistry can be used to identify modulators of c-Rel nuclear localization or transport. Combinatorial chemistry is capable of creating libraries containing hundreds of thousands of compounds, many of which may be structurally similar. While high throughput screening programs are capable of screening these vast libraries for affinity for known targets, new approaches have been developed that achieve libraries of smaller dimension but which provide maximum chemical diversity. (See e.g., Matter, 1997, Journal of Medicinal Chemistry 40:1219-1229).

One method of combinatorial chemistry, affinity fingerprinting, has previously been used to test a discrete library of small molecules for binding affinities for a defined panel of proteins. The fingerprints obtained by the screen are used to predict the affinity of the individual library members for other proteins or receptors of interest (in the instant invention, c-Rel.) The fingerprints are compared with fingerprints obtained from other compounds known to react with the protein of interest to predict whether the library compound might similarly react. For example, rather than testing every ligand in a large library for interaction with c-Rel, those ligands having a fingerprint similar to other compounds known to have that activity could be tested. (See, e.g., Kauvar et al., 1995, Chemistry and Biology 2:107-118; Kauvar, 1995, Affinity fingerprinting, Pharmaceutical Manufacturing International. 8:25-28; and Kauvar, Toxic-Chemical Detection by Pattern Recognition in New Frontiers in Agrochemical Immunoassay, D. Kurtz. L. Stanker and J. H. Skerritt. Editors, 1995, AOAC: Washington, D.C., 305-312).

Kay et al., 1993, Gene 128:59-65 (Kay) discloses a method of constructing peptide libraries that encode peptides of totally random sequence that are longer than those of any prior conventional libraries. The libraries disclosed in Kay encode totally synthetic random peptides of greater than about 20 amino acids in length. Such libraries can be advantageously screened to identify c-Rel modulators. (See also U.S. Pat. No. 5,498,538 dated Mar. 12, 1996; and PCT Publication No. WO 94/18318 dated Aug. 18, 1994).

Other libraries can include antibody libraries and libraries of intrabodies expressed in the cell.

If the library comprises arrays or microarrays of compounds, wherein each compound has an address or identifier, the compound can be deconvoluted, e.g., by cross-referencing the positive sample to original compound list that was applied to the individual test assays.

If the library is a peptide or nucleic acid library, the sequence of the compound can be determined by direct sequencing of the peptide or nucleic acid. Such methods are well known to one of skill in the art.

A comprehensive review of various types of peptide libraries can be found in Gallop et al., 1994, J. Med. Chem. 37:1233-1251.

Compounds Identified in Screening Assays

The present invention is further directed to the compounds identified by the above-described screening assays and to processes for producing such agents by use of these assays. The compounds can include, but are not limited to, nucleic acids, antisense nucleic acids, ribozyme, triple helix, antibody, and polypeptide molecules and small inorganic or organic molecules. Accordingly, in one embodiment, the present invention includes a compound obtained by a method comprising the steps of any one of the aforementioned screening assays. For example, the compound is obtained by a method comprising contacting a cell with one or more candidate molecules; and detecting localization of c-Rel molecules in the cell, wherein an increase or decrease in the amount of c-Rel in the nucleus without materially altering the level of expression of NFκB and/or amount of IκB relative to said amount in a cell not so contacted with the one or more candidate molecules.

Once a test compound has been identified as having an appropriate activity according to the screening methods of the present invention, the test compound can be subject to further testing, for example, in animal models to confirm its activity as a modulator of c-Rel activity or subcellular localization in the animal, or for potential side effects. The test compound can also be tested against known compounds that modulate c-Rel activity or subcellular localization, in both cell based or animal assays, to confirm its desired activity. The identified compound can also be tested to determine its toxicity, or side effects that could be associated with administration of such compound. Alternatively, a compound identified as described herein can be used in an animal model to determine the mechanism of action of such a compound.

Such exemplary evaluation methods for evaluating the biological effect of an agent that reduces the amount of c-Rel in the nucleus of a cell without materially altering the level of expression of NFκB and/or amount of IκB in the cell comprise contacting the cell with the agent and observing any phenotypic effects in the cell. Another illustrative method comprises administering the agent to a test subject/animal and observing any phenotypic effects in the test subject/animal.

The present invention also pertains to uses of compounds identified by the above-described screening assays for methods of treatment as described herein. Accordingly, it is within the scope of the present invention to use such compounds in the design, formulation, synthesis, manufacture, and/or production of a drug or pharmaceutical composition for use in diagnosis, prognosis, or treatment, as described herein. For example, in one embodiment, the present invention includes a method of synthesizing or producing a drug or pharmaceutical composition by reference to the structure and/or properties of a compound obtainable by one of the above-described screening assays. For example, a drug or pharmaceutical composition can be synthesized based on the structure and/or properties of a compound obtained by the screening methods described supra.

Furthermore, the identified compound, prior to formulation for use in a method for treatment or prophylaxis can be modified using methods known in the art to render the compound more stable, i.e., increase its half-life in the subject, or render the compound more readily absorbed into the tissues of the subject. Such modifications include, but are not limited to, PEGylation, multimerization. Such modifications are performed by a pharmaceutical chemist to make the compound more suitable for administration. Additionally, the identified compound can be modified to allow for passage across the blood-brain barrier.

The compounds which display the desired biological activity can be used as lead compounds for the development or design of congeners or analogs having useful pharmacological activity. For example, once a lead compound is identified, molecular modeling techniques can be used to design variants of the compound that can be more effective. Examples of molecular modeling systems are the CHARM and QUANTA programs (Polygen Corporation, Waltham, Mass.), CHARM performs the energy minimization and molecular dynamics functions. QUANTA performs the construction, graphic modeling and analysis of molecular structure. QUANTA allows interactive construction, modification, visualization, and analysis of the behavior of molecules with each other. Exemplary compounds that can be used as lead compounds for the development or design of congeners or analogs having useful pharmacological activity are described in U.S. Pat. No. 6,384,032; U.S. patent application Ser. No. 09/594,362 filed May 7, 2002; U.S. patent application Ser. No. 10/006,624 filed Nov. 30, 2001 (Publication No. 20020082259); U.S. patent application Ser. No. 10/000,742 filed Nov. 30, 2001 (Publication No. 20030139403); U.S. patent application Ser. No. 10/192,347 filed Jul. 10, 2002 (Publication No. 20030114446); U.S. patent application Ser. No. 10/305,039 filed Nov. 26, 2002; International Patent Publication No. WO 00/78757; International Patent Publication No. WO 03/04516; International Patent Application PCT/US03/32546 filed Oct. 14, 2003; U.S. Provisional Patent Application Ser. No. 60/518,791 filed Nov. 10, 2003; U.S. Provisional Patent Application Ser. No. 60/518,787 filed Nov. 10, 2003; U.S. Provisional Patent Application Ser. No. 60/518,788 filed Nov. 10, 2003; U.S. patent application Ser. No. 10/985,627, entitled, "Fused Heterocyclic Compounds," Mitsunori Ono et al, filed Nov. 10, 2004; U.S. patent application Ser. No. 10/985,716, entitled, "Heteroaryl Hydrazone Compounds," Mitsunori Ono et al, filed Nov. 10, 2004; U.S. patent application Ser. No. 10/985,696, entitled, "Pyridine Compounds," Mitsunori Ono, et al, filed Nov. 10, 2004, each of which is incorporated by reference herein in its entirety.

A number of articles review computer modeling of drugs interactive with specific proteins, such as Rotivinen et al., 1988, Acta Pharmaceutical Fennica 97:159-166; Ripka, 1998, New Scientist 54-57; McKinaly & Rossmann, 1989, Annu. Rev. Pharmacol. Toxiciol. 29:111-122; Perry & Davies, OSAR: Quantitative Structure-Activity Relationships in Drug Design pp. 189-193 (Alan R. Liss, Inc. 1989); Lewis & Dean, 1989, Proc. R. Soc. Lond. 236:125-140 and 141-162; Askew et al., 1989, J. Am. Chem. Soc. 111:1082-1090. Other computer programs that screen and graphically depict chemicals are available from companies such as BioDesign, Inc. (Pasadena, Calif.), Allelix, Inc. (Missisauga, Ontario, Canada), and Hypercube, Inc. (Cambridge, Ontario). Although these are primarily designed for application to drugs specific to particular proteins, they can be adapted to design of drugs specific to any identified region. Alternatively, lead compounds with little or no biologic activity, as ascertained in the screen, can also be used to design analogs and congeners of the compounds that have biologic activity.

Pharmaceutical Compositions and Therapeutic/Prophylactic Administration

The invention provides methods of treatment (and prophylaxis) by administration to a subject of an effective amount of a Therapeutic of the invention, i.e., a compound identified by the screening methods of the present invention. In a preferred aspect, the Therapeutic is substantially purified. The subject is preferably an animal including, but not limited to animals such as cows, pigs, horses, chickens, cats, dogs, etc., and is preferably a mammal, and most preferably human. In a specific embodiment, a non-human mammal is the subject.

In a particular embodiment, the present invention provides a method for treating a disease or disorder characterized by aberrant subcellular localization of c-Rel without a material alteration of the levels of expression of NFκB or amount of IκB comprising administering to a subject having such disease or disorder a composition comprising a molecule that reduces c-Rel nuclear localization without materially altering the levels of expression of NFκB or amount of IκB and a pharmaceutically acceptable carrier. In another particular embodiment, the invention provides a method for treating an IL-12 production-related disease or disorder comprising administering to a subject having such a disease or disorder a composition comprising a molecule that reduces c-Rel nuclear localization without materially altering the levels of expression of NFκB or amount of IκB and a pharmaceutically acceptable carrier. In another particular embodiment, the invention provides a method for treating a disease or disorder associated with c-Rel-dependent cytokine production comprising administering to a subject having such a disease or disorder a composition comprising a molecule that reduces c-Rel nuclear localization without materially altering the levels of expression of NFκB or amount of IκB and a pharmaceutically acceptable carrier. In yet another particular embodiment, the invention provides a method for treating an autoimmune disease or disorder comprising administering to a subject having such a disease or disorder a composition comprising a molecule that reduces c-Rel nuclear localization without materially altering the levels of expression of NFκB or amount of IκB and a pharmaceutically acceptable carrier. The molecule that reduces c-Rel nuclear localization without materially altering the levels of expression of NFκB or amount of IκB in the aforementioned methods can be those identified by screening methods herein (e.g., those delineated in the detailed description).

The compounds and compositions described herein are useful to treat and prevent any IL-12 production-related disorders, e.g., inflammatory disorders, immune diseases, neurological disorders and bone loss diseases. Methods of treatment and prevention are also provided.

The term "inflammatory disorders" includes any inflammatory disease, disorder or condition caused, exasperated or mediated by IL-12 production. Such inflammatory disorders may include, without limitation, asthma, adult respiratory distress syndrome, systemic lupus erythematosus, inflammatory bowel disease (including Crohn's disease and ulcerative colitis), multiple sclerosis, insulin-dependent diabetes mellitus, autoimmune arthritis (including rheumatoid arthritis, juvenile rheumatoid arthritis, psoriatic arthritis), inflammatory pulmonary syndrome, pemphigus vulgaris, idiopathic thrombocytopenic purpura, autoimmune meningitis, myasthenia gravis, autoimmune thyroiditis, dermatitis (including atopic dermatitis and eczematous dermatitis), psoriasis, Sjogren's Syndrome (including keratoconjunctivitis sicca secondary to Sjogren's Syndrome), alopecia areata, allergic responses due to arthropod bite reactions, aphthous ulcer, iritis, conjunctivitis, keratoconjunctivitis, cutaneous lupus erythematosus, scleroderma, vaginitis, proctitis, drug eruptions (such as Stevens-Johnson syndrome), leprosy reversal reactions, erythema nodosum leprosum, autoimmune uveitis, allergic encephalomyelitis, aplastic anemia, pure red cell anemia, idiopathic thrombocytopenia, polychondritis, Wegener's granulomatosis, chronic active hepatitis, Graves ophthalmopathy, primary biliary cirrhosis, uveitis posterior and interstitial lung fibrosis.

"Inflammatory disorders" expressly include acute inflammatory disorders. Examples of acute inflammatory disorders include graft versus host disease, transplant rejection, septic shock, endotoxemia, Lyme arthritis, infectious meningitis (e.g., viral, bacterial, Lyme disease-associated), an acute episode of asthma and acute episodes of an autoimmune disease.

"Inflammatory disorders" expressly include chronic inflammatory disorders. Nonlimiting examples of chronic inflammatory disorder include asthma, rubella arthritis, and chronic autoimmune diseases, such as systemic lupus erythematosus, psoriasis, inflammatory bowel disease, including Crohn's disease and ulcerative colitis, multiple sclerosis and rheumatoid arthritis.

The term "immune diseases" includes any immune disease, disorder or condition caused, exasperated or mediated by IL-12 production. Such immune diseases may include, without limitation, rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosus, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitivity reactions, allergic rhinitis, hay fever, perennial rhinitis, conjunctivitis, endometriosis, asthma, urticaria, systemic anaphalaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type ill hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemochromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited toasthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The term "neurological disorder" includes any neurological disease, disorder or condition caused, exasperated or mediated by IL-12 production. Such neurological disorders may include, without limitation, neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia telangiectasia, and mitochondrial multi-system disorder); demyelinating core disorders, such as multiple sclerosis, acute transverse myelitis; and disorders of the motor unit such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, 16, Edition, Merck & Company, Rahway, N.J. (1992).

The term "bone loss disease" includes any bone loss disease, disorder or condition caused, exasperated or mediated by IL-12 production e.g., periodontal disease, non-malignant bone disorders (e.g., osteoporosis, Paget's disease of bone, osteogenesis imperfecta, fibrous dysplasia, and primary hyperparathyroidism), estrogen deficiency, inflammatory bone loss, bone malignancy, arthritis, osteopetrosis, and certain cancer-related disorders (e.g., hypercalcemia of malignancy (HCM), osteolytic bone lesions of multiple myeloma and osteolytic bone metastases of breast cancer and other metastatic cancers.

In the case of overlap in these definitions, the disease, condition or disorder may be considered to be a member of any of the above listed classes of IL-12 production-related disorders. Specific IL-12 production related diseases include rheumatoid arthritis, sepsis, Crohn's disease, multiple sclerosis, psoriasis, or insulin-dependent diabetes mellitus).

Formulations and methods of administration that can be employed when the Therapeutic comprises a modulating compound identified by the assays described, supra; additional appropriate formulations and routes of administration can be selected from among those described herein below. Moreover, a Therapeutic of the invention can be also be administered in conjunction with any known drug to treat the disease or disorder of the invention.

Various delivery systems are known and can be used to administer a Therapeutic of the invention, e.g., encapsulation in liposomes, microparticles, and microcapsules, use of cells capable of expressing the Therapeutic, use of receptor-mediated endocytosis (e.g., Wu and Wu, 1987, J. Biol. Chem. 262:4429-4432); construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion, by bolus injection, by absorption through epithelial or mucocutaneous linings (e.g., oral, rectal and intestinal mucosa, etc.), and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a preferred embodiment, the Therapeutic is formulated for oral administration. These dosage forms include tablets (coated or uncoated), caplets, hard gelatin capsules, soft gelatin capsules, troches, dragées, dispersions, suspensions, solutions, and the like, including sustained release formulations well known in the art. See, e.g., Introduction to Pharmaceutical Dosage Forms, 1985, Ansel, H. C., Lea and Febiger, Philadelphia, Pa.; Remington's Pharmaceutical Sciences, 1995, Mack Publ. Co., Easton, Pa. Because of their ease of administration, tablets and capsules are preferred and represent the most advantageous oral dosage unit form, in which case solid pharmaceutical excipients are employed. If desired, tablets or caplets or capsules may be coated by standard aqueous or non-aqueous techniques.

In a specific embodiment, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the Therapeutic can be delivered in a vesicle, in particular a liposome (Langer, 1990, Science 249:1527-1533; Treat et al., 1989, In: Liposomes in the Therapy of Infectious Disease and Cancer, Lopez-Berestein and Fidler, eds., Liss, New York, pp. 353-365; Lopez-Berestein, ibid., pp. 317-327; see generally ibid.)

In yet another embodiment, the Therapeutic can be delivered via a controlled release system. In one embodiment, a pump may be used (Langer, supra; Sefton, 1987, CRC Crit. Ref. Biomed. Eng. 14:201-240; Buchwald et al., 1980, Surgery 88:507-516; Saudek et al., 1989, N. Engl. J. Med. 321:574-579). In another embodiment, polymeric materials can be used (Medical Applications of Controlled Release, Langer and Wise, eds., CRC Press, Boca Raton, Fla., 1974; Controlled Drug Bioavailability, Drug Product Design and Performance, Smolen and Ball, eds., Wiley, New York, 1984; Ranger and Peppas, 1983, Macromol. Sci. Rev. Macromol. Chem. 23:61; Levy et al., 1985, Science 228:190-192; During et al., 1989, Ann. Neurol. 25:351-356; Howard et al., 1989, J. Neurosurg. 71:858-863). In yet another embodiment, a controlled release system can be placed in proximity of the therapeutic target, i.e., the brain, thus requiring only a fraction of the systemic dose (e.g., Goodson, 1984, In: Medical Applications of Controlled Release, supra, Vol. 2, pp. 115-138). Other controlled release systems are discussed in the review by Langer (1990, Science 249:1527-1533).

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water can be a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated, in accordance with routine procedures, as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water or saline for injection can be provided so that the ingredients may be mixed prior to administration.

The Therapeutics of the invention can be formulated as neutral or salt forms. Pharmaceutically acceptable salts include those formed with free carboxyl groups such as those derived from hydrochloric, phosphoric, acetic, oxalic, tartaric acids, etc., those formed with free amine groups such as those derived from isopropylamine, triethylamine, 2-ethylamino ethanol, histidine, procaine, etc., and those derived from sodium, potassium, ammonium, calcium, and ferric hydroxides, etc.

Preferred pharmaceutical compositions and dosage forms comprise a Therapeutic of the invention, or a pharmaceutically acceptable prodrug, salt, solvate, or clathrate thereof, optionally in combination with one or more additional active agents.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 1-50 milligrams of active compound per kilogram body weight. Suitable dosage ranges for intranasal administration are generally about 0.1 mg/kg body weight to 50 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

Exemplary doses of a small molecule include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

For antibodies, proteins, polypeptides, peptides and fusion proteins encompassed by the invention, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention or fragments thereof may be reduced by enhancing uptake and tissue penetration of the antibodies by modifications such as, for example, lipidation.

Moreover, in certain embodiments, since IL-12 production can be inhibited at a lower drug concentration that that needed to inhibit IL-6 or IFN-γ production, appropriate dosages include those that selectively inhibit IL-12 production but not other cytokines.

The Therapeutics of the present invention may also be administered by controlled release means or delivery devices that are well known to those of ordinary skill in the art, such as those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566. These controlled release compositions can be used to provide slow or controlled-release of one or more of the active ingredients therein using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable controlled-release formulations known to those of ordinary skill in the art may be readily selected for use with the pharmaceutical compositions of the invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations may include extended activity of the drug, reduced dosage frequency, and/or increased patient compliance.

Most controlled-release formulations are designed to initially release an amount of the Therapeutic that promptly produces the desired therapeutic effect, and gradually and continually releases other amounts of the Therapeutic to maintain the appropriate level of therapeutic effect over an extended period of time. In order to maintain this constant level of Therapeutic in the body, the Therapeutic must be released from the composition at a rate that will replace the amount of Therapeutic being metabolized and excreted from the body. The controlled-release of the Therapeutic may be stimulated by various inducers, for example, pH, temperature, enzymes, water, or other physiological conditions or compounds. Such controlled-release components in the context of the present invention include, but are not limited to, polymers, polymer matrices, gels, permeable membranes, liposomes, microspheres, or the like, or a combination thereof, that facilitates the controlled-release of the active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The methods for treating or preventing an IL-12 production related disease or disorders, or those associated with aberrant c-Rel subcellular localization or autoimmune disease or disorders in a patient in need thereof can further comprise administering to the patient being administered a compound of this invention, an effective amount of one or more other therapeutic agents. Such therapeutic agents may include other therapeutic agents such as those conventionally used to prevent or treat disorders associated with IL-12 production or aberrant c-Rel subcellular localization or symptoms thereof. The other therapeutic agent can be a steroid or a non-steroidal anti-inflammatory agent. Useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof. For a more detailed description of the NSAIDs, see Paul A. Insel, *Analgesic-Antipyretic and Antiinflammatory Agents and Drugs Employed in the Treatment of Gout, in Goodman & Gilman's The Pharmacological Basis of Therapeutics* 617-57 (Perry B. Molinhoff and Raymond W. Ruddon eds., 9$^{th}$ ed 1996) and Glen R. Hanson, *Analgesic, Antipyretic and Anti-inflammatory Drugs in Remington: The Science and Practice of Pharmacy Vol II* 1196-1221 (A. R. Gennaro ed. 19th ed. 1995) which are hereby incorporated by reference in their entireties.

Other Examples of prophylactic and therapeutic agents include, but are not limited to, immunomodulatory agents, anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steroids, non-steriodal anti-inflammatory drugs (e.g., aspirin, ibuprofen, diclofenac, and COX-2 inhibitors), and leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), antiviral agents, and antibiotics (e.g., dactinomycin (formerly actinomycin), bleomycin, erythomycin, penicillin, mithramycin, and anthramycin (AMC)).

In combination therapy treatment, both the compounds of this invention and the other drug agent(s) are administered to mammals (e.g., humans, male or female) by conventional methods. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment of the invention where another therapeutic agent is administered to an animal, the effective amount of the compound of this invention is less than its effective amount would be where the other therapeutic agent is not administered. In another embodiment, the effective amount of the conventional agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same patient visit.

In certain embodiments, one or more compounds of the invention and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the administration of the same compounds of the invention may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of the same therapy (e.g., prophylactic or therapeutic agent) other than a compound of the invention may be repeated and the administration may be separated by at least at least 1 day, 2 days, 3 days, 5 days, 10 days, 15 days, 30 days, 45 days, 2 months, 75 days, 3 months, or at least 6 months.

Any immunomodulatory agent well-known to one of skill in the art may be used in the co-administration methods and compositions of the invention. Immunomodulatory agents can affect one or more or all aspects of the immune response in a subject. Aspects of the immune response include, but are not limited to, the inflammatory response, the complement cascade, leukocyte and lymphocyte differentiation, proliferation, and/or effector function, monocyte and/or basophil counts, and the cellular communication among cells of the immune system. In certain embodiments of the invention, an immunomodulatory agent modulates one aspect of the immune response. In other embodiments, an immunomodulatory agent modulates more than one aspect of the immune response. In a preferred embodiment of the invention, the administration of an immunomodulatory agent to a subject inhibits or reduces one or more aspects of the subject's immune response capabilities. In a specific embodiment of the invention, the immunomodulatory agent inhibits or suppresses the immune response in a subject. In accordance with the invention, an immunomodulatory agent is not antibody that immunospecifically binds to c-Rel. In certain embodiments, an immunomodulatory agent is not an anti-inflammatory agent. In certain embodiments, an immunomodulatory agent is not an anti-angiogenic agent. In other embodiments, an immunomodulatory agent is not an integrin antagonist. In other embodiments, an immunomodulatory agent is not a TNF-α antagonist. In certain embodiments, an immunomodulatory agent is a chemotherapeutic agent. In certain embodiments, an immunomodulatory agent is not a chemotherapeutic agent.

Examples of immunomodulatory agents include, but are not limited to, proteinaceous agents such as cytokines, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, cytokine receptor modulators, and modulators mast cell modulators.

Examples of T cell receptor modulators include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies (e.g., MEDI-507 (MedImmune, Inc., International Publication Nos. WO 02/098370 and WO 02/069904), anti-CD11a antibodies (e.g., Xanelim (Genentech)), and anti-B7 antibodies (e.g., IDEC-114) (IDEC))), CTLA4-immunoglobulin, and LFA-3TIP (Biogen, International Publication No. WO 93/08656 and U.S. Pat. No. 6,162,432).

Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin IL-2, IL-3, IL-4, IL-5, IL-6, IL-7, IL-8, IL-9, IL-10, IL-11, IL-13, IL-15, IL-23, TNF-α, TNF-β, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-3 receptor antibodies, anti-IL-4 receptor antibodies, anti-IL-6 receptor antibodies, anti-IL-10 receptor antibodies, anti-IL-12 receptor antibodies, anti-IL-13 receptor antibodies, anti-IL-15 receptor antibodies, and anti-IL-23 receptor antibodies), anti-cytokine antibodies.

In a specific embodiment, a cytokine receptor modulator is IL-3, IL-4, IL-10, or a fragment thereof. In another embodiment, a cytokine receptor modulator is the extracellular domain of a TNF-α receptor or a fragment thereof. In certain embodiments, a cytokine receptor modulator is not a TNF-α antagonist.

In one embodiment, a cytokine receptor modulator is a mast cell modulator. In an alternative embodiment, a cytokine receptor modulator is not a mast cell modulator. Examples of mast cell modulators include, but are not limited to stem cell factor (c-kit receptor ligand) inhibitor (e.g., mAb 7H6, mAb 8H7a, pAb 1337, FK506, CsA, dexamethasone, and fluconcinonide), c-kit receptor inhibitor (e.g., STI 571 (formerly known as CGP 57148B)), mast cell protease inhibitor (e.g., GW-45, GW-58, wortmannin, LY 294002, calphostin C, cytochalasin D, genistein, KT5926, staurosproine, and lactoferrin), relaxin ("RLX"), IgE antagonist (e.g., antibodies rhuMAb-E25 omalizumab, HMK-12 and 6HD5, and mAB Hu-901), IL-3 antagonist, IL-4 antagonists, IL-10 antagonists, and TGF-beta.

An immunomodulatory agent may be selected to interfere with the interactions between the T helper subsets (TH1 or TH2) and B cells to inhibit neutralizing antibody formation. Antibodies that interfere with or block the interactions necessary for the activation of B cells by TH (T helper) cells, and thus block the production of neutralizing antibodies, are useful as immunomodulatory agents in the methods of the invention. For example, B cell activation by T cells requires certain interactions to occur (Durie et al., Immunol. Today, 15(9):406-410 (1994)), such as the binding of CD40 ligand on the T helper cell to the CD40 antigen on the B cell, and the binding of the CD28 and/or CTLA4 ligands on the T cell to the B7 antigen on the B cell. Without both interactions, the B cell cannot be activated to induce production of the neutralizing antibody.

The CD40 ligand (CD40L)-CD40 interaction is a desirable point to block the immune response because of its broad activity in both T helper cell activation and function as well as the absence of redundancy in its signaling pathway. Thus, in a specific embodiment of the invention, the interaction of CD40L with CD40 is transiently blocked at the time of administration of one or more of the compounds of the invention and immunomodulatory agents. This can be accomplished by treating with an agent which blocks the CD40 ligand on the TH cell and interferes with the normal binding of CD40 ligand on the T helper cell with the CD40 antigen on the B cell. An antibody to CD40 ligand (anti- CD40L) (available from Bristol-Myers Squibb Co; see, e.g., European patent application 555,880, published Aug. 18, 1993) or a soluble CD40 molecule can be selected and used as an immunomodulatory agent in accordance with the methods of the invention.

An immunomodulatory agent may be selected to inhibit the interaction between TH1 cells and cytotoxic T lymphocytes ("CTLs") to reduce the occurrence of CTL-mediated killing. An immunomodulatory agent may be selected to alter (e.g., inhibit or suppress) the proliferation, differentiation, activity and/or function of the CD4+ and/or CD8+ T cells. For example, antibodies specific for T cells can be used as immunomodulatory agents to deplete, or alter the proliferation, differentiation, activity and/or function of CD4+ and/or CD8+ T cells.

In one embodiment of the invention, an immunomodulatory agent that reduces or depletes T cells, preferably memory T cells, is administered to a subject at risk of or with a disease or disorder associated with or characterized by aberrant expression and/or activity of an IL-9 polypeptide, a disease or disorder associated with or characterized by aberrant subcellular localization of c-Rel, an autoimmune disease, an inflammatory disease, a proliferative disease, or an infection (preferably, a respiratory infection) in accordance with the methods of the invention. See, e.g., U.S. Pat. No. 4,658,019. In another embodiment of the invention, an immunomodulatory agent that inactivates CD8+ T cells is administered to a subject at risk of or with a disease or disorder associated with or characterized by aberrant subcellular localization of c-Rel, a disease or disorder associated with or characterized by aberrant subcellular localization of c-Rel, an autoimmune disease, an inflammatory disease, a proliferative disease, or an infection (preferably, a respiratory infection) in accordance with the methods of the invention. In a specific embodiment, anti-CD8 antibodies are used to reduce or deplete CD8+ T cells.

In another embodiment, an immunomodulatory agent which reduces or inhibits one or more biological activities (e.g., the differentiation, proliferation, and/or effector functions) of TH0, TH1, and/or TH2 subsets of CD4+T helper cells is administered to a subject at risk of or with a disease or disorder associated with or characterized by aberrant expression subcellular localization of c-Rel, a disease or disorder associated with or characterized by aberrant subcellular localization of c-Rel, an autoimmune disease, an inflammatory disease, a proliferative disease, or an infection (preferably, a respiratory infection) in accordance with the methods of the invention. One example of such an immunomodulatory agent is IL-4. IL-4 enhances antigen-specific activity of TH2 cells at the expense of the TH1 cell function (see, e.g., Yokota et al, 1986 Proc. Natl. Acad. Sci., USA, 83:5894-5898; and U.S. Pat. No. 5,017,691). Other examples of immunomodulatory agents that affect the biological activity (e.g., proliferation, differentiation, and/or effector functions) of T-helper cells (in particular, TH1 and/or TH2 cells) include, but are not limited to, IL-2, IL-4, IL-5, IL-6, IL-10, IL-13, IL-15, and interferon (IFN)-γ.

In another embodiment, an immunomodulatory agent administered to a subject at risk of or with a disease or disorder associated with or characterized by aberrant subcellular localization of c-Rel, an autoimmune disease, an inflammatory disease, a proliferative disease, or an infection (preferably, a respiratory infection) in accordance with the methods of the invention is a cytokine that prevents antigen presentation. In a specific embodiment, an immunomodulatory agent used in the methods of the invention is IL-10. IL-10 also reduces or inhibits macrophage action which involves bacterial elimination.

An immunomodulatory agent may be selected to reduce or inhibit the activation, degranulation, proliferation, and/or infiltration of mast cells. In certain embodiments, the immunomodulatory agent interferes with the interactions between mast cells and mast cell activating agents, including, but not limited to stem cell factors (c-kit ligands), IgE, IL-4, environmental irritants, and infectious agents. In a specific embodiment, the immunomodulatory agent reduces or inhibits the response of mast cells to environmental irritants such as, but not limited to pollen, dust mites, tobacco smoke, and/or pet dander. In another specific embodiment, the immunomodulatory agent reduces or inhibits the response of mast cells to infectious agents, such as viruses, bacteria, and fungi. Examples of mast cell modulators that reduce or inhibit the activation, degranulation, proliferation, and/or infiltration of mast cells include, but are not limited to, stem cell factor (c-kit receptor ligand) inhibitors mAb 7H6, mAb 8H7a, and pAb 1337 (see Mendiaz et al., 1996, Eur J Biochem 293(3):842-849), FK506 and CsA (Ito et al., 1999 Arch Dermatol Res 291(5):275-283), dexamethasone and fluconcinonide (see Finooto et al. J Clin Invest 1997 99(7): 1721-1728)), c-kit receptor inhibitors (e.g., STI 571 (formerly known as CGP 57148B) (see Heinrich et al., 2000 Blood 96(3):925-932)), mast cell protease inhibitors (e.g., GW-45 and GW-58 (see Temkin et al., 2002 J Immunol 169(5):2662-2669), wortmannin, LY 294002, calphostin C, and cytochalasin D (see Vosseller et al., 1997, Mol Biol Cell 1997:909-922), genistein, KT5926, and staurosproine (see Nagai et al. 1995, Biochem Biophys Res Commun 208(2): 576-581), and lactoferrin (see He et al., 2003 Biochem Pharmacol 65(6):1007-1015)), relaxin ("RLX") (see Bani et al., 2002 Int Immunopharmacol 2(8):1195-1294),), IgE antagonists (e.g., antibodies rhuMAb-E25 omalizumab (see Finn et al., 2003 J Allergy Clin Immuno 111(2):278-284; Corren et al., 2003 J Allergy Clin Immuno 111(1):87-90; Busse and Neaville, 2001 Curr Opin Allergy Clin Immuno 1(1):105-108; and Tang and Powell, 2001, Eur J Pediatr 160(12): 696-704), HMK-12 and 6HD5 (see Miyajima et al., 2202 Int Arch Allergy Immuno 128(1):24-32), and mAB Hu-901 (see van Neerven et al., 2001 Int Arch Allergy Immuno 124(1-3):400), IL-3 antagonist, IL-4 antagonists, IL-10 antagonists, and TGF-beta (see Metcalfe et al., 1995, Exp Dermatol 4(4 Pt 2):227-230).

In a preferred embodiment, proteins, polypeptides or peptides (including antibodies) that are utilized as immunomodulatory agents are derived from the same species as the recipient of the proteins, polypeptides or peptides so as to reduce the likelihood of an immune response to those proteins, polypeptides or peptides. In another preferred embodiment, when the subject is a human, the proteins, polypeptides, or peptides that are utilized as immunomodulatory agents are human or humanized.

In accordance with one embodiment of the invention, one or more immunomodulatory agents are administered to a subject at risk of or with a disease or disorder associated with or characterized by aberrant subcellular localization of c-Rel, an autoimmune disease, an inflammatory disease, a proliferative disease, or an infection (preferably, a respiratory infection) prior to, subsequent to, or concomitantly with a compound of the invention that alters the subcellular localization of c-Rel and that does not materially alter the expression of NFκB and/or the amount of IκB. Preferably, one or more immunomodulatory agents are administered in combination with a compound of the invention that alters the subcellular localization of c-Rel and that does not materially alter the expression of NFκB and/or the amount of IκB to a subject at risk of or with a disease or disorder associated with or characterized by aberrant subcellular localization of c-Rel, an autoimmune disease, an inflammatory disease, a proliferative disease, or an infection (preferably, a respiratory infection) to reduce or inhibit one or more aspects of the immune response as deemed necessary by one of skill in the art. Any technique well-known to one skilled in the art can be used to measure one or more aspects of the immune response in a particular subject, and thereby determine when it is necessary to administer an immunomodulatory agent to said subject. In a preferred embodiment, a mean absolute lymphocyte count of approximately 500 cells/mm3, preferably 600 cells/mm3, 650 cells/mm3, 700 cells/mm3, 750 cells/mm3, 800 cells/mm3, 900 cells/mm3, 1000 cells/mm3, 1100 cells/mm3, or 1200 cells/mm3 is maintained in a subject. In another preferred embodiment, the subject is not administered a compound of the invention if their absolute lymphocyte count is 500 cells/mm3 or less, 550 cells/mm3 or less, 600 cells/mm3 or less, 650 cells/mm3 or less, 700 cells/mm3 or less, 750 cells/mm3 or less, or 800 cells/mm3 or less.

In a preferred embodiment, one or more immunomodulatory agents are administered in combination with a compound of the invention so as to transiently reduce or inhibit one or more aspects of the immune response. Such a transient inhibition or reduction of one or more aspects of the immune system can last for hours, days, weeks, or months. Preferably, the transient inhibition or reduction in one or more aspects of the immune response lasts for a few hours (e.g., 2 hours, 4 hours, 6 hours, 8 hours, 12 hours, 14 hours, 16 hours, 18 hours, 24 hours, 36 hours, or 48 hours), a few days (e.g., 3 days, 4 days, 5 days, 6 days, 7 days, or 14 days), or a few weeks (e.g., 3 weeks, 4 weeks, 5 weeks or 6 weeks).

Any anti-inflammatory agent, including agents useful in therapies for inflammatory disorders, well-known to one of skill in the art can be used in the compositions and methods of the invention. Non-limiting examples of anti-inflammatory agents include non-steroidal anti-inflammatory drugs (NSAIDs), steroidal anti-inflammatory drugs, anticholinergics (e.g., atropine sulfate, atropine methylnitrate, and ipratropium bromide (ATROVENT™)), beta2-agonists (e.g., abuterol (VENTOLIN™ and PROVENTIL™), bitolterol (TORNALATE™), levalbuterol (XOPONEX™), metaproterenol (ALUPENT™), pirbuterol (MAXAIR™), terbutlaine (BRETHAIRE™ and BRETHINE™), albuterol (PROVENTIL™, REPETABS™, and VOLMAX™), formoterol (FORADIL AEROLIZER™), and salmeterol (SEREVENT™ and SEREVENT DISKUS™)), and methylxanthines (e.g., theophylline (UNIPHYL™, THEO-DUR™, SLO-BID™, AND TEHO-42™)). Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketorolac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxgenase enzyme (e.g., COX-1 and/or COX-2). Examples of steroidal anti-inflammatory drugs include, but are not limited to, glucocorticoids, dexamethasone (DECADRON™), corticosteroids (e.g., methylprednisolone (MEDROL™)), cortisone, hydrocortisone, prednisone (PREDNISONE™ and DELTASONE™), prednisolone (PRELONE™ and PEDI-APRED™), triamicinolone, azulfidine, and inhibitors of eicosanoids (e.g., prostaglandins, thromboxanes, and leukotrienes). Anti-inflammatory therapies and their dosages, routes of administration, and recommended usage are known in the art and have been described in such literature as the *Physician's Desk Reference* (57th ed., 2003).

For arthritis, inflammation-mediated bone loss and other disorders that have an inflammatory component, preferred conventional treatments for use in combination therapy with the compounds and compositions of this invention include (without limitation) naproxen sodium (Anaprox® and Anaprox® DS, Roche), flurbiprofen (Ansaid®; Pharmacia), diclofenac sodium+misoprostil (Arthrotec®, Searle), valdecoxib (Bextra®, Pharmacia), diclofenac potassium (Cataflam® and Voltaren®. Novartis), celecoxib (Celebrex®, Pharmacia), sulindac (Clinoril®, Merck), oxaprozin (Daypro®, Pharmacia), salsalate (Disalcid®, 3M), diflunisal (Dolobid®, Merck), naproxen sodium (EC Naprosyn®, Roche), piroxicam (Feldene®, Pfizer), indomethacin (Indocin® and Indocin SR®, Merck), etodolac (Lodine® and Lodine XL®, Wyeth), meloxicam (Mobic®, Boehringer Ingelheim), ibuprofen (Motrin®, Pharmacia), naproxen (Naprelan®, Elan), naproxen (Naprosyn®, Roche), ketoprofen (Orudis® and Oruvail®, Wyeth), nabumetone (Relafen®, SmithKline), tolmetin sodium (Tolectin®, McNeil), choline magnesium trisalicylate (Trilisate®, Purdue Fredrick), and rofecoxib (Vioxx®, Merck).

In any case where pain in a component of the target disorder, the other therapeutic agent can be an analgesic. Useful analgesics include, but are not limited to, phenacetin, butacetin, acetaminophen, nefopam, acetoamidoquinone, and mixtures thereof.

For use against osteoporosis, Paget's disease and other disorders associated with bone deterioration, preferred conventional agents that may be used in combination with compounds and compositions of this invention include (without limitation) bisphosphonates (such as etidronate (Didronel®, Procter & Gamble), pamidronate (Aredia®, Novartis), and alendronate (Fosamax®, Merck)), tiludronate (Skelid®, Sanofi-Synthelabo, Inc.), risedronate (Actonel®, Procter & Gamble/Aventis), calcitonin (Miacalcin®), estrogens (Climara®, Estrace®, Estrademi®, Estratab®, Ogen®, Ortho-Est®, Premarin®, and others) estrogens and progestins (Activella™, FemHrt®, Premphase®, Prempro®, and others), parathyroid hormone and portions thereof, such as teriparatide (Forteo®, Eli Lilly and Co.), selective estrogen receptor modulators (SERMs) (such as raloxifene (Evista®)) and treatments currently under investigation (such as other parathyroid hormones, sodium fluoride, vitamin D metabolites, and other bisphosphonates and selective estrogen receptor modulators).

Any parathyroid hormone (PTH) may be used in combination with the compound of this invention. The term parathyroid hormone refers to parathyroid hormone, fragments or metabolites thereof and structural analogs thereof which can stimulate bone formation and increase bone mass. Also included are parathyroid hormone related peptides and active fragments and analogs of parathyroid related peptides (see PCT publication No. WO 94/01460). Such bone anabolic functional activity is readily determined by those skilled in the art of standard assays. A variety of these compounds are described and referenced below. However, other parathyroid hormone will be known to those skilled in the art. Exemplary parathyroid hormones are disclosed in the following references. "Human Parathyroid Peptide Treatment of Vertebral Osteoporosis", Osteoporosis Int., 3, (Supp 1):199-203. "PTH 1-34 Treatment of Osteoporosis with Added Hormone Replacement Therapy: Biochemical, Kinetic and Histological Responses" Osteoporosis Int. 1: 162-170.

Any growth hormone or growth hormone secretagogue may be used in combination with the compounds of this invention. The term growth hormone secretagogue refers to a compound which stimulates the release of growth hormone or mimics the action of growth hormone (e.g., increases bone formation leading to increased bone mass). Such actions are readily determined by those skilled in the art of standard assays well known to those of skill in the art. A variety of these compounds are disclosed in the following published PCT patent applications: WO 95/14666; WO 95/13069; WO 94/19367; WO 94/13696; and WO 95/34311. However, other growth hormones or growth hormone secretagogues will be known to those skilled in the art. In particular, a preferred growth hormone secretagogue is N-[1(R)-[1,2-Dihydro-1-methanesulfonylspiro[3H-indole-3,4'-piperidin]-1'-yl) carbonyl]-2-(phenylmethyloxy)ethyl]-2-amino-2-methylpropanamide: MK-667. Other preferred growth hormone secretagogues include 2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide or its L-tartaric acid salt; 2-amino-N-(1-(R)-benzyloxymethyl-2-(3a-(R)-(4-fluoro-benzyl)-2-methyl-3-oxo-2,3,3a,4,6,7-hexahydro-pyrazolo[4,3-c]pyridin-5-yl)-2-oxo-ethyl)isobutyramide; 2-amino-N-(2-(3a-(R)-benzyl-3-oxo-2,3,3a,4,6,7-hexahydro-pyrazolo[4,3-c]pyridin-5-yl)-1-(R)benzyloxymethyl-2-oxo-ethyl) isobutyramide; and 2-amino-N-(1-(2,4-difluoro-benzyloxymethyl)-2-oxo-2-(3-oxo-3a-pyridin-2-ylmethyl-2-(2,2,2-trifluoro-ethyl)-2,3,3a,4,6,7-hexahydro-pyrazolo[4,3-c]pyridin-5-yl)-ethyl)-2-methyl-propionamide.

Any method of the present invention can comprise administering an effective amount of a composition or pharmaceutical composition comprising at least one compound of this invention to a cell, tissue, organ, animal or patient in need of such modulation, treatment or therapy. Such a method can optionally further comprise co-administration or combination therapy for treating an IL-12 production related disorder, wherein the administering further comprises administering before, concurrently with, and/or after the compound of this invention, at least one additional active agent selected from a TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., (i-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonism. Suitable dosages are well known in the art. See, e.g., Wells et al., eds., Pharmacotherapy Handbook, 2.sup.nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

TNF antagonists suitable for compositions, combination therapy, co-administration, devices and/or methods of the present invention include, but are not limited to, anti-TNF antibodies (such as, Remicade (Infliximab) or Humira (adalimumab)) for example, or, antigen-binding fragments thereof, and receptor molecules which bind specifically to TNF (such as, for example, Enbrel (Etanercept)); compounds which prevent and/or inhibit TNT synthesis, TNF release or its action on target cells, such as thalidomide, tenidap, phosphodiesterase inhibitors (e.g, pentoxifylline and rolipram), A2b adenosine receptor agonists and A2b adenosine receptor enhancers; compounds which prevent and/or inhibit TNF receptor signaling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

For clarification, a "tumor necrosis factor antibody," "TNF antibody," "TNF antibody," or fragment and the like decreases, blocks, inhibits, abrogates or interferes with TNF activity in vitro, in situ and/or preferably in vivo. For example, a suitable TNF human antibody of the present invention can bind TNFa and includes anti-TNT antibodies, antigen-binding fragments thereof, and specified mutants or domains thereof that bind specifically to TNFa. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

The foregoing and other useful combination therapies will be understood and appreciated by those of skill in the art. Potential advantages of such combination therapies include the ability to use less of each of the individual active ingredients to minimize toxic side effects, synergistic improvements in efficacy, improved ease of administration or use and/or reduced overall expense of compound preparation or formulation. The biological activities of a compound of this invention can be evaluated by a number of cell-based assays. One of such assays can be conducted using cells from human peripheral blood mononuclear cells (PBMC) or human monocytic cell line (THP-1). The cells are stimulated with a combination of human interferon-γ (IFN-γ) and lipopolysaccharide or a combination of IFN-γ and *Staphylococcus aureus* Cowan I in the presence of a test compound. The level of inhibition of IL-12 production can be measured by, e.g., determining the amount of p70 by using a sandwich ELBA assay with anti-human IL-12 antibodies. $IC_{50}$ of the test compound can then be determined. Specifically, PBMC or THP-1 cells are incubated with the test compound. Cell viability was assessed using the bioreduction of MTS [3-(4,5-dimethylthiazol-2-yl)-5-(3-carboxymethoxyphenyl)-2-(4-sulfophenyl)-2H-tetrazolium] (Promega, Madison, Wis.).

The other therapeutic agent can include bone anti-resorptive agents for example progestins, polyphosphates, bisphosphonate(s), estrogen agonists/antagonists, estrogen (such as Premarin®), estrogen/progestin combinations, and estrogen derivatives (such as estrone, estriol or 17α, 17β-ethynyl estradiol). Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, dthynodiol diacetate, etonogestrel, flurogestone acetate, gestaclone, gestodene, gestonorone caproate, gestrinone, haloprogesterone, hydroxyprogesterone, caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol. Preferred progestins are medroxyprogestrone, norethindrone and norethynodrel.

Exemplary bone resorption inhibiting polyphosphonates include polyphosphonates of the type disclosed in U.S. Pat. No. 3,683,080. Preferred polyphosphonates are geminal dipolyphosphonates (also referred to as bis-phosphonates). Tiludronate disodium is an especially preferred polyphosphonate. Ibandronic acid is an especially preferred polyphosphonate. Alendronate is an especially preferred polyphosphonate. Zoledronic acid is an especially preferred polyphosphonate. Other preferred polyphosphonates are 6-amino-1-hydroxy-hexylidene-biphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N(2-hydroxyethyl)amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used for this purpose. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue; and blocking the actions of estrogen in one or more tissues. Such activities are readily determined by those skilled in the art of standard assays including estrogen receptor binding assays, standard bone histomorphometric and densitometer methods, and E. F Eriksen et al., Bone Histomorphometry, Raven Press, New York, pp. 1-74 (1994); S. J. Grier et al., The Use of Dual-Energy X-Ray Absorptiometry In Animals, Inv. Radiol. 31(1): 50-62 (1996); Wahner H. W. and Fogelman I., The Evaluation of Osteoporosis: Dual Energy X-Ray Absorptiometry in Clinical Practice, Martin Dunitz Ltd., London, pp. 1-296 (1994)). A variety of these compounds are described and referenced below.

A preferred estrogen agonist/antagonist is droloxifene: (phenol, 3-(1-(4-(2-(dimethylamino)ethoxy)phenyl)-2-phenyl-1-butenyl)-, (E)-) and related compounds which are disclosed in U.S. Pat. No. 5,047,431. Another preferred estrogen agonist/antagonist is 3-(4-(1,2-diphenyl-but-1-enyl)-phenyl)-acrylic acid, which is disclosed in Wilson et al., Endocrinology 138: 3901-11 (1997). Another preferred estrogen agonist/antagonist is tamoxifen: (ethanamine, 2-(-4-(1,2-diphenyl-1-butenyl)phenoxy)-N,N-dimethyl, (Z)-2-, 2-hydroxy-1,2,3-propanetricarboxylate (1:1)) and related compounds which are disclosed in U.S. Pat. No. 4,536,516. Another related compound is 4-hydroxy tamoxifen which is disclosed in U.S. Pat. No. 4,623,660.

A preferred estrogen agonist/antagonist is raloxifene: (methanone, (6-hydroxy-2-(4-hydroxyphenyl)benzo[b]thien-3-yl)(4-(2-(1-piperidinyl)ethoxy)phenyl)hydrochloride) which is disclosed in U.S. Pat. No. 4,418,068. Another preferred estrogen agonist/antagonist is toremifene: (ethanamine, 2-(4-(4-chloro-1,2-diphenyl-1-butenyl)phenoxy)-N,N-dimethyl-, (Z)-, 2-hydroxy-1,2,3-propanetricarboxylate (1:1) which is disclosed in U.S. Pat. No. 4,996,225. Another preferred estrogen agonist/antagonist is centchroman: 1-(2-((4-(-methoxy-2,2,dimethyl-3-phenyl-chroman-4-yl)-phenoxy)-ethyl)-pyrrolidine, which is disclosed in U.S. Pat. No. 3,822,287. Also preferred is levormeloxifene. Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155. Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058. Another preferred estrogen agonist/antagonist is 6-(4-hydroxy-phenyl)-5-(4-(2-piperidin-1-yl-ethoxy)-benzyl)-naphthalen-2-ol which is disclosed in U.S. Pat. No. 5,484,795. Another preferred estrogen agonist/antagonist is (4-(2-(2-aza-bicyclo[2.2.1]hept-2-yl)-ethoxy)-phenyl)-(6-hydroxy-2-(4-hydroxy-phenyl)-benzo[b]thiophen-3-yl)-methanone which is disclosed, along with methods of preparation, in PCT publication no. WO 95/10513 assigned to Pfizer Inc. Other preferred estrogen agonists/antagonists include compounds as described in U.S. Pat. No. 5,552,412. Especially preferred compounds described therein are: cis-6-(4-fluoro-phenyl)-5-(4-(2-piperidin-1-yl-ethoxy)-phenyl)-5,6,7,8-tetrahydro-naphthalene-2-ol; (-)-cis-6-phenyl-5-(4-(2-pyrrolidin-1-yl-ethoxy)-phenyl)-5,6,7,8-tetrahydro-naphthalene-2-ol; cis-6-phenyl-5-(4-(2 pyrrolidin-1-yl-ethoxy)-phenyl)-5,6,7,8-tetrahydro-naphthalene-2-ol; cis-1-(6'-pyrrolodinoethoxy-3'-pyridyl)-2-phenyl-6-hydroxy-1,2,3,4-tetrahydronaphthalene; 1-(4'-pyrrolidinoethoxyphenyl)-2-(4''-fluorophenyl)-6-hydroxy-1,2,3,4-tetrahydroisoquinoline; cis-6-(4-hydroxyphenyl)-5-(4-(2-piperidin-1-yl-ethoxy)-phenyl)-5,6,7,8-tetrahydro-naphthalene-2-ol; and 1-(4'-pyrrolidinolethoxyphenyl)-2-phenyl-6-hydroxy-1,2,3,4-tetrahydroisoquinoline. Other estrogen agonists/antagonists are described in U.S. Pat. No.

4,133,814. U.S. Pat. No. 4,133,814 discloses derivatives of 2-phenyl-3-aroyl-benzothiophene and 2-phenyl-3-aroylbenzothiophene-1-oxide.

Those skilled in the art will recognize that other bone anabolic agents, also referred to as bone mass augmenting agents, may be used in conjunction with the compounds of this invention. A bone mass augmenting agent is a compound that augments bone mass to a level which is above the bone fracture threshold as detailed in the World Health Organization Study World Health Organization, "Assessment of Fracture Risk and its Application to Screening for Postmenopausal Osteoporosis (1994). Report of a WHO Study Group. World Health Organization Technical Series 843." Any prostaglandin, or prostaglandin agonist/antagonist may be used in combination with the compounds of this invention. Those skilled in the art will recognize that IGF-1, sodium fluoride, parathyroid hormone (PTH), active fragments of parathyroid hormone, growth hormone or growth hormone secretagogues may also be used. The following paragraphs describes in greater detail exemplary compounds that may be administered in combination with compounds of this invention.

Prostaglandins: The term prostaglandin refers to compounds which are analogs of the natural prostaglandins $PGD_1$, $PGD_2$, $PGE_2$, $PGE_1$ and $PGF_2$ which are useful in the treatment of osteoporosis and other disorders associated with excessive osteoclastic bone resorption. These compounds bind to the prostaglandins receptors. Such binding is readily determined by those skilled in the art of standard assays (e.g., S. An et al., Cloning and Expression of the $EP_2$ Subtype of Human Receptors for Prostaglandin $E_2$ Biochemical and Biophysical Research Communications, 197 (1): 263-270 (1993)).

Prostaglandins are alicyclic compounds related to the basic compound prostanoic acid. The carbon atoms of the basic prostaglandin are numbered sequentially from the carboxylic carbon atom through the cyclopentyl ring to the terminal carbon atom on the adjacent side chain. Normally the adjacent side chains are in the trans orientation. The presence of an oxo group at C-9 of the cyclopentyl moiety is indicative of a prostaglandin within the E class while $PGE_2$ contains a trans unsaturated double bond at the $C_{13}$-$C_{14}$ and a cis double bond at the $C_5$-$C_6$ position.

A variety of prostaglandins are described and referenced below. However, other prostaglandins will be known to those skilled in the art. Exemplary prostaglandins are disclosed in U.S. Pat. Nos. 4,171,331 and 3,927,197, Norrdin et al., The Role of Prostaglandins in Bone in Vivo, Prostaglandins Leukotriene Essential Fatty Acids 41: 139-150 (1990) is a review of bone anabolic prostaglandins. Any prostaglandin agonist/antagonist may be used in combination with the compounds of this invention. The term prostaglandin agonist/antagonist refers to compounds which bind to prostaglandin receptors e.g., An S. et al., Cloning and Expression of the $EP_2$ Subtype of Human Receptors for Prostaglandin $E_2$, Biochemical and Biophysical Research Communications 197(1): 263-70 (1993)) and mimic the action of prostaglandin in viva (e.g., stimulate bone formation and increase bone mass). Such actions are readily determined by those skilled in the art of standard assays. Eriksen E. F. et al., Bone Histomorphometry, Raven Press, New York, 1994, pp. 1-74; Si. Grier et al., The Use of Dual-Energy X-Ray Absorptiometry In Animals, Inv. Radiol. 31(1): 50-62 (1996); H. W. Wahner and I. Fogelman, The Evaluation of Osteoporosis: Dual Energy X-Ray Absorptiometry in Clinical Practice, Martin Dunitz Ltd. London, pp. 1-296 (1994). A number of these compounds are described and reference below. However, other prostaglandin agonists/antagonists will be known to those skilled in the art. Exemplary prostaglandin agonists/antagonists are disclosed as follows. U.S. Pat. No. 3,932,389 discloses 2-descarboxy-2-(tetrazol-5-yl)-11-desoxy-15-substituted-omega-pentanorprostaglandins useful for bone formation activity. U.S. Pat. No. 4,018,892, discloses 16-aryl-13,14-dihydro-$PGE_2$ p-biphenyl esters useful for bone formation activity. U.S. Pat. No. 4,219,483, discloses 2,3,6-substituted-4-pyrones useful for bone formation activity. U.S. Pat. No. 4,132,847, discloses 2,3,6-substituted-4-pyrones useful for bone formation activity. U.S. Pat. No. 4,000,309, discloses 16-aryl-13,14-dihydro-$PGE_2$ p-biphenyl esters useful for bone formation activity. U.S. Pat. No. 3,982,016, discloses 16-aryl-13,14-dihydro-$PGE_2$ p-biphenyl esters useful for bone formation activity. U.S. Pat. No. 4,621,100, discloses substituted cyclopentanes useful for bone formation activity. U.S. Pat. No. 5,216,183, discloses cyclopentanones useful for bone formation activity.

Sodium fluoride may be used in combination with the compounds of this invention. The term sodium fluoride refers to sodium fluoride in all its forms (e.g., slow release sodium fluoride, sustained release sodium fluoride). Sustained release sodium fluoride is disclosed in U.S. Pat. No. 4,904,478. The activity of sodium fluoride is readily determined by those skilled in the art of biological protocols.

Bone morphogenetic protein may be used in combination with the compounds of this invention (e.g., see Ono et al., Promotion of the Osteogenetic Activity of Recombinant Human Bone Morphogenetic Protein by Prostaglandin $E_1$, Bone 19(6): 581-588 (1996)).

Animal Models

Animal models for autoimmune disorders can be used to assess the efficacy of the Therapeutics or pharmaceutical compositions of invention. Animal models for autoimmune disorders such as type 1 diabetes, thyroid autoimmunity, systemic lupus erythematosus, and glomerulonephritis have been developed (Flanders et al., 1999, Autoimmunity 29:235-246; Krogh et al., 1999, Biochimie 81:511-515; Foster, 1999, Semin. Nephrol. 19:12-24).

The following series of examples are presented by way of illustration and not by way of limitation on the scope of the present invention.

Examples

I. Measuring the Level of IL-12 p40

Northern blot analysis was performed to examine the mRNA levels of IL-12 p35 and p40. Human PBMC and the human monocyte cell line THP-1 cells were stimulated with IFN-γ/SAC in the presence or absence of Compound 1. Human PBMC were isolated by centrifugation using Ficoll-Paque (Pharmacia Biotech, Uppsala, Sweden) and prepared in RPMI medium supplemented with 10% fetal calf serum (FCS), 100 U/ml penicillin, and 100 µg/ml streptomycin, in a 96-well plate with $5 \times 10^5$ cells/well. The cells were then primed with IFN-γ (100 U/ml) and followed by 0.01% SAC or 1 µg/ml LPS, in the presence of different concentrations of Compound 2 or other compounds. The test compounds were prepared in DMSO and the final DMSO concentration was adjusted to 0.25% in all cultures, including the compound-free control. Cell-free supernatants were taken 18 h later for the measurement of cytokines. The THP-1 cells were obtained from American Type Culture Collection (Manassas, Va.) and were cultured in RPMI 1640 (ATCC, Manassas, Va.), supplemented with 10% FCS (ATCC, Manassas, Va.), and 1% penicillin/Streptomycin (Gibco- BRL, New York, N.Y.). Total RNA was isolated and subjected to Northern blot analysis using IL-12 p35 and p40 cDNA probes. We first examined the kinetics of mRNA accumulation in cultures of hPBMC and THP-1 cells primed with IFN-γ followed by SAC stimulation in the presence or absence of 1 μM Compound 1.

In hPBMC, both IL-12 p35 and p40 mRNA were detectable by 4 h and peaked at 6 h after the addition of SAC. The expression of p35 mRNA was completely inhibited by Compound 1 at all sampling times, whereas the expression of the mRNA for the p40 subunit was reduced significantly but incompletely. In THP-1 cells stimulated with IFN-γ/SAC, IL-12 p35 mRNA was barely visible in compound-free control and was undetectable in the presence of 1 μM Compound 1. In contrast, IL-12 p40 mRNA was readily detectable by 4 h and peaked at 6 h after the addition of SAC. Again, Compound 1 significantly but incompletely reduced the expression of the p40 message.

We conducted a dose-response study of the inhibitory effects of Compound 1 on IL-12 mRNA expression in IFN-γ/SAC-stimulated hPBMC. Because both IL-12 p35 and p40 mRNA levels were maximal at 6 h after the addition of SAC, this time point was selected for the dose-response analysis. The induction of IL-12 p35 mRNA accumulation by IFN-γ/SAC was completely reversed by 3 nM Compound 1, with an $IC_{50}$ below 1 nM. In contrast, IL-12 p40 mRNA accumulation was barely inhibited by 1 nM Compound 1, with maximum, though still incomplete inhibition at 10 nM. This apparent weaker inhibition of p40 relative to p35 could be due to more effective inhibition of the p35 promoter or it simply may be the product of the fact that p40 is produced in vast excess to p35 and its inhibition may require greater concentrations of drug.

Thus, Compound 1 caused a decrease in both p35 and p40 mRNA levels. Subsequent nuclear run-on experiments showed that this effect was at the level of transcription initiation.

II. Effect of Compound 2 on IL-12 p35 and p40 Promoter Activity

As a result of the Northern blot findings, we undertook a study of the p35 and p40 promoter activities. We transiently transfected the murine macrophage cell line RAW264.7 with DNA constructs in which the p35 and p40 promoters directed expression of the luciferase reporter gene. The RAW264.7 cell line was obtained from American Type Culture Collection (Manassas, Va.) and was cultured in DMEM (ATCC, Manassas, Va.) supplemented with 10% FCS (ATCC, Manassas, Va.), and 1% penicillin/Streptomycin (Gibco-BRL, New York, N.Y.).

Both p35 and p40 promoter-driven luciferase production in response to stimulation were determined in the presence or absence of Compound 1 and Compound 2. To construct the human IL-12 p35 and p40 promoter/luciferase reporter constructs, we generated p35 (−1.5 kb to +3 bp) and p40 (−1.3 kb to +56 bp) promoter fragments, which contained several sequence motifs of the human IL-12 p35 and p40 genes. The fragments were generated by PCR from genomic DNA obtained from human PBMC using primers as follows: IL-12 p35 1.5 kb-F: 5'-GCAGCATTAGAAGGGGCCTTA-GAGA-3'(SEQ ID NO:3) and IL-12 p35 1.5 kb-R: 5'-TTT-TATAATTGTCCCGAGGCGCG-3' (SEQ ID NO:4); IL-12 p40 −1.3 kb-F: 5'-ACGGCGAGGAAAGTTAGCCCG-3' (SEQ ID NO:5) and IL-12 p40 1.3 kb-R: 5'-TT-GCTCTGGGCAGGACGGAG-3' (SEQ ID NO:6). The deletion in the p40 promoter reporter constructs were generated by PCR with primers as follows: IL-12 p40 −250 bp to +56 bp (p40/−250 bp) F: 5'-CACCCAAAAGTCATTTC-CTC-3'(SEQ ID NO:7) and IL-12 p40 −250 bp to +56 bp (p401/−250 bp) R: 5'-TGCTCTGGGCAGGACGGAG-3' (SEQ ID NO:8); IL-12 p40 −150 bp to +56 bp (p40/−150 bp) F: 5'-AGAGTTGTTTTCAATGTTGCAAC-3' (SEQ ID NO:9) and IL-12 p40 −150 bp to +56 bp (p40/−150 bp) R: 5'-TGCTCTGGGCAGGACGGAG-3'(SEQ ID NO:10). The resulting PCR products were ligated upstream of the luciferase gene in pGL3-Basic vector (Promega). All constructs were verified by DNA sequencing.

RAW267.4 cells were transiently transfected and the cells were then stimulated with murine recombinant IFN-γ (100 ng/ml) for 10 h followed by LPS (1 μg/ml) or SAC (0.025%) in the presence or absence of Compound 1, Compound 2, or a negative control (a structurally-related inactive compound) at different concentrations for an additional 16 h. Transfection was accomplished using SuperFect Transfection Reagent (Qiagen) by the described protocol. Total amount of transfect DNA was kept constant by including the respective control plasmids without insertions.

Cells were co-transfected with the vector pCMV (BD Biosciences Clontech) in which the constitutively active CMV promoter directs β-galactosidase expression for the monitoring of transfection efficiency. Luciferase and β-galactosidase activity were determined in cell extracts prepared according to the Luciferase assay system (Promega) and Luminescent n-gal Detection system (BD Biosciences Clontech). Luciferase activity was then normalized using the β-galactosidase value. The luciferase activities were strongly induced in the case of the IL-12 p40 and p35 promoter constructs in RAW264.7 cells after the stimulation with IFN-γ/LPS or IFN-γ/SAC. This p40 and p35 promoter-driven luciferase expression was suppressed in the presence of Compound 1 and Compound 2, but not the inactive negative control compound. The results are shown in FIGS. 2A-2B. This result supports a mechanism in which Compound 2 inhibits IL-12 transcription. p35 promoter-driven luciferase expression stimulated by IFN-γ/LPS was inhibited more effectively by Compound 2 than by Compound 1, while the negative control compound did not suppress the promoter activity at all. The $IC_{50}$s of Compound 1, Compound 2, and the negative control compound against IL-12 production in THP-1 cells were 40 nM, 10 nM, and greater than 1000 nM, respectively. These results are in agreement with the inhibitory activity against IL-12 protein production evaluated by ELISA, signifying that the inhibition of the p35 promoter activity is a reflection of the inhibitory activity against IL-12. ELISA was performed by the following method. Human IL-12 p70 (heterodimer) was assayed using ELI-PAIR kit from Cell Sciences (Norwood, Mass.), according to the manufacturer's instructions. Human IL-12 p40 was assayed using ELISA kit from Cell Sciences (Norwood, Mass.) according to the manufacturer's instructions.

Northern blot analysis to examine the mRNA levels of IL-12 p35 and p40 was used to elucidate the mechanism of action. Compound 1 caused a decrease in the levels of p35 and p40 mRNA. Nuclear run-on experiments showed that this effect was at the level of transcription initiation. When DNA expression plasmids in which the p35 and p40 promoters directed the expression of the luciferase reporter gene were transfected into cells, it was shown that expression of luciferase could be inhibited by Compound 1 and Compound 2. These results confirm a mechanism in which Compound 2 inhibits IL-12 transcription of the p35 and p40 genes.

We then set out to analyze the IL-12 transcriptional promoter elements that played a role in this effect. We performed deletion analyses using the p40 promoter. This promoter, rather than the p35 promoter, was chosen because the transcriptional elements are better defined in the p40 promoter. To identify the IL-12 inhibitor responsive elements involved in the p40 gene transcription activation, three different promoters were constructed and transiently transfected into RAW264.7 cells. As shown in FIGS. 3A-3B, the promoters that consisted of the NF-κB through the API element region showed diminished promoter activation, while the promoter that contained the 5' flanking region of p40 promoter but had a large proximal deletion displayed significantly decreased promoter activity in response to stimulation with IFN-γ/LPS. Only the promoter which contained the Ets-2 element along with the PU-1, NF-κB and API elements showed high activity of luciferase in response to IFN-γ/LPS stimulation, suggesting that the Ets-2 element plays a role in the regulation of IL-12 p40 promoter activity. This IL-12 promoter-driven luciferase activity was significantly suppressed in the presence of Compound 1. These results suggest that the element that is responsive in the suppression of promoter activity lies in the region from the TATA box to −250 bp in the IL-12 p40 promoter.

To assess the role of individual p40 promoter transcription elements in more detail, mutations within many of these elements have been generated. The goal of this work is to assess the effect of mutations which decrease but do not eliminate p40 promoter activity on inhibition by Compound 2. All mutations in the Ets-2 element have completely eliminated the induction of reporter gene expression, emphasizing the importance of this element. Site-directed mutagenesis of the NFκB element resulted in a p40 promoter having reduced but clearly measurable induction by IFN-γ/LPS. Site-directed mutagenesis was performed with the GeneTailor Site-directed Mutagenesis System (Invitrogen, Carlsbad, Calif.) according to the manufacturer's instructions. The IL-12 p40 Mutant primer sequences were as follows: IL-12 p40-Ets2 mut-F: 5'-TATTCCCCAC-CCAAAAGTCACTTAGTTCATT-3' (SEQ ID NO:11) and IL-12 p40-Ets2 mut-R: 5'-TGACTTTTGGGTGGGGAATAAGGAAGGAGA-3' (SEQ ID NO:12); IL-12 p40-AP-1 mut-F: 5'-TTGTTTTCAATGTTGCAACATTTCTAGTTTA-3' (SEQ ID NO:13) and IL-12 p40-AP-1 mut-R: 5'-TGTTGCAACAT-TGAAAACAACTCTCAAAAC-3' (SEQ ID NO:14); IL-12 p40-NFkB mut-F: 5'-CAAACAAAAAAGGAACT-TCTCAGAAGGTTTT-3' (SEQ ID NO:15) and IL-12 p40-NFkB mut-R: 5'-AGAAGTTCCTTTTTTGTTT-GTCTCTCTCTG-3' (SEQ ID NO:16); IL-12 p40-PU-1 mut-F: 5'-ACAGAGAGAGACAAACAAAACTTCTT-GAAAT-3' (SEQ. ID NO:17) and IL-12 p40-PU-1 mut-R: 5'-TTTTGTTTGTCTCTCTCTGTGTGTGTATCA-3' (SEQ ID NO:18).

Interestingly, inhibition of expression by Compound 2 was reduced in this mutant construct, indicating a role of NFκB. Since the transcription factor NFκB has been shown to be involved in the regulation of IL-12 p40 gene expression, we examined whether STA-1856 alters the binding of NFκB to its cognate site on the p40 promoter. Nuclear extracts were prepared from IFN-γ-primed THP-1 cells that had been treated with or without SAC and incubated in the presence or absence of 1 μM Compound 1 or 10 mM ASA. Isolation of nuclear extracts was accomplished by first suspending THP-1 cells in 20 volumes of buffer A containing 10 mM KCl, 10 mM HEPES (pH 7.9), 1 mM MgCl2, 1 mM dithiothreitol (DTT), 0.1% Nonidet p40 (NP-40), and 0.5 mM phenylmethylsulfonyl fluoride (PMSF) and then homogenizing and centrifuging at 10,000 rpm at 4° C. for 5 min. Nuclear pellets were then suspended in buffer C containing 400 mM NaCl, 20 mM HEPES pH 7.9), 15 mM MgCl2, 0.2 mM EDTA, 1 mM DTT, 25% glycerol, 1 mM PMSF, and 10 μg of leupeptin, 20 μg of pepstatin, and 10 μg of antipain per ml, incubated for 30 min at 4° C., and centrifuge at 14,000 rpm for 20 mm. The supernatants were dialyzed against buffer D containing 100 mM NaCl, 20 mM HEPES (pH 7.9), 20% glycerol, 1 mM PMSF, and 1 mM DTT.

The extracts obtained from this process were used in gel-shift assays using oligonucleotides containing the NFκB target sequence corresponding to the region −121 to −102 from the transcription initiation site of IL-12 p40 or a mutated NFκB binding site. The binding of NFκB to the probe comprising its cognate sequence from the p40 promoter was strongly induced in IFN-γ/SAC-stimulated THP-1 cells. This interaction was specific as it was competed away by an excess of unlabeled probe, but not by a mutated oligonucleotide in which two base-pairs were substituted. Compound 1 did not show any influence on NFκB binding. In contrast, ASA reduced the binding significantly, despite the fact that the percent inhibition of production of IL-12 p70 protein elicited by 1 μM Compound 1 and 10 mM ASA were 97% and 45%, respectively. Combined with the lack of any effect of Compound 2 on IκB, these results show that the strong inhibitory activity of Compound 1/Compound 2 on IL-12 production is not due to a gross reduction in total NFκB binding activity. This is expected since a compound that potently blocks NFkB have a far broader cytokine inhibitory profile than Compound 1/Compound 2.

To understand the action of Compound 2 in NF-κB binding, several NF-κB family members, p50, c-Rel and p65 were investigated using an ELISA based transcriptional factor-DNA binding activity assay system. DNA-transcription factor binding activities assays were performed with EZ-detect transcription Factor kit—NFκB p50 or p65 (Pierce, Rockford, Ill.), and BD Mercury TransFactor Kits—NFkB (BD Biosciences Clontech, Palo Alto, Calif.) according to the manufacturer's instruction.

The binding activities of p50, c-Rel and p65 were significantly increased in nuclear extracts from THP-1 cells 3 hrs after IFN-γ/LPS stimulation. The binding activity of c-Rel was significantly decreased, and p50 was slightly decreased in the presence of Compound 2 (500 nm) for 3 hrs. In the case of p65, the increased binding activity was observed in the presence of Compound 2 in response to the IFN-γ/LPS stimulation. This is a consequence of the lack of binding competition as a result of a decrease in p50 and c-Rel.

III. NF-kB Proteins Translocation

Our DNA-protein interaction study showed that the binding activity of c-Rel and p50, which form functional active heterodimers in IL-12, were decreased, and the binding activity of p65 was increased in response to Compound 2 treatment. In order to understand this changes, the subcellular localization of NF-κB proteins was investigated using western blot analysis. The amount of c-Rel and p50 protein in nuclear were found to be decreased, and the amount of p65 in nuclear was found significantly increased in cells treated with Compound 2 (500 nM) for 3 hr relative to untreated cells. This finding is in agreement with our DNA-protein interaction study, and indicated that the impaired activity of p50/c-Rel and increased p65 binding activity could cause the unbalance of the NF-κB proteins in nucleus and effect the binding activity of p50/c-Rel.

IV. Effect of Compound 2 on c-Rel and ICSBP (Measuring the Level of Both in the Nucleus)

Of the transcription factors that have been analyzed, two factors, ICSBP and c-Rel, seem to be affected by Compound 1/Compound 2 treatment. ICSBP binds indirectly to the Ets-2 site. The primary NFκB trans-activator for IL-12 is the c-Rel/p50 heterodimer. Other dimers (p65/p50 and p50/p50) either lack activity or have inhibitory functions. Thus, c-Rel plays a role in IL-12 transcription as a result of both activation through NFκB and its interaction with ICSBP. Both Western blot analysis and DNA binding studies showed a decrease in nuclear c-Rel levels following Compound 2 treatment. As seen in FIG. 4, a western blot assay of THP1 nuclear c-Rel, p50 and p65 proteins was carried out by the following method: 10% SDS polyacrylamide gels (Invitrogen) were transferred to a Pure nitrocellulose membrane (BioRed, Hercules, Calif.). The membranes were blocked with 5% milk in TBST buffer and then incubated with anti-c-Rel, anti-p65, anti-p50, anti-ICSBP or anti-PU-1 antibody (all the antibodies were purchased from Santa Cruz) at a dilution of 1:500 for 1 h at room temperature or overnight at 4° C. The membranes were washed and incubated with Horseradish Peroxidase-conjugated anti-rabbit IgG or anti-mouse IgG (Amersham, England) at a dilution of 1:2000 at room temperature for 1 h.

Both IFN-γ plus LPS and IFN-γ plus SAC treatment strongly increased the amount of nuclear c-Rel, p65 and p50. Compound 2 treatment significantly reduced the levels of c-Rel, with the post-treatment nuclear c-Rel level being equal to or below the non-stimulated level. In contrast, nuclear p65 protein increased following Compound 2 treatment. p50 levels decreased slightly following Compound 2 treatment, but remained above the non-stimulated levels. Thus, it is shown that Compound 2 treatment causes a reduction in the amount of nuclear c-Rel/p50, the primary IL-12 activating NFκB dimer.

ICSBP, whose expression was reduced by Compound 2, was over-expressed using co-transfection with the IL-12 promoter-Luc report system. The over-expression construct of ICSBP was generated by PCR from cDNA of human PBMC using primers as follow: ICSBP-exp-F: 5'-CCG-GAATTCAGGATGTGTGACCGGAATGG-3' (SEQ ID NO:19) and ICSBP-exp-R: 5'-ATATCTAGAATGGAT-GCAGGACGCAGAC-3' (SEQ ID NO:20), the resulting PCR products was ligated to pCI vector (Promega). ICSBP over-expression increased the level of p40 expression and decreased the inhibition by Compound 2.

V. Effect of Compound 2 on IκB

IκB degradation is one of the steps in the signaling pathway of NFκB dependent genes. The activity of Compound 2 in inducible degradation of IκBα ☐ and IκBβ was investigated in THP-1 cells using Western blot and FACS analysis. The amount of IκBα and Iκbβ in the cytoplasm of THP-1 and RAW267.4 cells was significantly reduced at 30 min in response to induction by IFN-γ/LPS or IFN-γ/SAC. However, there was no significant difference observed between the samples which were treated with or without Compound 2 (500 nM) at 30 min and 2 hrs. Similar results were observed from the Compound 2 pre-treatment samples in which Compound 2 was added 30 mm before stimulation. These results show that Compound 2 does not induce the degradation of IκBα and IκBβ to allow free NFκB to translocate into the nucleus where it can act as a transcription factor.

VI. Measuring the Level of Ets2 in the Nucleus

The transcription factor ICSBP binds to the Ets-2 element indirectly through binding to PU-1. Nuclear extracts were bound to Ets-2 DNA element beads, the beads isolated to separate bound from free protein, and the proteins analyzed on Western blots using antibodies to either ICSBP or PU-1. Conjugation of Ets-2 DNA to beads was accomplished by the following method. Biotinylated DNA fragment encompassing the IL-12 p40 Ets-2 site (−292 to −196) were synthesized from the 1.3 kb wild-type human IL-12 p40 reporter by PCR using a biotinylated primer as detailed in The Journal of Immunology, 2000, vol 165. pages 271-279. PCR products were purified by the Qiaquick Kit (Qiagen, Chatsworth, Calif.). Two µg of biotinylated DNA were conjugated to 100 µl of streptavidin-hound magnetic beads (Dynabeads, M280, Dynal, Lake Success, N.Y.) in buffer containing 10 mM Tris-HCL, pH 8.0, 1 mM EDTA, 0.1 M NaCl. Ten µl of beads conjugated to 2 µg of DNA were equilibrated with TGEDN buffer (120 mM Tris-HCL, pH 8.0, 1 mM EDTA, 0.1 M NaCl, 1 mM DTT, 0.1% Triton X-100, 10% glycerol) and incubated with 500 µg of THP-1 cell nuclear extracts and 20 µg of Herring sperm DNA (GibCo) at 4° C. for 2 h. Beads were washed in TGEDN buffer, and bound materials were eluted in 20 p1 of the same buffer supplemented with 0.5% SDS and 1 M NaCl. Eluted materials were separated by 10% SDS-PAGE and detected by immunoblot analysis using anti-ICSBP or anti-PU-1 antibody.

Figure 5:
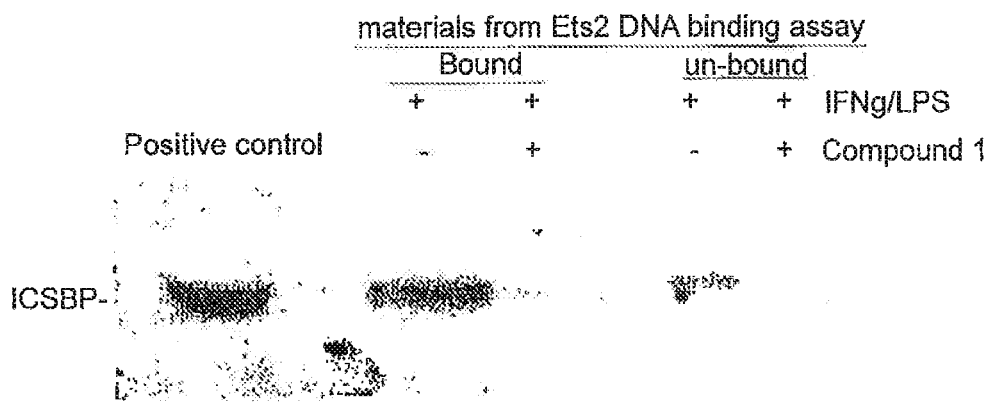
FIG. 5 is a western blot analysis of THP-1 nuclear extracts with anti-ICSBP antibody in stimulated and non-stimulated cells.
Figure 6:
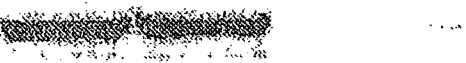
FIG. 6 is a western blot analysis of THP-1 nuclear extracts with anti-PU-1 antibody in stimulated and non-stimulated cells.

Western blot analysis showed a significant reduction in the amount of ICSBP protein in nuclear extracts of THP-1 cells treated with Compound 1, see FIG. 5. In contrast, the levels of PU-1 were unaffected by Compound 1 treatment, see FIG. 6.

Of particular interest is the finding that both ICSBP and c-Rel were reduced in the nuclei of Compound 2 treated cells. Since these two transcription factors interact with each other, a decrease in the levels of both factors would be expected to have a profound effect. Compound 2 selectively inhibits expression of genes which are dependent upon the ICSBP-c-Rel interaction for trans-activation.

Although c-Rel has a role in the expression of both p35 and p40 in monocytes and macrophages as well as p35 in dendritic cells (DCs), p40 expression in dendritic cells is c-Rel-independent (Grumont et al. J. Exp. Med. 2001; 194:1021-1031). If Compound 2 is acting through c-Rel, this drug should inhibit both p40 and p70 production by PBMCs. However, Compound 2 should inhibit the production of p70 (through inhibition of p35) in DCs, but should not inhibit p40 in DCs. This was tested by generating monocyte-derived dendritic cells according to the following method. Human PBMC at $1 \times 10^7$ cells/ml were suspended in serum-free DMEM and incubated for 2 hrs at 37° C. under 5% $CO_2$. The non-adherent cells then were removed by washing with PBS. The adherent cells were cultured in RPMI-1640 medium containing rhIL-4 (100 U/ml) and rhGM-CSF (1000 U/ml) for 6-7 days. The half volume fresh media and full-volume fresh cytokines were added every other day. The cells were then primed with IFN-γ (100 U/ml) and followed by 0.01% SAC or 1 µg/ml LPS, in the presence of different concentrations of Compound 2 or other compounds. The test compounds were prepared in DMSO and the final DMSO concentration was adjusted to 0.25% in all cultures, including the compound-free control. Cell-free supernatants were taken 18 h later for the measurement of cytokines.

Compound 2 did, in fact, inhibit p70 but not p40 production in human DCs (no inhibition at up to 10 µM Compound 2). Also, the induction of IL-12 p40 production following Toxoplasma antigen (STAg) stimulus has been shown to be c-Rel independent. Therefore, if Compound 2 is acting through c-Rel, we should not observe potent inhibition of IL-12 p40 following STAg stimulation. Preliminary results showed that the $IC_{50}$ of Compound 2-mediated p40 inhibition was approximately 1000 times higher with STAg induction relative to IFN-γ/SAC stimulus, while the $IC_{50}$ of dexamethasone was the same in the case of both SAC and STAg stimuli. These two results further confirm that the inhibition of IL-12 production by Compound 2 is via the c-Rel pathway.

Figure 9:
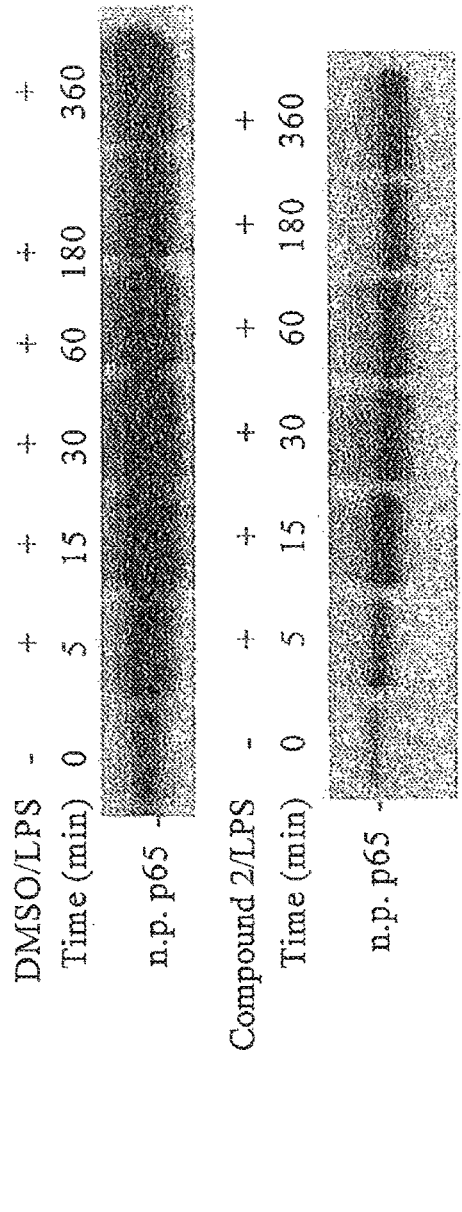
FIG. 9 depicts an immunoblot demonstrating the effect of a test molecule on NF-kB p65 nuclear translocation.
Figure 10:
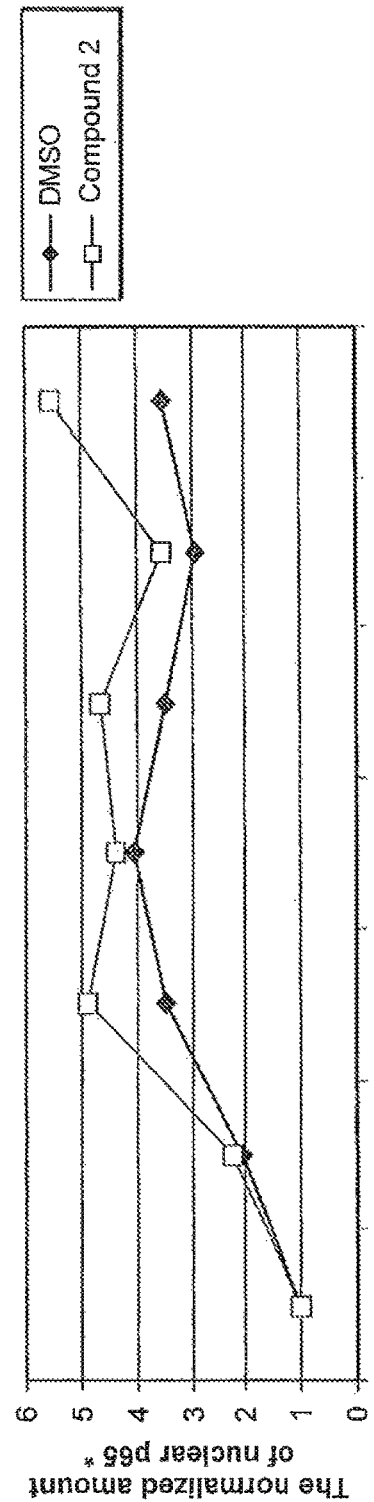
FIG. 10 graphically presents the results of a densitometry showing the effect of a test molecule on p65 nuclear translocation.

VII. Kinetics of the Members of NF-kB Nuclear Translocation in Compound 2-Treated Cells Compound 2 impairs nuclear translocation of c-Rel and p50. We examined the nuclear translocation kinetics of NF-kB family members in LPS stimulated cells treated with Compound 2. THP1 cells were stimulated with LPS in either the presence or absence of 100 nM Compound 2, and the distribution of the NF-κB Rel family members are determined by immunoblotting nuclear (n.p.) extracts collected at 5 min, 15 min, 30 min, 1 h, 3 h and 6 h post-treatment. In response to LPS stimulation, p50 translocated into the nucleus as early as 5 minutes post-stimulation and accumulates as time goes on (FIG. 7, immunoblots and FIG. 8 densitometry). Treatment of LPS-stimulated cells with Compound 2 had no effect on the kinetics of p50 nuclear entry at 5 minutes to 1 hr post-stimulation, and showed a small decrease in nuclear protein levels at 3 hours. The experiment examining p65 nuclear translocation is shown in FIG. 9 (immunoblots) and FIG. 10 (densitometry). In LPS stimulated cells, p65 translocated into the nucleus as early as 5 minutes post-stimulation and accumulated to maximum levels at 15-30 minutes post-stimulation. Treatment of LPS-stimulated cells with Compound 2 had no effect on the kinetics of p65 nuclear entry. The level of nuclear p65 at later times (6 hours) showed a small increase in Compound 2 treated cells relative to untreated cells.

Without wishing to be bound by theory, Compound 2 does not affect the kinetics of p50 and p65 nuclear translocation in response to LPS stimulation. At later times, Compound 2 impairs nuclear translocation of p50 (at 3 h time point), and enhances nuclear translocation of p65 (at 6 h time point), indicating a selective effect on the NF-κB family.

VIII. The Effects of Compound 2 on Nuclear Translocation of p52 and Rel-B

Figure 11:
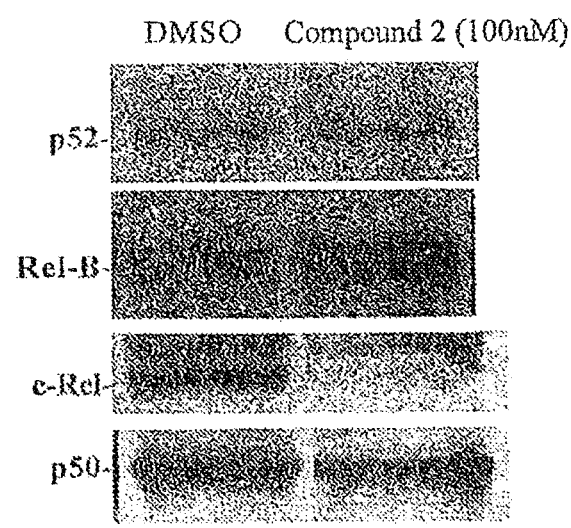
FIG. 11 depicts an immunoblot demonstrating the effect of a test molecule on nuclear translocation of NF-kB members, including c rel.

Rel B and p52 are two members of Rel family, which are preferentially complexed with each other. Like p50 and p65, p52 is found in virtually all cell types, whereas c-Rel and Rel B have only been detected in lymphoid tissues. To determine the effect of Compound 2 on p52 and Rel-B nuclear translocation, THP1 cells were stimulated with IFNg+LPS in either the presence or absence of 100 nM Compound 2, and the distribution of p52 and Rel-B was determined by immunoblotting of nuclear at 6 h post-treatment. As shown in FIG. 11, the nuclear Rel-B was slightly increased in the presence of Compound 2. No significant difference was found in p52. This result indicates that Compound 2 specifically inhibits c-Rel and p50 nuclear translocation, but not other NF-kB p52 and Rel-B nuclear translocation.

Cell Lines and Culture Conditions:

THP-1 cell line were obtained from American Type Culture Collection (Manassas, Va.). The THP-1 cells were cultured in RPMI 1640 (ATCC, Manassas, Va.), supplemented with 10% FCS (ATCC, Manassas, Va.), and 1% penicillin/Streptomycin (Gibco-BRL, New York, N.Y.). The cells were primed with IFNg (100 U/ml) followed by 1 ug/ml LPS in the presence of different concentrations of Compound 2. Compound 2 was prepared in DMSO and the final DMSO concentration was adjusted to 0.25% in the cultures, including the compound-free control. Cell-free supernatants were taken 18 h later for the measurement of cytokines.

Isolation of Nuclear Extracts:

THP-1 cells were suspended in 20 volumes of buffer A containing 10 mM KCl, 10 mM HEPES (pH 7.9), 1 mM MgCl2, 1 mM dithiothreitol (DTT), 0.1% Nonidet p40 (NP-40), and 0.5 mM phenylmethylsulfonyl fluoride (PMSF) and homogenized and centrifuged at 10,000 rpm at 4 C for 5 min. Nuclear pellets were then suspended in buffer C containing 400 mM NaCl, 20 mM HEPES 9 pH 7.9), 15 mM MgCl2, 0.2 mM EDTA, 1 mM DTT, 25% glycerol, 1 mM PMSF, and 10 ug of leupeptin, 20 ug of pepstatin, and 10 ug/ml antipain, incubated for 30 min at 4 C, and centrifuged at 14,000 rpm for 20 min. The supernatants were dialyzed against buffer D containing 100 mM NaCl, 20 mM HEPES (pH 7.9), 20% glycerol, 1 mM PMSF, and 1 mM DTT.

Western Blot:

The 10% SDS Polyacrylamide gels (Invitrogen) were transferred to Pure Nitrocellulose membrane (BioRed, Hercules, Calif.). The membranes were blocked with 5% milk in TBST buffer and incubated with anti-c-Rel, anti-p65, anti-p50, anti-ICSBP or anti-PU-1 antibody (all the antibodies were purchased from Santa Cruz) at a dilution of 1:500 for 1 h at room temperature or overnight at 4 C. The membranes were washed and incubated with Horseradish Peroxidase-conjugated anti-rabbit IgG or anti-mouse IgG (Amersham, England) at a dilution of 1:2000 at room temperature for 1 h.

Compounds 3-14 are expected to have similar activity as Compounds 1 and 2 in the procedures described in Examples I through VIII.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled. Such modifications are intended to fall within the scope of the appended claims.

All references, patent and non-patent, cited herein are incorporated herein by reference in their entirety and for all purposes to the same extent as if each individual publication or patent or patent application was specifically and individually indicated to be incorporated by reference in its entirety for all purposes.

All of the features, specific embodiments and particular substituents disclosed herein may be combined in any combination. Each feature, embodiment or substituent disclosed in this specification may be replaced by an alternative feature, embodiment or substituent serving the same, equivalent, or similar purpose. In the case of chemical compounds, specific values can be combined in any combination resulting in a stable structure. Furthermore, specific values (whether preferred or not) for substituents in one type of chemical structure may be combined with values for other substituents (whether preferred or not) in the same or different type of chemical structure. Thus, unless expressly stated otherwise, each feature, embodiment or substituent disclosed is only an example of a generic series of equivalent or similar features feature, embodiments or substituents.

What is claimed:

1. A method of treating Alzheimer's disease, the method comprising administering to a subject in need thereof, a pharmaceutical composition comprising an amount of Compound 2: N-(3-methyl-benzylidene)-N'-[6-morpholin-4-yl-2-(2-pyridin-2-yl-ethoxy)-pyrimidin-4-yl]-hydrazine.

2. The method of claim 1, wherein the pharmaceutical composition is formulated for a route of administration selected from intravenous, intranasal, or oral.

3. The method of claim 2, wherein the pharmaceutical composition is formulated for intravenous administration.

4. The method of claim 3, wherein the amount of Compound 2 in the composition is from 1 to 50 mg per kilogram of the subject's body weight.

5. The method of claim 2, wherein the pharmaceutical composition is formulated for intranasal administration.

6. The method of claim 5, wherein the amount of Compound 2 in the composition is from 0.1 to 50 mg per kilogram of the subject's body weight.

7. The method of claim 2, wherein the pharmaceutical composition is formulated for oral administration.

8. The method of claim 7, wherein the pharmaceutical composition is a tablet, caplet, hard gelatin capsule, soft gelatin capsules, troche, dragee, dispersion, suspension, or solution.

9. The method of claim 7, wherein the amount of Compound 2 in the composition is from 1 microgram to 500 mg, from 100 micrograms to 5 mg, or from 1 microgram to 50 micrograms per kilogram of the subject's body weight.

10. The method of claim 8, wherein the pharmaceutical composition is a controlled release formulation.

11. The method of claim 1, further comprising administering to the subject an additional prophylactic or therapeutic agent.

12. The method of claim 11, wherein the additional prophylactic or therapeutic agent is an anti-inflammatory agent, an immunomodulatory agent, a leukotriene antagonist, a beta2-agonist, an anticholinergic agent, an antimalarial agent, an anti-viral agent, or an antibiotic.

13. The method of claim 12, wherein the additional prophylactic or therapeutic agent is an anti-inflammatory agent.

14. The method of claim 13, wherein the anti-inflammatory agent is selected from an adrenocorticoid, a corticosteroid, a glucocorticoid, or a steroid.

15. The method of claim 13, wherein the anti-inflammatory agent is a non-steroidal anti-inflammatory agent selected from aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, aspirin, sodium salicylate, choline magnesium trisalicylate, salsalate, diflunisal, salicylsalicylic acid, sulfasalazine, olsalazin, acetaminophen, phenacetin indomethacin, sulindac, etodolac, tolmetin, diclofenac, ketorolac, mefenamic acid, meclofenamic acid, piroxicam, tenoxicam, phenylbutazone, oxyphenthartazone and nabumetone, and pharmaceutically acceptable salts thereof and mixtures thereof.

16. The method of claim 11, wherein the additional prophylactic or therapeutic agent is administered in the same dosage form as Compound 2.

17. The method of claim 11, wherein the additional prophylactic or therapeutic agent is donepezil.

18. The method of claim 1, wherein the subject is human.

* * * * *

SEQUENCE LISTING

<160> NUMBER OF SEQ ID NOS: 20

<210> SEQ ID NO 1
<211> LENGTH: 2337
<212> TYPE: DNA
<213> ORGANISM: Homo sapiens
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (2277)..(2277)
<223> OTHER INFORMATION: a, c, t, g, unknown or other

<400> SEQUENCE: 1

```
cggaaggtgt gagccgcaaa cccagcggag ggcgggaaga aggaggaggc ctctagggtg      60
ntcgggggac tgggggcccc gccggcagag gtccctcggc ctcctgactg actgactgcg     120
gccgcctccg gccaggacgc tgggagctgc ctgcgggaag gtgcggggag cggagccatg     180
gcctccggtg cgtataaccc gtatatagag ataattgaac aacccaggca gaggggaatg     240
cgttttagat acaaatgtga agggcgatca gcaggcagca ttccagggga gcacagcaca     300
gacaacaacc gaacataccc ttctatccag attatgaact attatggaaa aggaaaagtg     360
agaattacat tagtaacaaa gaatgaccca tataaacctc atcctcatga tttagttgga     420
aaagactgca gagacggcta ctatgaagca gaatttggac aagaacgcag acctttgttt     480
ttccaaaatt tgggtattcg atgtgtgaag aaaaaagaag taaagaagc tattattaca     540
agaataaagg caggaatcaa tccattcaat gtccctgaaa acagctgaa tgatattgaa     600
gattgtgacc tcaatgtggt gagactgtgt tttcaagttt ttctccctga tgaacatggt     660
aatttgacga ctgctcttcc tcctgttgtc tcgaacccaa tttatgacaa ccgtgctcca     720
aatactgcag aattaaggat tgtcgtgta aacaagaatt gtggaagtgt cagaggagga     780
gatgaaatat ttctactttg tgacaaagtt cagaaagatg acatagaagt tcgttttgtg     840
ttgaacgatt gggaagcaaa aggcatcttt tcacaagctg atgtacaccg tcaagtagcc     900
attgttttca aaactccacc atattgcaaa gctatcacag aacccgtaac agtaaaaatg     960
cagttgcgga gaccttctga ccaggaagtt agtgaatcta tggattttag atatctgcca    1020
gatgaaaaag atacttacgg caataaagca aagaaacaaa agacaactct gcttttccag    1080
aaactgtgcc aggatcacgt agaaacaggg tttcgccatg ttgaccagga tggtcttgaa    1140
ctcctgacat caggtgatcc acccaccttg gcctcccaaa gtgctgggat tacagttaat    1200
tttcctgaga gaccaagacc tggtctcctc ggttcaattg gagaaggaag atacttcaaa    1260
aaagaaccaa acttgttttc tcatgatgca gttgtgagag aaatgcctac aggggtttca    1320
agtcaagcag aatcctacta tccctcacct gggcccatct caagtggatt gtcacatcat    1380
gcctcaatgg cacctctgcc ttcttcaagc tggtcatcag tggcccaccc cacccacgc    1440
tcaggcaata caaacccact gagtagtttt tcaacaagga cacttccttc taattcgcaa    1500
ggtatcccac cattcctgag aatacctgtt gggaatgatt taaatgcttc taatgcttgc    1560
atttacaaca atgccgatga catagtcgga atggaagcgt catccatgcc atcagcagat    1620
ttatatggta tttctgatcc caacatgctg tctaattgtt ctgtgaatat gatgacaacc    1680
agcagtgaca gcatgggaga gactgataat ccaagacttc tgagcatgaa tcttgaaaac    1740
ccctcatgta attcagtgtt agacccaaga gacttgagac agctccatca gatgtcctct    1800
tccagtatgt cagcaggcgc caattccaat actactgttt ttgtttcaca atcagatgca    1860
```

-continued

```
tttgagggat ctgacttcag ttgtgcagat aacagcatga taaatgagtc gggaccatca    1920
aacagtacta atccaaacag tcatggtttt gttcaagata gtcagtattc aggtattggc    1980
agtatgcaaa atgagcaatt gagtgactcc tttccatatg aattttttca agtataactt    2040
gcaagattta aatccttta aatcttgata ccacctatat agatgcagca ttttgtattt    2100
gtctaactgg ggatataata ctatatttat actgtatata taatactgac tgagaatata    2160
atactgtatt tgagaatata aaaaacttt tcagggaag aagcatacaa ctttggacat    2220
agcgaataca aaattggaag ctgtcataaa aagacaactc agaggccagg cgcaggngct    2280
cacacctgta atcctagcac tttgggaggc caaggcgggt ggatcacttg agaccag    2337
```

<210> SEQ ID NO 2
<211> LENGTH: 619
<212> TYPE: PRT
<213> ORGANISM: Homo sapiens

<400> SEQUENCE: 2

```
Met Ala Ser Gly Ala Tyr Asn Pro Tyr Ile Glu Ile Ile Glu Gln Pro
1               5                   10                  15

Arg Gln Arg Gly Met Arg Phe Arg Tyr Lys Cys Glu Gly Arg Ser Ala
            20                  25                  30

Gly Ser Ile Pro Gly Glu His Ser Thr Asp Asn Asn Arg Thr Tyr Pro
        35                  40                  45

Ser Ile Gln Ile Met Asn Tyr Gly Lys Gly Lys Val Arg Ile Thr
    50                  55                  60

Leu Val Thr Lys Asn Asp Pro Tyr Lys Pro His Pro His Asp Leu Val
65                  70                  75                  80

Gly Lys Asp Cys Arg Asp Gly Tyr Tyr Glu Ala Glu Phe Gly Gln Glu
                85                  90                  95

Arg Arg Pro Leu Phe Phe Gln Asn Leu Gly Ile Arg Cys Val Lys Lys
            100                 105                 110

Lys Glu Val Lys Glu Ala Ile Ile Thr Arg Ile Lys Ala Gly Ile Asn
        115                 120                 125

Pro Phe Asn Val Pro Glu Lys Gln Leu Asn Asp Ile Glu Asp Cys Asp
    130                 135                 140

Leu Asn Val Val Arg Leu Cys Phe Gln Val Phe Leu Pro Asp Glu His
145                 150                 155                 160

Gly Asn Leu Thr Thr Ala Leu Pro Pro Val Val Ser Asn Pro Ile Tyr
                165                 170                 175

Asp Asn Arg Ala Pro Asn Thr Ala Glu Leu Arg Ile Cys Arg Val Asn
            180                 185                 190

Lys Asn Cys Gly Ser Val Arg Gly Gly Asp Glu Ile Phe Leu Leu Cys
        195                 200                 205

Asp Lys Val Gln Lys Asp Asp Ile Glu Val Arg Phe Val Leu Asn Asp
    210                 215                 220

Trp Glu Ala Lys Gly Ile Phe Ser Gln Ala Asp Val His Arg Gln Val
225                 230                 235                 240

Ala Ile Val Phe Lys Thr Pro Pro Tyr Cys Lys Ala Ile Thr Glu Pro
                245                 250                 255

Val Thr Val Lys Met Gln Leu Arg Arg Pro Ser Asp Gln Glu Val Ser
            260                 265                 270

Glu Ser Met Asp Phe Arg Tyr Leu Pro Asp Glu Lys Asp Thr Tyr Gly
        275                 280                 285
```

-continued

```
Asn Lys Ala Lys Lys Gln Lys Thr Thr Leu Leu Phe Gln Lys Leu Cys
    290                 295                 300
Gln Asp His Val Glu Thr Gly Phe Arg His Val Asp Gln Asp Gly Leu
305                 310                 315                 320
Glu Leu Leu Thr Ser Gly Asp Pro Pro Thr Leu Ala Ser Gln Ser Ala
                325                 330                 335
Gly Ile Thr Val Asn Phe Pro Glu Arg Pro Arg Pro Gly Leu Leu Gly
            340                 345                 350
Ser Ile Gly Glu Gly Arg Tyr Phe Lys Lys Glu Pro Asn Leu Phe Ser
        355                 360                 365
His Asp Ala Val Arg Glu Met Pro Thr Gly Val Ser Ser Gln Ala
370                 375                 380
Glu Ser Tyr Tyr Pro Ser Pro Gly Pro Ile Ser Ser Gly Leu Ser His
385                 390                 395                 400
His Ala Ser Met Ala Pro Leu Pro Ser Ser Ser Trp Ser Ser Val Ala
                405                 410                 415
His Pro Thr Pro Arg Ser Gly Asn Thr Asn Pro Leu Ser Ser Phe Ser
            420                 425                 430
Thr Arg Thr Leu Pro Ser Asn Ser Gln Gly Ile Pro Pro Phe Leu Arg
        435                 440                 445
Ile Pro Val Gly Asn Asp Leu Asn Ala Ser Asn Ala Cys Ile Tyr Asn
450                 455                 460
Asn Ala Asp Asp Ile Val Gly Met Glu Ala Ser Ser Met Pro Ser Ala
465                 470                 475                 480
Asp Leu Tyr Gly Ile Ser Asp Pro Asn Met Leu Ser Asn Cys Ser Val
                485                 490                 495
Asn Met Met Thr Thr Ser Ser Asp Ser Met Gly Glu Thr Asp Asn Pro
            500                 505                 510
Arg Leu Leu Ser Met Asn Leu Glu Asn Pro Ser Cys Asn Ser Val Leu
        515                 520                 525
Asp Pro Arg Asp Leu Arg Gln Leu His Gln Met Ser Ser Ser Ser Met
530                 535                 540
Ser Ala Gly Ala Asn Ser Asn Thr Thr Val Phe Val Ser Gln Ser Asp
545                 550                 555                 560
Ala Phe Glu Gly Ser Asp Phe Ser Cys Ala Asp Asn Ser Met Ile Asn
                565                 570                 575
Glu Ser Gly Pro Ser Asn Ser Thr Asn Pro Asn Ser His Gly Phe Val
            580                 585                 590
Gln Asp Ser Gln Tyr Ser Gly Ile Gly Ser Met Gln Asn Glu Gln Leu
        595                 600                 605
Ser Asp Ser Phe Pro Tyr Glu Phe Phe Gln Val
    610                 615
```

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
gcagcattag aagggcctt agaga                                        25

<210> SEQ ID NO 4
<211> LENGTH: 23

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttttataatt gtcccgaggc gcg                                             23

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acggcgagga aagttagccc g                                               21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttgctctggg caggacggag                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cacccaaaag tcatttcctc                                                 20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgctctgggc aggacggag                                                  19

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agagttgttt tcaatgttgc aac                                             23

<210> SEQ ID NO 10
<211> LENGTH: 19
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 10
tgctctgggc aggacggag                                                   19

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tattccccac ccaaaagtca cttagttcat t                                     31

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgacttttgg gtggggaata aggaaggaga                                       30

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttgttttcaa tgttgcaaca tttctagttt a                                     31

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgttgcaaca ttgaaaacaa ctctcaaaac                                       30

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caaacaaaaa aggaacttct cagaaggttt t                                     31

<210> SEQ ID NO 16
<211> LENGTH: 30
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 16
agaagttcct tttttgtttg tctctctctg                                        30

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acagagagag acaaacaaaa cttcttgaaa t                                      31

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttttgtttgt ctctctctgt gtgtgtatca                                        30

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccggaattca ggatgtgtga ccggaatgg                                         29

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atatctagaa tggatgcagg acgcagac                                          28
```